US008207400B2

(12) United States Patent
Lopez de Leon et al.

(10) Patent No.: US 8,207,400 B2
(45) **Date of Patent: *Jun. 26, 2012**

(54) POLYPEPTIDES HAVING CELLULOLYTIC ENHANCING ACTIVITY AND POLYNUCLEOTIDES ENCODING SAME

(75) Inventors: Alfredo Lopez de Leon, Davis, CA (US); Hanshu Ding, Davis, CA (US); Kimberly Brown, Elk Grove, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,755

(22) Filed: Sep. 21, 2011

(65) Prior Publication Data

US 2012/0011619 A1 Jan. 12, 2012

Related U.S. Application Data

(62) Division of application No. 12/130,722, filed on May 30, 2008, now Pat. No. 8,044,264.

(60) Provisional application No. 60/941,234, filed on May 31, 2007.

(51) Int. Cl.

| | |
|---|---|
| ***C12N 15/31*** | (2006.01) |
| ***C12N 15/82*** | (2006.01) |
| ***C12N 15/10*** | (2006.01) |
| ***C12N 15/52*** | (2006.01) |
| ***A01H 5/00*** | (2006.01) |

(52) U.S. Cl. ........ 800/288; 800/284; 800/295; 800/278; 435/320.1; 435/468; 536/23.1; 536/23.2; 536/23.7

(58) Field of Classification Search ........................ None
See application file for complete search history.

(56) References Cited

U.S. PATENT DOCUMENTS

| | | | | |
|---|---|---|---|---|
| 2005/0191736 A1* | 9/2005 | Brown et al. | ................ | 435/161 |
| 2007/0077630 A1 | 4/2007 | Harris et al. | | |

FOREIGN PATENT DOCUMENTS

| | | |
|---|---|---|
| WO | 2004031378 A2 | 4/2004 |
| WO | 2005074647 A2 | 8/2005 |
| WO | 2005074656 A2 | 8/2005 |

OTHER PUBLICATIONS

Breuil et al., 1986, Biotechnol Lett 8 (9), 673-676.
Gikes et al., 1991, Microbiol Rev 55 (2), 305-315.
Rey et al., 2003, Appl Biochem Biotechnol 111, 153-166.
UNIPROTKB, XP-002489741, Accession No. Q7S439, 2003.

* cited by examiner

*Primary Examiner* — Brent T Page
(74) *Attorney, Agent, or Firm* — Robert L. Starnes; Eric J. Fechter

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

27 Claims, 12 Drawing Sheets

```
       M  K  G  L   S  L  L   A  A  A   S  A  A  T   A  H  T   I  F  V
  1    ATGAAGGGCC TCAGCCTCCT CGCCGCTGCG TCGGCAGCGA CTGCTCATAC CATCTTCGTG
       Q  L  E  S   G  G  T   T  Y  P   V  S  Y  G   I  R  D   P  S  Y
 61    CAGCTCGAGT CAGGGGGAAC GACCTATCCG GTATCCTACG GCATCCGGGA CCCTAGCTAC
       D  G  P  I   T  D  V   T  S  D   S  L  A  C   N  G  P   P  N  P
121    GACGGTCCCA TCACCGACGT CACCTCCGAC TCACTGGCTT GCAATGGTCC CCCGAACCCC
       T  T  P  S   P  Y  I   I  N  V   T  A  G  T   T  V  A   A  I  W
181    ACGACGCCGT CCCCGTACAT CATCAACGTC ACCGCCGGCA CCACGGTCGC GGCGATCTGG
       R  H  T  L   T  S  G   P  D  D   V  M  D  A   S  H  K   G  P  T
241    AGGCACACCC TCACATCCGG CCCCGACGAT GTCATGGACG CCAGCCACAA GGGGCCGACC
       L  A  Y  L   K  K  V   D  D  A   L  T  D  T   G  I  G   G  G  W
301    CTGGCCTACC TCAAGAAGGT CGATGATGCC TTGACCGACA CGGGTATCGG CGGCGGCTGG
       F  K  I  Q   E  A  G   Y  D  N   G  N  W  A   T  S  T   V  I  T
361    TTCAAGATCC AGGAGGCCGG TTACGACAAT GGCAATTGGG CTACCAGCAC GGTGATCACC
       N  G  G  F   Q  Y  I   D  I  P   A  C  I  P   N  G  Q   Y  L  L
421    AACGGTGGCT TCCAATATAT TGACATCCCC GCCTGCATTC CCAACGGCCA GTATCTGCTC
       R  A  E  M   I  A  L   H  A  A   S  T  Q  G   G  A  Q   L  Y  M
481    CGCGCCGAGA TGATCGCGCT CCACGCCGCC AGCACGCAGG GTGGTGCCCA GCTCTACATG
       E  C  A  Q   I  N  V   V  G  G   S  G  S  A   S  P  Q   T  Y  S
541    GAGTGCGCGC AGATCAACGT GGTGGGCGGC TCCGGCAGCG CCAGCCCGCA GACGTACAGC
       I  P  G  I   Y  Q  A   T  D  P   G  L  L  I   N  I  Y   S  M  T
601    ATCCCGGGCA TCTACCAGGC AACCGACCCG GGCCTGCTGA TCAACATCTA CTCCATGACG
       P  S  S  Q   Y  T  I   P  G  P   P  L  F  T   C  S  G   S  G  N
661    CCGTCCAGCC AGTACACCAT TCCGGGTCCG CCCCTGTTCA CCTGCAGCGG CAGCGGCAAC
       N  G  G  G   S  N  P   S  G  G   Q  T  T  T   A  K  P   T  T  T
721    AACGGCGGCG GCAGCAACCC GTCGGGCGGG CAGACCACGA CGGCGAAGCC CACGACGACG
       T  A  A  T   T  T  S   S  A  A   P  T  S  S   Q  G  G   S  S  G
781    ACGGCGGCGA CGACCACCTC CTCCGCCGCT CCTACCAGCA GCCAGGGGGG CAGCAGCGGT
       C  T  V  P   Q  W  Q   Q  C  G   G  I  S  F   T  G  C   T  T  C
841    TGCACCGTTC CCCAGTGGCA GCAGTGCGGT GGCATCTCGT TCACCGGCTG CACCACCTGC
       A  A  G  Y   T  C  K   Y  L  N   D  Y  Y  S   Q  C  Q   *
901    GCGGCGGGCT ACACCTGCAA GTATCTGAAC GACTATTACT CGCAATGCCA GTAA
```

Fig. 1

```
ATG AAG CTT GGT TGG ATC GAG GTG GCC GCA TTG GCG GCT GCC TCA GTA GTC AGT GCC
 M   K   L   G   W   I   E   V   A   A   L   A   A   A   S   V   V   S   A
```

Fig. 10

```
ATG CGT TCC TCC CCC CTC CTC CGC TCC GCC GTT GTG GCC GCC CTG CCG GTG TTG GCC CTT GCC
 M   R   S   S   P   L   L   R   S   A   V   V   A   A   L   P   V   L   A   L   A
```

Fig. 11

SEQUENCE LISTING

```
<160> NUMBER OF SEQ ID NOS: 82

<210> SEQ ID NO 1
<211> LENGTH: 954
<212> TYPE: DNA
<213> ORGANISM: Thielavia terrestris

<400> SEQUENCE: 1

atgaagggcc tcagcctcct cgccgctgcg tcggcagcga ctgctcatac catcttcgtg      60

cagctcgagt caggggggaac gacctatccg gtatcctacg gcatccggga ccctagctac     120

gacggtccca tcaccgacgt cacctccgac tcactggctt gcaatggtcc cccgaacccc     180

acgacgccgt ccccgtacat catcaacgtc accgccggca ccacggtcgc ggcgatctgg     240

aggcacaccc tcacatccgg ccccgacgat gtcatggacg ccagccacaa ggggccgacc     300

ctggcctacc tcaagaaggt cgatgatgcc ttgaccgaca cgggtatcgg cggcggctgg     360

ttcaagatcc aggaggccgg ttacgacaat ggcaattggg ctaccagcac ggtgatcacc     420

aacggtggct tccaatatat tgacatcccc gcctgcattc ccaacggcca gtatctgctc     480

cgcgccgaga tgatcgcgct ccacgccgcc agcacgcagg gtggtgccca gctctacatg     540
```

```
gagtgcgcgc agatcaacgt ggtgggcggc tccggcagcg ccagcccgca gacgtacagc    600

atcccgggca tctaccaggc aaccgacccg ggcctgctga tcaacatcta ctccatgacg    660

ccgtccagcc agtacaccat tccgggtccg cccctgttca cctgcagcgg cagcggcaac    720

aacggcggcg gcagcaaccc gtcgggcggg cagaccacga cggcgaagcc cacgacgacg    780

acggcggcga cgaccacctc ctccgccgct cctaccagca gccagggggg cagcagcggt    840

tgcaccgttc cccagtggca gcagtgcggt ggcatctcgt tcaccggctg caccacctgc    900

gcggcgggct acacctgcaa gtatctgaac gactattact cgcaatgcca gtaa          954


<210> SEQ ID NO 2
<211> LENGTH: 317
<212> TYPE: PRT
<213> ORGANISM: Thielavia terrestris

<400> SEQUENCE: 2

Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
        35                  40                  45

Ser Asp Ser Leu Ala Cys Asn Gly Pro Pro Asn Pro Thr Thr Pro Ser
    50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Thr Cys Ala Ala Gly Tyr
    290                 295                 300

Thr Cys Lys Tyr Leu Asn Asp Tyr Tyr Ser Gln Cys Gln
```

305 310 315

<210> SEQ ID NO 3
<211> LENGTH: 16
<212> TYPE: DNA
<213> ORGANISM: Thielavia terrestris

<400> SEQUENCE: 3
gtaaaacgac ggccag 16

<210> SEQ ID NO 4
<211> LENGTH: 25
<212> TYPE: DNA
<213> ORGANISM: Thielavia terrestris
<220> FEATURE:
<221> NAME/KEY: misc_feature
<222> LOCATION: (24)..(24)
<223> OTHER INFORMATION: V=G, A, C
<220> FEATURE:
<221> NAME/KEY: misc_feature
<222> LOCATION: (25)..(25)
<223> OTHER INFORMATION: N=G, A, C, T

<400> SEQUENCE: 4
tttttttttt tttttttttt tttvn 25

<210> SEQ ID NO 5
<211> LENGTH: 34
<212> TYPE: DNA
<213> ORGANISM: Thielavia terrestris

<400> SEQUENCE: 5
actggattta ccatgaaggg cctcagcctc ctcg 34

<210> SEQ ID NO 6
<211> LENGTH: 40
<212> TYPE: DNA
<213> ORGANISM: Thielavia terrestris

<400> SEQUENCE: 6
tcacctctag ttaattaatt actggcattg cgagtaatag 40

<210> SEQ ID NO 7
<211> LENGTH: 29
<212> TYPE: DNA
<213> ORGANISM: Trichoderma reesei

<400> SEQUENCE: 7
aacgttaatt aaggaatcgt tttgtgttt 29

<210> SEQ ID NO 8
<211> LENGTH: 29
<212> TYPE: DNA
<213> ORGANISM: Trichoderma reesei

<400> SEQUENCE: 8
agtactagta gctccgtggc gaaagcctg 29

<210> SEQ ID NO 9
<211> LENGTH: 918
<212> TYPE: DNA
<213> ORGANISM: Humicola insolens

<400> SEQUENCE: 9
atgcgttcct cccccctcct cccgtccgcc gttgtggccg ccctgccggt gttggccctt 60

```
gccgctgatg gcaggtccac ccgctactgg gactgctgca agccttcgtg cggctgggcc    120

aagaaggctc ccgtgaacca gcctgtcttt tcctgcaacg ccaacttcca gcgtatcacg    180

gacttcgacg ccaagtccgg ctgcgagccg ggcggtgtcg cctactcgtg cgccgaccag    240

accccatggg ctgtgaacga cgacttcgcg ctcggttttg ctgccacctc tattgccggc    300

agcaatgagg cgggctggtg ctgcgcctgc tacgagctca ccttcacatc cggtcctgtt    360

gctggcaaga agatggtcgt ccagtccacc agcactggcg gtgatcttgg cagcaaccac    420

ttcgatctca acatccccgg cggcggcgtc ggcatcttcg acggatgcac tccccagttc    480

ggcggtctgc ccggccagcg ctacggcggc atctcgtccc gcaacgagtg cgatcggttc    540

cccgacgccc tcaagcccgg ctgctactgg cgcttcgact ggttcaagaa cgccgacaat    600

ccgagcttca gcttccgtca ggtccagtgc ccagccgagc tcgtcgctcg caccggatgc    660

cgccgcaacg acgacggcaa cttccctgcc gtccagatcc cctccagcag caccagctct    720

ccggtcaacc agcctaccag caccagcacc acgtccacct ccaccacctc gagcccgcca    780

gtccagccta cgactcccag cggctgcact gctgagaggt gggctcagtg cggcggcaat    840

ggctggagcg gctgcaccac ctgcgtcgct ggcagcactt gcacgaagat taatgactgg    900

taccatcagt gcctgtag                                                  918
```

<210> SEQ ID NO 10
<211> LENGTH: 305
<212> TYPE: PRT
<213> ORGANISM: Humicola insolens

<400> SEQUENCE: 10

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220
```

```
Asp Gly Asn Phe Pro Ala Val Gln Ile Pro Ser Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305


<210> SEQ ID NO 11
<211> LENGTH: 31
<212> TYPE: DNA
<213> ORGANISM: Saccharomyces cerevisiae

<400> SEQUENCE: 11

ttgaattgaa aatagattga tttaaaactt c                                31


<210> SEQ ID NO 12
<211> LENGTH: 25
<212> TYPE: DNA
<213> ORGANISM: Saccharomyces cerevisiae

<400> SEQUENCE: 12

ttgcatgcgt aatcatggtc atagc                                       25


<210> SEQ ID NO 13
<211> LENGTH: 26
<212> TYPE: DNA
<213> ORGANISM: Saccharomyces cerevisiae

<400> SEQUENCE: 13

ttgaattcat gggtaataac tgatat                                      26


<210> SEQ ID NO 14
<211> LENGTH: 32
<212> TYPE: DNA
<213> ORGANISM: Saccharomyces cerevisiae

<400> SEQUENCE: 14

aaatcaatct attttcaatt caattcatca tt                               32


<210> SEQ ID NO 15
<211> LENGTH: 11
<212> TYPE: DNA
<213> ORGANISM: Aspergillus niger

<400> SEQUENCE: 15

gtactaaaac c                                                      11


<210> SEQ ID NO 16
<211> LENGTH: 11
<212> TYPE: DNA
<213> ORGANISM: Aspergillus niger

<400> SEQUENCE: 16

ccgttaaatt t                                                      11


<210> SEQ ID NO 17
```

<211> LENGTH: 45
<212> TYPE: DNA
<213> ORGANISM: Aspergillus niger

<400> SEQUENCE: 17
ggatgctgtt gactccggaa atttaacggt ttggtcttgc atccc 45

<210> SEQ ID NO 18
<211> LENGTH: 14
<212> TYPE: DNA
<213> ORGANISM: Aspergillus niger

<400> SEQUENCE: 18
atgcaattta aact 14

<210> SEQ ID NO 19
<211> LENGTH: 14
<212> TYPE: DNA
<213> ORGANISM: Aspergillus niger

<400> SEQUENCE: 19
cggcaattta acgg 14

<210> SEQ ID NO 20
<211> LENGTH: 44
<212> TYPE: DNA
<213> ORGANISM: Aspergillus niger

<400> SEQUENCE: 20
ggtattgtcc tgcagacggc aatttaacgg cttctgcgaa tcgc 44

<210> SEQ ID NO 21
<211> LENGTH: 29
<212> TYPE: DNA
<213> ORGANISM: Humicola insolens

<400> SEQUENCE: 21
aagcttaagc atgcgttcct ccccctcc 29

<210> SEQ ID NO 22
<211> LENGTH: 32
<212> TYPE: DNA
<213> ORGANISM: Humicola insolens

<400> SEQUENCE: 22
ctgcagaatt ctacaggcac tgatggtacc ag 32

<210> SEQ ID NO 23
<211> LENGTH: 32
<212> TYPE: DNA
<213> ORGANISM: Trichoderma reesei

<400> SEQUENCE: 23
ctgcagaatt ctacaggcac tgatggtacc ag 32

<210> SEQ ID NO 24
<211> LENGTH: 36
<212> TYPE: DNA
<213> ORGANISM: Trichoderma reesei

<400> SEQUENCE: 24
accgcggact gcgcatcatg cgttcctccc ccctcc 36

<210> SEQ ID NO 25

<211> LENGTH: 29
<212> TYPE: DNA
<213> ORGANISM: Trichoderma reesei

<400> SEQUENCE: 25
aaacgtcgac cgaatgtagg attgttatc 29

<210> SEQ ID NO 26
<211> LENGTH: 17
<212> TYPE: DNA
<213> ORGANISM: Trichoderma reesei

<400> SEQUENCE: 26
gatgcgcagt ccgcggt 17

<210> SEQ ID NO 27
<211> LENGTH: 29
<212> TYPE: DNA
<213> ORGANISM: Trichoderma reesei

<400> SEQUENCE: 27
aaacgtcgac cgaatgtagg attgttatc 29

<210> SEQ ID NO 28
<211> LENGTH: 36
<212> TYPE: DNA
<213> ORGANISM: Trichoderma reesei

<400> SEQUENCE: 28 ggaggggggga ggaacgcatg atgcgcagtc cgcggt 36

<210> SEQ ID NO 29
<211> LENGTH: 29
<212> TYPE: DNA
<213> ORGANISM: Trichoderma reesei

<400> SEQUENCE: 29
aaacgtcgac cgaatgtagg attgttatc 29

<210> SEQ ID NO 30
<211> LENGTH: 32
<212> TYPE: DNA
<213> ORGANISM: Trichoderma reesei

<400> SEQUENCE: 30
ctgcagaatt ctacaggcac tgatggtacc ag 32

<210> SEQ ID NO 31
<211> LENGTH: 2771
<212> TYPE: DNA
<213> ORGANISM: Aspergillus oryzae

<400> SEQUENCE: 31
ctgttctgct ggttacctgc cacgttatca tgaagcttgg ttggatcgag gtggccgcat 60
tggcggctgc ctcagtagtc agtgccaagg atgatctcgc gtactcccct cctttctacc 120
cttccccatg ggcagatggt cagggtgaat gggcggaagt atacaaacgc gctgtagaca 180
tagtttccca gatgacgttg acagagaaag tcaacttaac gactggaaca ggatggcaac 240
tagagaggtg tgttggacaa actggcagtg ttcccagact caacatcccc agcttgtgtt 300
tgcaggatag tcctcttggt attcgtttct cggactacaa ttcagctttc cctgcgggtg 360
ttaatgtcgc tgccacctgg gacaagacgc tcgcctacct tcgtggtcag gcaatgggtg 420

-continued

```
aggagttcag tgataagggt attgacgttc agctgggtcc tgctgctggc cctctcggtg    480
ctcatccgga tggcggtaga aactgggaag gtttctcacc agatccagcc ctcaccggtg    540
tactttttgc ggagacgatt aagggtattc aagatgctgg tgtcattgcg acagctaagc    600
attatatcat gaacgaacaa gagcatttcc gccaacaacc cgaggctgcg ggttacggat    660
tcaacgtaag cgacagtttg agttccaacg ttgatgacaa gactatgcat gaattgtacc    720
tctggccctt cgcggatgca gtacgcgctg gagtcggtgc tgtcatgtgc tcttacaacc    780
aaatcaacaa cagctacggt tgcgagaata gcgaaactct gaacaagctt ttgaaggcgg    840
agcttggttt ccaaggcttc gtcatgagtg attggaccgc tcatcacagc ggcgtaggcg    900
ctgctttagc aggtctggat atgtcgatgc ccggtgatgt taccttcgat agtggtacgt    960
ctttctgggg tgcaaacttg acggtcggtg tccttaacgg tacaatcccc caatggcgtg   1020
ttgatgacat ggctgtccgt atcatggccg cttattacaa ggttggccgc gacaccaaat   1080
acacccctcc caacttcagc tcgtggacca gggacgaata tggtttcgcg cataaccatg   1140
tttcggaagg tgcttacgag agggtcaacg aattcgtgga cgtgcaacgc gatcatgccg   1200
acctaatccg tcgcatcggc gcgcagagca ctgttctgct gaagaacaag ggtgccttgc   1260
ccttgagccg caaggaaaag ctggtcgccc ttctgggaga ggatgcgggt tccaactcgt   1320
ggggcgctaa cggctgtgat gaccgtggtt gcgataacgg taccettgcc atggcctggg   1380
gtagcggtac tgcgaatttc ccatacctcg tgacaccaga gcaggcgatt cagaacgaag   1440
ttcttcaggg ccgtggtaat gtcttcgccg tgaccgacag ttgggcgctc gacaagatcg   1500
ctgcggctgc ccgccaggcc agcgtatctc tcgtgttcgt caactccgac tcaggagaaa   1560
gctatcttag tgtggatgga aatgagggcg atcgtaacaa catcactctg tggaagaacg   1620
gcgacaatgt ggtcaagacc gcagcgaata actgtaacaa caccgtggtc atcatccact   1680
ccgtcggacc agttttgatc gatgaatggt atgaccaccc caatgtcact ggtattctct   1740
gggctggtct gccaggccag gagtctggta actccatcgc cgatgtgctg tacggtcgtg   1800
tcaaccctgg cgccaagtct cctttcactt ggggcaagac ccgggagtcg tatggttctc   1860
ccttggtcaa ggatgccaac aatggcaacg gagcgcccca gtctgatttc acccagggtg   1920
ttttcatcga ttaccgccat ttcgataagt tcaatgagac ccctatctac gagtttggct   1980
acggcttgag ctacaccacc ttcgagctct ccgacctcca tgttcagccc ctgaacgcgt   2040
cccgatacac tcccaccagt ggcatgactg aagctgcaaa gaactttggt gaaattggcg   2100
atgcgtcgga gtacgtgtat ccggaggggc tggaaaggat ccatgagttt atctatccct   2160
ggatcaactc taccgacctg aaggcatcgt ctgacgattc taactacggc tgggaagact   2220
ccaagtatat tcccgaaggc gccacggatg ggtctgccca gccccgtttg cccgctagtg   2280
gtggtgccgg aggaaacccc ggtctgtacg aggatctttt ccgcgtctct gtgaaggtca   2340
agaacacggg caatgtcgcc ggtgatgaag ttcctcagct gtacgtttcc ctaggcggcc   2400
cgaatgagcc caaggtggta ctgcgcaagt ttgagcgtat tcacttggcc ccttcgcagg   2460
aggccgtgtg gacaacgacc cttacccgtc gtgaccttgc aaactgggac gtttcggctc   2520
aggactggac cgtcactcct taccccaaga cgatctacgt tggaaactcc tcacggaaac   2580
tgccgctcca ggcctcgctg cctaaggccc agtaaggggc aagtcctgat tgtacagagc   2640
atttcgagat ttatgatgta catgtttatg aatgacctag ggtagggtaa tacttagtag   2700
ggttagttct aattcttgga gtcaagtatt gactcactgg gccgataaaa aaaaaaaaaa   2760
aaaaaaaaaa a                                                        2771
```

<210> SEQ ID NO 32
<211> LENGTH: 861
<212> TYPE: PRT
<213> ORGANISM: Aspergillus oryzae

<400> SEQUENCE: 32

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380
```

```
Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Ala Arg Gln
                485                 490                 495

Ala Ser Val Ser Leu Val Phe Val Asn Ser Asp Ser Gly Glu Ser Tyr
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815
```

```
Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860


<210> SEQ ID NO 33
<211> LENGTH: 46
<212> TYPE: DNA
<213> ORGANISM: Aspergillus oryzae

<400> SEQUENCE: 33

atagtcaacc gcggactgcg catcatgaag cttggttgga tcgagg                   46


<210> SEQ ID NO 34
<211> LENGTH: 26
<212> TYPE: DNA
<213> ORGANISM: Aspergillus oryzae

<400> SEQUENCE: 34

actagtttac tgggccttag gcagcg                                         26


<210> SEQ ID NO 35
<211> LENGTH: 26
<212> TYPE: DNA
<213> ORGANISM: Trichoderma reesei

<400> SEQUENCE: 35

gtcgactcga agcccgaatg taggat                                         26


<210> SEQ ID NO 36
<211> LENGTH: 45
<212> TYPE: DNA
<213> ORGANISM: Trichoderma reesei

<400> SEQUENCE: 36

cctcgatcca accaagcttc atgatgcgca gtccgcggtt gacta                    45


<210> SEQ ID NO 37
<211> LENGTH: 57
<212> TYPE: DNA
<213> ORGANISM: Aspergillus oryzae

<400> SEQUENCE: 37

atgaagcttg gttggatcga ggtggccgca ttggcggctg cctcagtagt cagtgcc       57


<210> SEQ ID NO 38
<211> LENGTH: 19
<212> TYPE: PRT
<213> ORGANISM: Aspergillus oryzae

<400> SEQUENCE: 38

Met Lys Leu Gly Trp Ile Glu Val Ala Ala Leu Ala Ala Ala Ser Val
1               5                   10                  15

Val Ser Ala


<210> SEQ ID NO 39
<211> LENGTH: 42
<212> TYPE: DNA
<213> ORGANISM: Aspergillus oryzae

<400> SEQUENCE: 39
```

tgccggtgtt ggcccttgcc aaggatgatc tcgcgtactc cc 42

<210> SEQ ID NO 40
<211> LENGTH: 28
<212> TYPE: DNA
<213> ORGANISM: Aspergillus oryzae

<400> SEQUENCE: 40
gactagtctt actgggcctt aggcagcg 28

<210> SEQ ID NO 41
<211> LENGTH: 63
<212> TYPE: DNA
<213> ORGANISM: Humicola insolens

<400> SEQUENCE: 41
atgcgttcct cccccctcct ccgctccgcc gttgtggccg ccctgccggt gttggccctt 60
gcc 63

<210> SEQ ID NO 42
<211> LENGTH: 21
<212> TYPE: PRT
<213> ORGANISM: Humicola insolens

<400> SEQUENCE: 42

Met Arg Ser Ser Pro Leu Leu Arg Ser Ala Val Val Ala Ala Leu Pro
1 5 10 15

Val Leu Ala Leu Ala
20

<210> SEQ ID NO 43
<211> LENGTH: 30
<212> TYPE: DNA
<213> ORGANISM: Trichoderma reesei

<400> SEQUENCE: 43
acgcgtcgac cgaatgtagg attgttatcc 30

<210> SEQ ID NO 44
<211> LENGTH: 42
<212> TYPE: DNA
<213> ORGANISM: Trichoderma reesei

<400> SEQUENCE: 44
gggagtacgc gagatcatcc ttggcaaggg ccaacaccgg ca 42

<210> SEQ ID NO 45
<211> LENGTH: 1377
<212> TYPE: DNA
<213> ORGANISM: Trichoderma reesei

<400> SEQUENCE: 45
atggcgccct cagttacact gccgttgacc acggccatcc tggccattgc ccggctcgtc 60
gccgcccagc aaccgggtac cagcaccccc gaggtccatc ccaagttgac aacctacaag 120
tgtacaaagt ccgggggggtg cgtggcccag gacacctcgg tggtccttga ctggaactac 180
cgctggatgc acgacgcaaa ctacaactcg tgcaccgtca acggcggcgt caacaccacg 240
ctctgccctg acgaggcgac ctgtggcaag aactgcttca tcgagggcgt cgactacgcc 300
gcctcgggcg tcacgacctc gggcagcagc ctcaccatga accagtacat gcccagcagc 360
tctggcggct acagcagcgt ctctcctcgg ctgtatctcc tggactctga cggtgagtac 420

```
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgacccctc actcttgcac ggccacggcc    720
tgcgactctg ccggttgcgg cttcaacccc tatggcagcg gctacaaaag ctactacggc    780
cccggagata ccgttgacac ctccaagacc ttcaccatca tcacccagtt caacacggac    840
aacggctcgc cctcgggcaa ccttgtgagc atcacccgca agtaccagca aaacggcgtc    900
gacatcccca gcgcccagcc cggcggcgac accatctcgt cctgcccgtc cgcctcagcc    960
tacggcggcc tcgccaccat gggcaaggcc ctgagcagcg gcatggtgct cgtgttcagc   1020
atttggaacg acaacagcca gtacatgaac tggctcgaca gcggcaacgc cggcccctgc   1080
agcagcaccg agggcaaccc atccaacatc ctggccaaca accccaacac gcacgtcgtc   1140
ttctccaaca tccgctgggg agacattggg tctactacga actcgactgc gcccccgccc   1200
ccgcctgcgt ccagcacgac gttttcgact acacggagga gctcgacgac ttcgagcagc   1260
ccgagctgca cgcagactca ctgggggcag tgcggtggca ttgggtacag cgggtgcaag   1320
acgtgcacgt cgggcactac gtgccagtat agcaacgact actactcgca atgcctt      1377
```

```
<210> SEQ ID NO 46
<211> LENGTH: 459
<212> TYPE: PRT
<213> ORGANISM: Trichoderma reesei

<400> SEQUENCE: 46

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205
```

```
Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 47
<211> LENGTH: 1254
<212> TYPE: DNA
<213> ORGANISM: Trichoderma reesei

<400> SEQUENCE: 47

```
atgaacaagt ccgtggctcc attgctgctt gcagcgtcca tactatatgg cggcgccgtc      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg aggacgggat gactattttc cgcttacctg tcggatggca gtacctcgtc     480

aacaacaatt tgggcggcaa tcttgattcc acgagcattt ccaagtatga tcagcttgtt     540

caggggtgcc tgtctctggg cgcatactgc atcgtcgaca tccacaatta tgctcgatgg     600

aacggtggga tcattggtca gggcggccct actaatgctc aattcacgag cctttggtcg     660

cagttggcat caaagtacgc atctcagtcg agggtgtggt tcggcatcat gaatgagccc     720
```

```
cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactagc   1200

agtggtaact catggacgga cacatccttg gtcagctcgt gtctcgcaag aaag         1254
```

```
<210> SEQ ID NO 48
<211> LENGTH: 418
<212> TYPE: PRT
<213> ORGANISM: Trichoderma reesei

<400> SEQUENCE: 48

Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285
```

```
Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys


<210> SEQ ID NO 49
<211> LENGTH: 702
<212> TYPE: DNA
<213> ORGANISM: Trichoderma reesei

<400> SEQUENCE: 49

atgaagttcc ttcaagtcct ccctgccctc ataccggccg ccctggccca aaccagctgt      60

gaccagtggg caaccttcac tggcaacggc tacacagtca gcaacaacct ttggggagca     120

tcagccggct ctggatttgg ctgcgtgacg gcggtatcgc tcagcggcgg ggcctcctgg     180

cacgcagact ggcagtggtc cggcggccag aacaacgtca agtcgtacca gaactctcag     240

attgccattc cccagaagag gaccgtcaac agcatcagca gcatgcccac cactgccagc     300

tggagctaca gcgggagcaa catccgcgct aatgttgcgt atgacttgtt caccgcagcc     360

aacccgaatc atgtcacgta ctcgggagac tacgaactca tgatctggct tggcaaatac     420

ggcgatattg ggccgattgg gtcctcacag ggaacagtca acgtcggtgg ccagagctgg     480

acgctctact atggctacaa cggagccatg caagtctatt cctttgtggc ccagaccaac     540

actaccaact acagcggaga tgtcaagaac ttcttcaatt atctccgaga caataaagga     600

tacaacgctg caggccaata tgttcttagc taccaatttg gtaccgagcc cttcacgggc     660

agtggaactc tgaacgtcgc atcctggacc gcatctatca ac                        702


<210> SEQ ID NO 50
<211> LENGTH: 234
<212> TYPE: PRT
<213> ORGANISM: Trichoderma reesei

<400> SEQUENCE: 50

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80
```

```
Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 51
<211> LENGTH: 726
<212> TYPE: DNA
<213> ORGANISM: Trichoderma reesei

<400> SEQUENCE: 51

```
atgaaggcaa ctctggttct cggctccctc attgtaggcg ccgtttccgc gtacaaggcc     60

accaccacgc gctactacga tgggcaggag ggtgcttgcg gatgcggctc gagctccggc    120

gcattcccgt ggcagctcgg catcggcaac ggagtctaca cggctgccgg ctcccaggct    180

ctcttcgaca cggccggagc ttcatggtgc ggcgccggct gcggtaaatg ctaccagctc    240

acctcgacgg gccaggcgcc ctgctccagc tgcggcacgg gcggtgctgc tggccagagc    300

atcatcgtca tggtgaccaa cctgtgcccg aacaatggga acgcgcagtg gtgcccggtg    360

gtcggcggca ccaaccaata cggctacagc taccatttcg acatcatggc gcagaacgag    420

atctttggag acaatgtcgt cgtcgacttt gagcccattg cttgccccgg gcaggctgcc    480

tctgactggg ggacgtgcct ctgcgtggga cagcaagaga cggatcccac gcccgtcctc    540

ggcaacgaca cgggctcaac tcctcccggg agctcgccgc cagcgacatc gtcgagtccg    600

ccgtctggcg gcggccagca gacgctctat ggccagtgtg gaggtgccgg ctggacggga    660

cctacgacgt gccaggcccc agggacctgc aaggttcaga accagtggta ctcccagtgt    720

cttcct                                                               726
```

<210> SEQ ID NO 52
<211> LENGTH: 242
<212> TYPE: PRT
<213> ORGANISM: Trichoderma reesei

<400> SEQUENCE: 52

```
Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
```

```
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro


<210> SEQ ID NO 53
<211> LENGTH: 1371
<212> TYPE: DNA
<213> ORGANISM: Myceliophthora thermophila

<400> SEQUENCE: 53

atgggtcgcg gcgctgcttt cctaggcctc gcctcgctcc tcgtgggcgc ggccaaggcc      60

cagacgcccg gcgagggcga ggaggtgcac ccgcagatca cgacgtaccg ctgcaccaag     120

gcggacgggt gcgaggagaa gaccaactac atcgtgctgg acgccctatc gcacccggtc     180

caccaggtcg acaacccgta caactgcggc gactggggcc agaagcccaa cgagacggcc     240

tgcccggacc tcgagtcgtg cgccaggaac tgcatcatgg acccggtctc ggactacggc     300

cggcacggtg tctcgaccga cggcacctcg ctgcgcctca agcagctagt cggcggcaac     360

gtcgtcagcc cgcgcgtcta cctgctcgac gagaccaagg agcgctacga gatgctcaag     420

ctgaccggca acgagttcac ctttgacgtc gacgccacca agctgccctg cggcatgaac     480

agcgccctct acctctccga gatggacgcc accggcgccc ggagcgagct caacccgggc     540

ggcgccacct ttggcaccgg ctactgcgac gcccagtgct acgtcacccc cttcatcaac     600

ggcctcggca acatcgaggg caagggcgcg tgctgcaacg agatggatat ctgggaggcc     660

aacgcgcggg cgcagcacat cgcgccgcac ccgtgcagca aggcggggcc gtacctgtgc     720

gagggcgccg agtgcgagtt cgacggcgtg tgcgacaaga acggctgcgc ctggaacccg     780

taccgggtca acgtgacgga ctactacggc gagggcgccg agttcagggt ggacacgacc     840

cggcccttct cggtcgtcac gcagttccgc gccggcggcg acgcgggggg cggcaagctc     900

gagagcatct accggctctt cgtccaggac ggcagggtga ttgagtcgta cgtcgtcgac     960
```

```
aagcccggcc tgcccccgac ggaccgcatg acggacgagt tctgcgccgc caccggcgcc   1020

gcccgcttca cggagctcgg cgccatggag gccatgggcg acgccctgac gcgcggcatg   1080

gtcctcgccc tcagcatctg gtggagcgag ggcgacaaca tgaactggct cgactcgggc   1140

gaggccggcc cctgcgaccc ggacgagggc aacccgtcca acatcatccg cgtccagccc   1200

gacccggagg tcgtcttcag caacctgcgc tggggcgaga tcggctcaac ctacgagtcc   1260

gccgtcgacg ggcccgtcgg caagggcaag ggcaagggca agggcaaggc tcccgccggc   1320

gacggcaacg ggaaggagaa gagcaatggc aagcgcttca ggaggttctg a            1371
```

<210> SEQ ID NO 54
<211> LENGTH: 456
<212> TYPE: PRT
<213> ORGANISM: Myceliophthora thermophila

<400> SEQUENCE: 54

```
Met Gly Arg Gly Ala Ala Phe Leu Gly Leu Ala Ser Leu Leu Val Gly
1               5                   10                  15

Ala Ala Lys Ala Gln Thr Pro Gly Glu Gly Glu Glu Val His Pro Gln
            20                  25                  30

Ile Thr Thr Tyr Arg Cys Thr Lys Ala Asp Gly Cys Glu Glu Lys Thr
        35                  40                  45

Asn Tyr Ile Val Leu Asp Ala Leu Ser His Pro Val His Gln Val Asp
    50                  55                  60

Asn Pro Tyr Asn Cys Gly Asp Trp Gly Gln Lys Pro Asn Glu Thr Ala
65                  70                  75                  80

Cys Pro Asp Leu Glu Ser Cys Ala Arg Asn Cys Ile Met Asp Pro Val
                85                  90                  95

Ser Asp Tyr Gly Arg His Gly Val Ser Thr Asp Gly Thr Ser Leu Arg
            100                 105                 110

Leu Lys Gln Leu Val Gly Gly Asn Val Val Ser Pro Arg Val Tyr Leu
        115                 120                 125

Leu Asp Glu Thr Lys Glu Arg Tyr Glu Met Leu Lys Leu Thr Gly Asn
    130                 135                 140

Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
                165                 170                 175

Leu Asn Pro Gly Gly Ala Thr Phe Gly Thr Gly Tyr Cys Asp Ala Gln
            180                 185                 190

Cys Tyr Val Thr Pro Phe Ile Asn Gly Leu Gly Asn Ile Glu Gly Lys
        195                 200                 205

Gly Ala Cys Cys Asn Glu Met Asp Ile Trp Glu Ala Asn Ala Arg Ala
    210                 215                 220

Gln His Ile Ala Pro His Pro Cys Ser Lys Ala Gly Pro Tyr Leu Cys
225                 230                 235                 240

Glu Gly Ala Glu Cys Glu Phe Asp Gly Val Cys Asp Lys Asn Gly Cys
                245                 250                 255

Ala Trp Asn Pro Tyr Arg Val Asn Val Thr Asp Tyr Tyr Gly Glu Gly
            260                 265                 270

Ala Glu Phe Arg Val Asp Thr Thr Arg Pro Phe Ser Val Val Thr Gln
        275                 280                 285

Phe Arg Ala Gly Gly Asp Ala Gly Gly Gly Lys Leu Glu Ser Ile Tyr
    290                 295                 300

Arg Leu Phe Val Gln Asp Gly Arg Val Ile Glu Ser Tyr Val Val Asp
```

```
305                 310                 315                 320

Lys Pro Gly Leu Pro Pro Thr Asp Arg Met Thr Asp Glu Phe Cys Ala
                325                 330                 335

Ala Thr Gly Ala Ala Arg Phe Thr Glu Leu Gly Ala Met Glu Ala Met
            340                 345                 350

Gly Asp Ala Leu Thr Arg Gly Met Val Leu Ala Leu Ser Ile Trp Trp
        355                 360                 365

Ser Glu Gly Asp Asn Met Asn Trp Leu Asp Ser Gly Glu Ala Gly Pro
    370                 375                 380

Cys Asp Pro Asp Glu Gly Asn Pro Ser Asn Ile Ile Arg Val Gln Pro
385                 390                 395                 400

Asp Pro Glu Val Val Phe Ser Asn Leu Arg Trp Gly Glu Ile Gly Ser
                405                 410                 415

Thr Tyr Glu Ser Ala Val Asp Gly Pro Val Gly Lys Gly Lys Gly Lys
            420                 425                 430

Gly Lys Gly Lys Ala Pro Ala Gly Asp Gly Asn Gly Lys Glu Lys Ser
        435                 440                 445

Asn Gly Lys Arg Phe Arg Arg Phe
    450                 455


<210> SEQ ID NO 55
<211> LENGTH: 744
<212> TYPE: DNA
<213> ORGANISM: Chrysosoporium lucknowense

<400> SEQUENCE: 55

atgcagccgt ttctgctctt gttcctctcg tcggtcacgg cggcgagccc cctgacggcg      60

ctcgacaagc ggcagcaggc gacgttgtgc gagcagtacg gctactggtc gggcaacggt     120

tacgaggtca acaacaacaa ctggggcaag gattcggcct cgggcggcca tcagtgcacc     180

tacgtcgaca gcagcagctc cagcggcgtc gcctggcaca cgacctggca gtgggaagga     240

ggccagaacc aggtcaagag cttcgccaac tgcggcctgc aggtgcccaa gggcaggacc     300

atctcgtcca tcagcaacct gcagacctcc atctcgtggt cctacagcaa caccaacatc     360

cgcgccaacg tggcctacga cctcttcacc gcggcagacc cgaaccacgc gaccagcagc     420

ggcgactacg agctcatgat ctggctggcg agattcggcg acgtctaccc catcggctcg     480

tcccagggcc acgtcaacgt ggccggccag gactgggagc tgtggacggg cttcaacggc     540

aacatgcggg tctacagctt cgtagcgccc agcccccgca acagcttcag cgccaacgtc     600

aaggacttct tcaactatct ccagtccaac cagggcttcc cggccagcag ccaatacctt     660

ctcatcttcc aggcgggcac cgagcccttc accggcggcg agaccaccct taccgtcaac     720

aactactctg caagggttgc ttaa                                            744


<210> SEQ ID NO 56
<211> LENGTH: 247
<212> TYPE: PRT
<213> ORGANISM: Chrysosoporium lucknowense

<400> SEQUENCE: 56

Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
            20                  25                  30

Tyr Gly Tyr Trp Ser Gly Asn Gly Tyr Glu Val Asn Asn Asn Asn Trp
        35                  40                  45
```

```
Gly Lys Asp Ser Ala Ser Gly Gly His Gln Cys Thr Tyr Val Asp Ser
    50                  55                  60

Ser Ser Ser Ser Gly Val Ala Trp His Thr Thr Trp Gln Trp Glu Gly
65                  70                  75                  80

Gly Gln Asn Gln Val Lys Ser Phe Ala Asn Cys Gly Leu Gln Val Pro
                85                  90                  95

Lys Gly Arg Thr Ile Ser Ser Ile Ser Asn Leu Gln Thr Ser Ile Ser
            100                 105                 110

Trp Ser Tyr Ser Asn Thr Asn Ile Arg Ala Asn Val Ala Tyr Asp Leu
        115                 120                 125

Phe Thr Ala Ala Asp Pro Asn His Ala Thr Ser Ser Gly Asp Tyr Glu
    130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
        195                 200                 205

Ser Asn Gln Gly Phe Pro Ala Ser Ser Gln Tyr Leu Leu Ile Phe Gln
    210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245
```

<210> SEQ ID NO 57
<211> LENGTH: 678
<212> TYPE: DNA
<213> ORGANISM: Chrysosoporium lucknowense

<400> SEQUENCE: 57

```
atgcatctct ccgccaccac cgggttcctc gccctcccgg ccctggccct ggcccagctc      60

tcgggcagcg gccagacgac ccggtactgg gactgctgca agccgagctg cgcctggccc     120

ggcaagggcc cctcgtctcc ggtgcaggcc tgcgacaaga acgacaaccc gctcaacgac     180

ggcggctcca cccggtccgg ctgcgacgcg ggcggcagcg cctacatgtg ctcctcccag     240

agcccctggg ccgtcagcga cgagctgtcg tacggctggg cggccgtcaa gctcgccggc     300

agctccgagt cgcagtggtg ctgcgcctgc tacgagctga ccttcaccag cgggccggtc     360

gcgggcaaga agatgattgt gcaggcgacc aacaccggtg gcgacctggg cgacaaccac     420

tttgacctgg ccatccccgg tggcggtgtc ggtattttca acgcctgcac cgaccagtac     480

ggcgctcccc cgaacggctg gggcgaccgc tacggcggca tccattccaa ggaagagtgc     540

gaatccttcc cggaggccct caagcccggc tgcaactggc gcttcgactg gttccaaaac     600

gccgacaacc cgtcggtcac cttccaggag gtggcctgcc cgtcggagct cacgtccaag     660

agcggctgct cccgttaa                                                   678
```

<210> SEQ ID NO 58
<211> LENGTH: 225
<212> TYPE: PRT
<213> ORGANISM: Chrysosoporium lucknowense

<400> SEQUENCE: 58

```
Met His Leu Ser Ala Thr Thr Gly Phe Leu Ala Leu Pro Ala Leu Ala
```

```
1               5                   10                  15

Leu Ala Gln Leu Ser Gly Ser Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225


<210> SEQ ID NO 59
<211> LENGTH: 1542
<212> TYPE: DNA
<213> ORGANISM: Trichoderma reesei

<400> SEQUENCE: 59

atgtatcgga agttggccgt catctcggcc ttcttggcca cagctcgtgc tcagtcggcc      60

tgcactctcc aatcggagac tcacccgcct ctgacatggc agaaatgctc gtctggtggc     120

acgtgcactc aacagacagg ctccgtggtc atcgacgcca actggcgctg gactcacgct     180

acgaacagca gcacgaactg ctacgatggc aacacttgga gctcgaccct atgtcctgac     240

aacgagacct gcgcgaagaa ctgctgtctg gacggtgccg cctacgcgtc cacgtacgga     300

gttaccacga gcggtaacag cctctccatt ggctttgtca cccagtctgc gcagaagaac     360

gttggcgctc gcctttacct tatggcgagc gacacgacct accaggaatt caccctgctt     420

ggcaacgagt tctctttcga tgttgatgtt tcgcagctgc cgtgcggctt gaacggagct     480

ctctacttcg tgtccatgga cgcggatggt ggcgtgagca agtatcccac caacaccgct     540

ggcgccaagt acggcacggg gtactgtgac agccagtgtc cccgcgatct gaagttcatc     600

aatggccagg ccaacgttga gggctgggag ccgtcatcca acaacgcgaa cacgggcatt     660

ggaggacacg gaagctgctg ctctgagatg gatatctggg aggccaactc catctccgag     720

gctcttaccc cccacccttg cacgactgtc ggccaggaga tctgcgaggg tgatgggtgc     780

ggcggaactt actccgataa cagatatggc ggcacttgcg atcccgatgg ctgcgactgg     840
```

```
aacccatacc gcctgggcaa caccagcttc tacggccctg gctcaagctt taccctcgat    900

accaccaaga aattgaccgt tgtcacccag ttcgagacgt cgggtgccat caaccgatac    960

tatgtccaga atggcgtcac tttccagcag cccaacgccg agcttggtag ttactctggc   1020

aacgagctca acgatgatta ctgcacagct gaggaggcag aattcggcgg atcctctttc   1080

tcagacaagg gcggcctgac tcagttcaag aaggctacct ctggcggcat ggttctggtc   1140

atgagtctgt gggatgatta ctacgccaac atgctgtggc tggactccac ctacccgaca   1200

aacgagacct cctccacacc cggtgccgtg cgcggaagct gctccaccag ctccggtgtc   1260

cctgctcagg tcgaatctca gtctcccaac gccaaggtca ccttctccaa catcaagttc   1320

ggacccattg gcagcaccgg caaccctagc ggcggcaacc ctcccggcgg aaacccgcct   1380

ggcaccacca ccacccgccg cccagccact accactggaa gctctcccgg acctacccag   1440

tctcactacg gccagtgcgg cggtattggc tacagcggcc ccacggtctg cgccagcggc   1500

acaacttgcc aggtcctgaa cccttactac tctcagtgcc tg                      1542
```

```
<210> SEQ ID NO 60
<211> LENGTH: 514
<212> TYPE: PRT
<213> ORGANISM: Trichoderma reesei

<400> SEQUENCE: 60

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255
```

```
Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu
```

<210> SEQ ID NO 61
<211> LENGTH: 1413
<212> TYPE: DNA
<213> ORGANISM: Trichoderma reesei

<400> SEQUENCE: 61

```
atgattgtcg gcattctcac cacgctggct acgctggcca cactcgcagc tagtgtgcct     60

ctagaggagc ggcaagcttg ctcaagcgtc tggggccaat gtggtggcca gaattggtcg    120

ggtccgactt gctgtgcttc cggaagcaca tgcgtctact ccaacgacta ttactcccag    180

tgtcttcccg gcgctgcaag ctcaagctcg tccacgcgcg ccgcgtcgac gacttctcga    240

gtatccccca caacatcccg gtcgagctcc gcgacgcctc cacctggttc tactactacc    300

agagtacctc cagtcggatc gggaaccgct acgtattcag gcaacccttt tgttggggtc    360

actccttggg ccaatgcata ttacgcctct gaagttagca gcctcgctat tcctagcttg    420

actggagcca tggccactgc tgcagcagct gtcgcaaagg ttccctcttt tatgtggcta    480

gatactcttg acaagacccc tctcatggag caaaccttgg ccgacatccg caccgccaac    540

aagaatggcg gtaactatgc cggacagttt gtggtgtatg acttgccgga tcgcgattgc    600

gctgcccttg cctcgaatgg cgaatactct attgccgatg gtggcgtcgc caaatataag    660
```

```
aactatatcg acaccattcg tcaaattgtc gtggaatatt ccgatatccg gaccctcctg    720

gttattgagc ctgactctct tgccaacctg gtgaccaacc tcggtactcc aaagtgtgcc    780

aatgctcagt cagcctacct tgagtgcatc aactacgccg tcacacagct gaaccttcca    840

aatgttgcga tgtatttgga cgctggccat gcaggatggc ttggctggcc ggcaaaccaa    900

gacccggccg ctcagctatt tgcaaatgtt tacaagaatg catcgtctcc gagagctctt    960

cgcggattgg caaccaatgt cgccaactac aacgggtgga acattaccag ccccccatcg   1020

tacacgcaag gcaacgctgt ctacaacgag aagctgtaca tccacgctat tggacctctt   1080

cttgccaatc acggctggtc caacgccttc ttcatcactg atcaaggtcg atcgggaaag   1140

cagcctaccg gacagcaaca gtggggagac tggtgcaatg tgatcggcac cggatttggt   1200

attcgcccat ccgcaaacac tggggactcg ttgctggatt cgtttgtctg ggtcaagcca   1260

ggcggcgagt gtgacggcac cagcgacagc agtgcgccac gatttgactc ccactgtgcg   1320

ctcccagatg ccttgcaacc ggcgcctcaa gctggtgctt ggttccaagc ctactttgtg   1380

cagcttctca caaacgcaaa cccatcgttc ctg                                1413


<210> SEQ ID NO 62
<211> LENGTH: 471
<212> TYPE: PRT
<213> ORGANISM: Trichoderma reesei

<400> SEQUENCE: 62

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
```

```
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470
```

<210> SEQ ID NO 63
<211> LENGTH: 1648
<212> TYPE: DNA
<213> ORGANISM: Chrysosoporium lucknowense
<220> FEATURE:
<221> NAME/KEY: misc_feature
<222> LOCATION: (1162)..(1162)
<223> OTHER INFORMATION: N= A,C,G, OR T

<400> SEQUENCE: 63

```
atgtacgcca agttcgcgac cctcgccgcc cttgtggctg gcgccgctgc tcagaacgcc     60

tgcactctga ccgctgagaa ccacccctcg ctgacgtggt ccaagtgcac gtctggcggc    120

agctgcacca gcgtccaggg ttccatcacc atcgacgcca actggcggtg gactcaccgg    180

accgatagcg ccaccaactg ctacgagggc aacaagtggg atacttcgta ctgcagcgat    240

ggtccttctt gcgcctccaa gtgctgcatc gacggcgctg actactcgag cacctatggc    300

atcaccacga gcggtaactc cctgaacctc aagttcgtca ccaagggcca gtactcgacc    360

aacatcggct cgcgtaccta cctgatggag agcgacacca agtaccagag taagttcctc    420

tcgcacccgg ccgccgggag atgatggcgc ccagcccgct gacgcgaatg acacagtgtt    480

ccagctcctc ggcaacgagt tcaccttcga tgtcgacgtc tccaacctcg gctgcggcct    540

caatggcgcc ctctacttcg tgtccatgga tgccgatggt ggcatgtcca agtactcggg    600

caacaaggca ggtgccaagt acggtaccgg ctactgtgat tctcagtgcc cccgcgacct    660

caagttcatc aacggcgagg ccaacgtaga gaactggcag agctcgacca acgatgccaa    720
```

```
cgccggcacg ggcaagtacg gcagctgctg ctccgagatg gacgtctggg aggccaacaa    780
catggccgcc gccttcactc cccacccttg caccgtgatc ggccagtcgc gctgcgaggg    840
cgactcgtgc ggcggtacct acagcaccga ccgctatgcc ggcatctgcg accccgacgg    900
atgcgacttc aactcgtacc gccagggcaa caagaccttc tacggcaagg gcatgacggt    960
cgacacgacc aagaagatca cggtcgtcac ccagttcctc aagaactcgg ccggcgagct   1020
ctccgagatc aagcggttct acgtccagaa cggcaaggtc atccccaact ccgagtccac   1080
catcccgggc gtcgagggca actccatcac ccaggactgg tgcgaccgcc agaaggccgc   1140
cttcggcgac gtgaccgact tncaggacaa gggcggcatg gtccagatgg gcaaggccct   1200
cgcggggccc atggtcctcg tcatgtccat ctgggacgac cacgccgtca acatgctctg   1260
gctcgactcc acctggccca tcgacggcgc cggcaagccg ggcgccgagc gcggtgcctg   1320
ccccaccacc tcgggcgtcc ccgctgaggt cgaggccgag gcccccaact ccaacgtcat   1380
cttctccaac atccgcttcg gccccatcgg ctccaccgtc tccggcctgc ccgacggcgg   1440
cagcggcaac cccaacccgc ccgtcagctc gtccaccccg gtcccctcct cgtccaccac   1500
atcctccggt tcctccggcc cgactggcgg cacgggtgtc gctaagcact atgagcaatg   1560
cggaggaatc gggttcactg gccctaccca gtgcgagagc ccctacactt gcaccaagct   1620
gaatgactgg tactcgcagt gcctgtaa                                       1648
```

```
<210> SEQ ID NO 64
<211> LENGTH: 526
<212> TYPE: PRT
<213> ORGANISM: Chrysosoporium lucknowense
<220> FEATURE:
<221> NAME/KEY: MISC_FEATURE
<222> LOCATION: (365)..(365)
<223> OTHER INFORMATION: X= ANY AMINO ACID

<400> SEQUENCE: 64

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190
```

```
Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Trp Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Xaa Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525
```

<210> SEQ ID NO 65
<211> LENGTH: 1353
<212> TYPE: DNA
<213> ORGANISM: Myceliophthora thermophila

<400> SEQUENCE: 65

```
atgaagcagt acctccagta cctcgcggcg accctgcccc tggtgggcct ggccacggcc      60

cagcaggcgg gtaacctgca gaccgagact caccccaggc tcacttggtc caagtgcacg     120

gccccgggat cctgccaaca ggtcaacggc gaggtcgtca tcgactccaa ctggcgctgg     180

gtgcacgacg agaacgcgca gaactgctac gacggcaacc agtggaccaa cgcttgcagc     240

tctgccaccg actgcgccga gaattgcgcg ctcgagggtg ccgactacca gggcacctat     300
```

```
ggcgcctcga ccagcggcaa tgccctgacg ctcaccttcg tcactaagca cgagtacggc    360

accaacattg gctcgcgcct ctacctcatg aacggcgcga acaagtacca gatgttcacc    420

ctcaagggca acgagctggc cttcgacgtc gacctctcgg ccgtcgagtg cggcctcaac    480

agcgccctct acttcgtggc catggaggag gatggcggtg tgtcgagcta cccgaccaac    540

acggccggtg ctaagttcgg cactgggtac tgcgacgccc aatgcgcacg cgacctcaag    600

ttcgtcggcg gcaagggcaa catcgagggc tggaagccgt ccaccaacga tgccaatgcc    660

ggtgtcggtc cttatggcgg gtgctgcgct gagatcgacg tctgggagtc gaacaagtat    720

gctttcgctt tcaccccgca cggttgcgag aaccctaaat accacgtctg cgagaccacc    780

aactgcggtg gcacctactc cgaggaccgc ttcgctggtg actgcgatgc caacggctgc    840

gactacaacc cctaccgcat gggcaaccag gacttctacg gtcccggctt gacggtcgat    900

accagcaaga agttcaccgt cgtcagccag ttcgaggaga acaagctcac ccagttcttc    960

gtccaggacg gcaagaagat tgagatcccc ggccccaagg tcgagggcat cgatgcggac   1020

agcgccgcta tcacccctga gctgtgcagt gccctgttca aggccttcga tgaccgtgac   1080

cgcttctcgg aggttggcgg cttcgatgcc atcaacacgg ccctcagcac tcccatggtc   1140

ctcgtcatgt ccatctggga tgatcactac gccaatatgc tctggctcga ctcgagctac   1200

ccccctgaga aggctggcca gcctggcggt gaccgtggcc cgtgtcctca ggactctggc   1260

gtcccggccg acgttgaggc tcagtaccct aatgccaagg tcatctggtc caacatccgc   1320

ttcggcccca tcggctcgac tgtcaacgtc taa                                1353
```

<210> SEQ ID NO 66
<211> LENGTH: 450
<212> TYPE: PRT
<213> ORGANISM: Myceliophthora thermophila

<400> SEQUENCE: 66

```
Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Arg Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
    50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
    130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Thr Asn Thr Ala Gly Ala Lys Phe Gly Thr Gly Tyr Cys Asp
            180                 185                 190
```

```
Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
    210                 215                 220

Tyr Gly Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255

Cys Glu Thr Thr Asn Cys Gly Gly Thr Tyr Ser Glu Asp Arg Phe Ala
            260                 265                 270

Gly Asp Cys Asp Ala Asn Gly Cys Asp Tyr Asn Pro Tyr Arg Met Gly
        275                 280                 285

Asn Gln Asp Phe Tyr Gly Pro Gly Leu Thr Val Asp Thr Ser Lys Lys
    290                 295                 300

Phe Thr Val Val Ser Gln Phe Glu Glu Asn Lys Leu Thr Gln Phe Phe
305                 310                 315                 320

Val Gln Asp Gly Lys Lys Ile Glu Ile Pro Gly Pro Lys Val Glu Gly
                325                 330                 335

Ile Asp Ala Asp Ser Ala Ala Ile Thr Pro Glu Leu Cys Ser Ala Leu
            340                 345                 350

Phe Lys Ala Phe Asp Asp Arg Asp Arg Phe Ser Glu Val Gly Gly Phe
        355                 360                 365

Asp Ala Ile Asn Thr Ala Leu Ser Thr Pro Met Val Leu Val Met Ser
    370                 375                 380

Ile Trp Asp Asp His Tyr Ala Asn Met Leu Trp Leu Asp Ser Ser Tyr
385                 390                 395                 400

Pro Pro Glu Lys Ala Gly Gln Pro Gly Gly Asp Arg Gly Pro Cys Pro
                405                 410                 415

Gln Asp Ser Gly Val Pro Ala Asp Val Glu Ala Gln Tyr Pro Asn Ala
            420                 425                 430

Lys Val Ile Trp Ser Asn Ile Arg Phe Gly Pro Ile Gly Ser Thr Val
        435                 440                 445

Asn Val
    450
```

<210> SEQ ID NO 67
<211> LENGTH: 1446
<212> TYPE: DNA
<213> ORGANISM: Thielavia terrestris

<400> SEQUENCE: 67

```
atggctcaga agctccttct cgccgccgcc cttgcggcca gcgccctcgc tgctcccgtc     60

gtcgaggagc gccagaactg cggttccgtc tggagccaat gcggcggcat tggctggtcc    120

ggcgcgacct gctgcgcttc gggcaatacc tgcgttgagc tgaacccgta ctactcgcag    180

tgcctgccca acagccaggt gactacctcg accagcaaga ccacctccac caccaccagg    240

agcagcacca ccagccacag cagcggtccc accagcacga gcaccaccac caccagcagt    300

cccgtggtca ctaccccgcc gagtacctcc atccccggcg gtgcctcgtc aacggccagc    360

tggtccggca acccgttctc gggcgtgcag atgtgggcca acgactacta cgcctccgag    420

gtctcgtcgc tggccatccc cagcatgacg ggcgccatgg ccaccaaggc ggccgaggtg    480

gccaaggtgc ccagcttcca gtggcttgac cgcaacgtca ccatcgacac gctgttcgcc    540

cacacgctgt cgcagatccg cgcggccaac cagaaaggcg ccaacccgcc ctacgcgggc    600
```

```
atcttcgtgg tctacgacct tccggaccgc gactgcgccg ccgccgcgtc caacggcgag    660

ttctccatcg cgaacaacgg ggcggccaac tacaagacgt acatcgacgc gatccggagc    720

ctcgtcatcc agtactcaga catccgcatc atcttcgtca tcgagcccga ctcgctggcc    780

aacatggtga ccaacctgaa cgtggccaag tgcgccaacg ccgagtcgac ctacaaggag    840

ttgaccgtct acgcgctgca gcagctgaac ctgcccaacg tggccatgta cctggacgcc    900

ggccacgccg gctggctcgg ctggcccgcc aacatccagc cggccgccaa cctcttcgcc    960

gagatctaca cgagcgccgg caagccggcc gccgtgcgcg gcctcgccac caacgtggcc   1020

aactacaacg gctggagcct ggccacgccg ccctcgtaca cccagggcga ccccaactac   1080

gacgagagcc actacgtcca ggccctcgcc ccgctgctca ccgccaacgg cttccccgcc   1140

cacttcatca ccgacaccgg ccgcaacggc aagcagccga ccggacaacg gcaatgggga   1200

gactggtgca acgttatcgg aactggcttc ggcgtgcgcc cgacgacaaa caccggcctc   1260

gacatcgagg acgccttcgt ctgggtcaag cccggcggcg agtgcgacgg cacgagcaac   1320

acgacctctc cccgctacga ctaccactgc ggcctgtcgg acgcgctgca gcctgctccg   1380

gaggccggca cttggttcca ggcctacttc gagcagctcc tgaccaacgc caacccgccc   1440

ttttaa                                                              1446
```

```
<210> SEQ ID NO 68
<211> LENGTH: 481
<212> TYPE: PRT
<213> ORGANISM: Thielavia terrestris

<400> SEQUENCE: 68

Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ala Ser Asn Gly Glu Phe Ser Ile Ala
    210                 215                 220
```

```
Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
        435                 440                 445

His Cys Gly Leu Ser Asp Ala Leu Gln Pro Ala Pro Glu Ala Gly Thr
    450                 455                 460

Trp Phe Gln Ala Tyr Phe Glu Gln Leu Leu Thr Asn Ala Asn Pro Pro
465                 470                 475                 480

Phe
```

<210> SEQ ID NO 69
<211> LENGTH: 2586
<212> TYPE: DNA
<213> ORGANISM: Aspergillus oryzae

<400> SEQUENCE: 69

```
atgaagcttg gttggatcga ggtggccgca ttggcggctg cctcagtagt cagtgccaag      60

gatgatctcg cgtactcccc tcctttctac ccttccccat gggcagatgg tcagggtgaa     120

tgggcggaag tatacaaacg cgctgtagac atagtttccc agatgacgtt gacagagaaa     180

gtcaacttaa cgactggaac aggatggcaa ctagagaggt gtgttggaca aactggcagt     240

gttcccagac tcaacatccc cagcttgtgt ttgcaggata gtcctcttgg tattcgtttc     300

tcggactaca attcagcttt ccctgcgggt gttaatgtcg ctgccacctg ggacaagacg     360

ctcgcctacc ttcgtggtca ggcaatgggt gaggagttca gtgataaggg tattgacgtt     420

cagctgggtc ctgctgctgg ccctctcggt gctcatccgg atggcggtag aaactgggaa     480

ggtttctcac cagatccagc cctcaccggt gtactttttg cggagacgat taagggtatt     540

caagatgctg gtgtcattgc gacagctaag cattatatca tgaacgaaca agagcatttc     600

cgccaacaac ccgaggctgc gggttacgga ttcaacgtaa gcgacagttt gagttccaac     660
```

```
gttgatgaca agactatgca tgaattgtac ctctggccct tcgcggatgc agtacgcgct    720

ggagtcggtg ctgtcatgtg ctcttacaac caaatcaaca acagctacgg ttgcgagaat    780

agcgaaactc tgaacaagct tttgaaggcg gagcttggtt tccaaggctt cgtcatgagt    840

gattggaccg ctcatcacag cggcgtaggc gctgctttag caggtctgga tatgtcgatg    900

cccggtgatg ttaccttcga tagtggtacg tctttctggg gtgcaaactt gacggtcggt    960

gtccttaacg gtacaatccc ccaatggcgt gttgatgaca tggctgtccg tatcatggcc   1020

gcttattaca aggttggccg cgacaccaaa tacacccctc ccaacttcag ctcgtggacc   1080

agggacgaat atggtttcgc gcataaccat gtttcggaag gtgcttacga gagggtcaac   1140

gaattcgtgg acgtgcaacg cgatcatgcc gacctaatcc gtcgcatcgg cgcgcagagc   1200

actgttctgc tgaagaacaa gggtgccttg cccttgagcc gcaaggaaaa gctggtcgcc   1260

cttctgggag aggatgcggg ttccaactcg tggggcgcta acggctgtga tgaccgtggt   1320

tgcgataacg gtacccttgc catggcctgg ggtagcggta ctgcgaattt cccatacctc   1380

gtgacaccag agcaggcgat tcagaacgaa gttcttcagg gccgtggtaa tgtcttcgcc   1440

gtgaccgaca gttgggcgct cgacaagatc gctgcggctg cccgccaggc cagcgtatct   1500

ctcgtgttcg tcaactccga ctcaggagaa ggctatctta gtgtggatgg aaatgagggc   1560

gatcgtaaca acatcactct gtggaagaac ggcgacaatg tggtcaagac cgcagcgaat   1620

aactgtaaca acaccgttgt catcatccac tccgtcggac cagttttgat cgatgaatgg   1680

tatgaccacc ccaatgtcac tggtattctc tgggctggtc tgccaggcca ggagtctggt   1740

aactccattg ccgatgtgct gtacggtcgt gtcaaccctg gcgccaagtc tcctttcact   1800

tggggcaaga cccgggagtc gtatggttct cccttggtca aggatgccaa caatggcaac   1860

ggagcgcccc agtctgattt cacccagggt gttttcatcg attaccgcca tttcgataag   1920

ttcaatgaga cccctatcta cgagtttggc tacggcttga gctacaccac cttcgagctc   1980

tccgacctcc atgttcagcc cctgaacgcg tcccgataca ctcccaccag tggcatgact   2040

gaagctgcaa agaactttgg tgaaattggc gatgcgtcgg agtacgtgta tccggagggg   2100

ctggaaagga tccatgagtt tatctatccc tggatcaact ctaccgacct gaaggcatcg   2160

tctgacgatt ctaactacgg ctgggaagac tccaagtata ttcccgaagg cgccacggat   2220

gggtctgccc agccccgttt gcccgctagt ggtggtgccg gaggaaaccc cggtctgtac   2280

gaggatcttt tccgcgtctc tgtgaaggtc aagaacacgg gcaatgtcgc cggtgatgaa   2340

gttcctcagc tgtacgtttc cctaggcggc ccgaatgagc ccaaggtggt actgcgcaag   2400

tttgagcgta ttcacttggc cccttcgcag gaggccgtgt ggacaacgac ccttacccgt   2460

cgtgaccttg caaactggga cgtttcggct caggactgga ccgtcactcc ttaccccaag   2520

acgatctacg ttggaaactc ctcacggaaa ctgccgctcc aggcctcgct gcctaaggcc   2580

cagtaa                                                              2586
```

<210> SEQ ID NO 70
<211> LENGTH: 861
<212> TYPE: PRT
<213> ORGANISM: Aspergillus oryzae

<400> SEQUENCE: 70

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30
```

```
Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460
```

```
Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Ala Arg Gln
                485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860
```

<210> SEQ ID NO 71
<211> LENGTH: 3060
<212> TYPE: DNA

<213> ORGANISM: Aspergillus fumigatus

<400> SEQUENCE: 71

```
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctataccccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt actttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
```

```
gctccccagg atgatttcaa cgagggcgtc ttcattgact accgtcactt tgacaagcgc   2340

aatgagaccc ccatttatga gtttggccat ggcttgagct acaccacctt tggttactct   2400

caccttcggg ttcaggccct caatagttcg agttcggcat atgtcccgac tagcggagag   2460

accaagcctg cgccaaccta tggtgagatc ggtagtgccg ccgactacct gtatcccgag   2520

ggtctcaaaa gaattaccaa gtttatttac ccttggctca actcgaccga cctcgaggat   2580

tcttctgacg acccgaacta cggctgggag gactcggagt acattcccga aggcgctagg   2640

gatgggtctc ctcaacccct cctgaaggct ggcggcgctc ctggtggtaa ccctaccctt   2700

tatcaggatc ttgttagggt gtcggccacc ataaccaaca ctggtaacgt cgccggttat   2760

gaagtccctc aattggtgag tgacccgcat gttccttgcg ttgcaatttg gctaactcgc   2820

ttctagtatg tttcactggg cggaccgaac gagcctcggg tcgttctgcg caagttcgac   2880

cgaatcttcc tggctcctgg ggagcaaaag gtttggacca cgactcttaa ccgtcgtgat   2940

ctcgccaatt gggatgtgga ggctcaggac tgggtcatca caaagtaccc caagaaagtg   3000

cacgtcggca gctcctcgcg taagctgcct ctgagagcgc ctctgccccg tgtctactag   3060
```

<210> SEQ ID NO 72
<211> LENGTH: 863
<212> TYPE: PRT
<213> ORGANISM: Aspergillus fumigatus

<400> SEQUENCE: 72

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
```

-continued

```
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670
```

```
Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860


<210> SEQ ID NO 73
<211> LENGTH: 2800
<212> TYPE: DNA
<213> ORGANISM: Penicillium brasilianum

<400> SEQUENCE: 73

tgaaaatgca gggttctaca atctttctgg ctttcgcctc atgggcgagc caggttgctg      60

ccattgcgca gcccatacag aagcacgagg tttgttttat cttgctcatg gacgtgcttt     120

gacttgacta attgttttac atacagcccg gatttctgca cgggccccaa gccatagaat     180

cgttctcaga accgttctac ccgtcgccct ggatgaatcc tcacgccgag ggctgggagg     240

ccgcatatca gaaagctcaa gattttgtct cgcaactcac tatcttggag aaaataaatc     300

tgaccaccgg tgttgggtaa gtctctccga ctgcttctgg gtcacggtgc gacgagccac     360

tgactttttg aagctgggaa aatgggccgt gtgtaggaaa cactggatca attcctcgtc     420

tcggattcaa aggattttgt acccaggatt caccacaggg tgttcggttc gcagattatt     480

cctccgcttt cacatctagc caaatggccg ccgcaacatt tgaccgctca attctttatc     540

aacgaggcca agccatggca caggaacaca aggctaaggg tatcacaatt caattgggcc     600

ctgttgccgg ccctctcggt cgcatccccg agggcggccg caactgggaa ggattctccc     660

ctgatcctgt cttgactggt atagccatgg ctgagacaat taagggcatg caggatactg     720

gagtgattgc ttgcgctaaa cattatattg gaaacgagca ggagcacttc cgtcaagtgg     780

gtgaagctgc gggtcacgga tacactattt ccgatactat ttcatctaat attgacgacc     840

gtgctatgca tgagctatac ttgtggccat ttgctgatgc cgttcgcgct ggtgtgggtt     900

ctttcatgtg ctcatactct cagatcaaca actcctacgg atgccaaaac agtcagaccc     960

tcaacaagct cctcaagagc gaattgggct tccaaggctt tgtcatgagc gattggggtg    1020

cccatcactc tggagtgtca tcggcgctag ctggacttga tatgagcatg ccgggtgata    1080
```

```
ccgaatttga ttctggcttg agcttctggg gctctaacct caccattgca attctgaacg   1140

gcacggttcc cgaatggcgc ctggatgaca tggcgatgcg aattatggct gcatacttca   1200

aagttggcct tactattgag gatcaaccag atgtcaactt caatgcctgg acccatgaca   1260

cctacggata taaatacgct tatagcaagg aagattacga gcaggtcaac tggcatgtcg   1320

atgttcgcag cgaccacaat aagctcattc gcgagactgc cgcgaagggt acagttctgc   1380

tgaagaacaa ctttcatgct ctccctctga agcagcccag gttcgtggcc gtcgttggtc   1440

aggatgccgg gccaaacccc aagggcccta acggctgcgc agaccgagga tgcgaccaag   1500

gcactctcgc aatgggatgg ggctcagggt ctaccgaatt cccttacctg gtcactcctg   1560

acactgctat tcagtcaaag gtcctcgaat acgggggtcg atacgagagt atttttgata   1620

actatgacga caatgctatc ttgtcgcttg tctcacagcc tgatgcaacc tgtatcgttt   1680

ttgcaaatgc cgattccggt gaaggctaca tcactgtcga caacaactgg ggtgaccgca   1740

acaatctgac cctctggcaa aatgccgatc aagtgattag cactgtcagc tcgcgatgca   1800

acaacacaat cgttgttctc cactctgtcg gaccagtgtt gctaaatggt atatatgagc   1860

acccgaacat cacagctatt gtctgggcag ggatgccagg cgaagaatct ggcaatgctc   1920

tcgtggatat tctttggggc aatgttaacc ctgccggtcg cactccgttc acctgggcca   1980

aaagtcgaga ggactatggc actgatataa tgtacgagcc caacaacggc cagcgtgcgc   2040

ctcagcagga tttcaccgag agcatctacc tcgactaccg ccatttcgac aaagctggta   2100

tcgagccaat ttacgagttt ggattcggcc tctcctatac caccttcgaa tactctgacc   2160

tccgtgttgt gaagaagtat gttcaaccat acagtcccac gaccggcacc ggtgctcaag   2220

caccttccat cggacagcca cctagccaga acctggatac ctacaagttc cctgctacat   2280

acaagtacat caaaaccttc atttatccct acctgaacag cactgtctcc ctccgcgctg   2340

cttccaagga tcccgaatac ggtcgtacag actttatccc accccacgcg cgtgatggct   2400

cccctcaacc tctcaacccc gctggagacc cagtggccag tggtggaaac aacatgctct   2460

acgacgaact ttacgaggtc actgcacaga tcaaaaacac tggcgacgtg gccggcgacg   2520

aagtcgtcca gctttacgta gatctcgggg gtgacaaccc gcctcgtcag ttgagaaact   2580

ttgacaggtt ttatctgctg cccggtcaga gctcaacatt ccgggctaca ttgacgcgcc   2640

gtgatttgag caactgggat attgaggcgc agaactggcg agttacggaa tcgcctaaga   2700

gagtgtatgt tggacggtcg agtcgggatt tgccgctgag ctcacaattg gagtaatgat   2760

catgtctacc aatagatgtt gaatgtctgg tgtggatatt                         2800
```

<210> SEQ ID NO 74
<211> LENGTH: 878
<212> TYPE: PRT
<213> ORGANISM: Penicillium brasilianum

<400> SEQUENCE: 74

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80
```

```
Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
```

```
            500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
        675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
        755                 760                 765

Gly Asp Pro Val Ala Ser Gly Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
        835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875


<210> SEQ ID NO 75
<211> LENGTH: 2583
<212> TYPE: DNA
<213> ORGANISM: Aspergillus niger

<400> SEQUENCE: 75

atgaggttca ctttgatcga ggcggtggct ctgactgccg tctcgctggc cagcgctgat      60
```

```
gaattggcct actccccacc gtattaccca tccccttggg ccaatggcca gggcgactgg    120
gcgcaggcat accagcgcgc tgttgatatt gtctcgcaaa tgacattgga tgagaaggtc    180
aatctgacca caggaactgg atgggaattg gaactatgtg ttggtcagac tggcggtgtt    240
ccccgattgg gagttccggg aatgtgttta caggatagcc ctctgggcgt tcgcgactcc    300
gactacaact ctgctttccc tgccggcatg aacgtggctg caacctggga caagaatctg    360
gcataccttc gcggcaaggc tatgggtcag gaatttagtg acaagggtgc cgatatccaa    420
ttgggtccag ctgccggccc tctcggtaga agtcccgacg gtggtcgtaa ctgggagggc    480
ttctccccag accctgccct aagtggtgtg ctctttgccg agaccatcaa gggtatccaa    540
gatgctggtg tggttgcgac ggctaagcac tacattgctt acgagcaaga gcatttccgt    600
caggcgcctg aagcccaagg ttttggattt aatatttccg agagtggaag tgcgaacctc    660
gatgataaga ctatgcacga gctgtacctc tggcccttcg cggatgccat ccgtgcaggt    720
gctggcgctg tgatgtgctc ctacaaccag atcaacaaca gttatggctg ccagaacagc    780
tacactctga acaagctgct caaggccgag ctgggcttcc agggctttgt catgagtgat    840
tgggctgctc accatgctgg tgtgagtggt gctttggcag gattggatat gtctatgcca    900
ggagacgtcg actacgacag tggtacgtct tactggggta caaacttgac cattagcgtg    960
ctcaacggaa cggtgcccca atggcgtgtt gatgacatgg ctgtccgcat catggccgcc   1020
tactacaagg tcggccgtga ccgtctgtgg actcctccca acttcagctc atggaccaga   1080
gatgaatacg gctacaagta ctactacgtg tcggagggac cgtacgagaa ggtcaaccag   1140
tacgtgaatg tgcaacgcaa ccacagcgaa ctgattcgcc gcattggagc ggacagcacg   1200
gtgctcctca agaacgacgg cgctctgcct ttgactggta aggagcgcct ggtcgcgctt   1260
atcggagaag atgcgggctc caacccttat ggtgccaacg gctgcagtga ccgtggatgc   1320
gacaatggaa cattggcgat gggctgggga agtggtactg ccaacttccc atacctggtg   1380
acccccgagc aggccatctc aaacgaggtg cttaagcaca agaatggtgt attcaccgcc   1440
accgataact gggctatcga tcagattgag gcgcttgcta agaccgccag tgtctctctt   1500
gtctttgtca acgccgactc tggtgagggt tacatcaatg tggacggaaa cctgggtgac   1560
cgcaggaacc tgaccctgtg gaggaacggc gataatgtga tcaaggctgc tgctagcaac   1620
tgcaacaaca caatcgttgt cattcactct gtcggaccag tcttggttaa cgagtggtac   1680
gacaacccca atgttaccgc tatcctctgg ggtggtttgc ccggtcagga gtctggcaac   1740
tctcttgccg acgtcctcta tggccgtgtc aaccccggtg ccaagtcgcc ctttacctgg   1800
ggcaagactc gtgaggccta ccaagactac ttggtcaccg agcccaacaa cggcaacgga   1860
gcccctcagg aagactttgt cgagggcgtc ttcattgact accgtggatt tgacaagcgc   1920
aacgagaccc cgatctacga gttcggctat ggtctgagct acaccacttt caactactcg   1980
aaccttgagg tgcaggtgct gagcgcccct gcatacgagc ctgcttcggg tgagaccgag   2040
gcagcgccaa ccttcggaga ggttggaaat gcgtcggatt acctctaccc cagcggattg   2100
cagagaatta ccaagttcat ctacccctgg ctcaacggta ccgatctcga ggcatcttcc   2160
ggggatgcta gctacgggca ggactcctcc gactatcttc ccgagggagc caccgatggc   2220
tctgcgcaac cgatcctgcc tgccggtggc ggtcctggcg gcaaccctcg cctgtacgac   2280
gagctcatcc gcgtgtcagt gaccatcaag aacaccggca aggttgctgg tgatgaagtt   2340
ccccaactgt atgtttccct tggcggtccc aatgagccca agatcgtgct gcgtcaattc   2400
gagcgcatca cgctgcagcc gtcggaggag acgaagtgga gcacgactct gacgcgccgt   2460
```

```
gaccttgcaa actggaatgt tgagaagcag gactgggaga ttacgtcgta tcccaagatg   2520

gtgtttgtcg gaagctcctc gcggaagctg ccgctccggg cgtctctgcc tactgttcac   2580

taa                                                                 2583


<210> SEQ ID NO 76
<211> LENGTH: 860
<212> TYPE: PRT
<213> ORGANISM: Aspergillus niger

<400> SEQUENCE: 76

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350
```

```
Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
```

```
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860


<210> SEQ ID NO 77
<211> LENGTH: 2583
<212> TYPE: DNA
<213> ORGANISM: Aspergillus aculeatus

<400> SEQUENCE: 77

atgaagctca gttggcttga ggcggctgcc ttgacggctg cttcagtcgt cagcgctgat      60

gaactggcgt tctctcctcc tttctacccc tctccgtggg ccaatggcca gggagagtgg     120

gcggaagcct accagcgtgc agtggccatt gtatcccaga tgactctgga tgagaaggtc     180

aacctgacca ccggaactgg atgggagctg gagaagtgcg tcggtcagac tggtggtgtc     240

ccaagactga acatcggtgg catgtgtctt caggacagtc ccttgggaat tcgtgatagt     300

gactacaatt cggctttccc tgctggtgtc aacgttgctg cgacatggga caagaacctt     360

gcttatctac gtggtcaggc tatgggtcaa gagttcagtg acaaaggaat tgatgttcaa     420

ttgggaccgg ccgcgggtcc cctcggcagg agccctgatg gaggtcgcaa ctgggaaggt     480

ttctctccag acccggctct tactggtgtg ctctttgcgg agacgattaa gggtattcaa     540

gacgctggtg tcgtggcgac agccaagcat tacattctca atgagcaaga gcatttccgc     600

caggtcgcag aggctgcggg ctacggattc aatatctccg acacgatcag ctctaacgtt     660

gatgacaaga ccattcatga aatgtacctc tggcccttcg cggatgccgt tcgcgccggc     720

gttggcgcca tcatgtgttc ctacaaccag atcaacaaca gctacggttg ccagaacagt     780

tacactctga acaagcttct gaaggccgag ctcggcttcc agggctttgt gatgtctgac     840

tggggtgctc accacagtgg tgttggctct gctttggccg gcttggatat gtcaatgcct     900

ggcgatatca ccttcgattc tgccactagt ttctggggta ccaacctgac cattgctgtg     960

ctcaacggta ccgtcccgca gtggcgcgtt gacgacatgg ctgtccgtat catggctgcc    1020

tactacaagg ttggccgcga ccgcctgtac cagccgccta acttcagctc ctggactcgc    1080

gatgaatacg gcttcaagta tttctacccc caggaagggc cctatgagaa ggtcaatcac    1140

tttgtcaatg tgcagcgcaa ccacagcgag gttattcgca agttgggagc agacagtact    1200

gttctactga agaacaacaa tgccctgccg ctgaccggaa aggagcgcaa agttgcgatc    1260

ctgggtgaag atgctggatc caactcgtac ggtgccaatg gctgctctga ccgtggctgt    1320

gacaacggta ctcttgctat ggcttggggt agcggcactg ccgaattccc atatctcgtg    1380

acccctgagc aggctattca agccgaggtg ctcaagcata agggcagcgt ctacgccatc    1440

acggacaact gggcgctgag ccaggtggag accctcgcta aacaagccag tgtctctctt    1500

gtatttgtca actcggacgc gggagagggc tatatctccg tggacggaaa cgagggcgac    1560

cgcaacaacc tcaccctctg gaagaacggc gacaacctca tcaaggctgc tgcaaacaac    1620

tgcaacaaca ccatcgttgt catccactcc gttggacctg ttttggttga cgagtggtat    1680
```

```
gaccacccca acgttactgc catcctctgg gcgggcttgc ctggccagga gtctggcaac   1740

tccttggctg acgtgctcta cggccgcgtc aacccgggcg ccaaatctcc attcacctgg   1800

ggcaagacga gggaggcgta cggggattac cttgtccgtg agctcaacaa cggcaacgga   1860

gctccccaag atgatttctc ggaaggtgtt ttcattgact accgcggatt cgacaagcgc   1920

aatgagaccc cgatctacga gttcggacat ggtctgagct acaccacttt caactactct   1980

ggccttcaca tccaggttct caacgcttcc tccaacgctc aagtagccac tgagactggc   2040

gccgctccca ccttcggaca agtcggcaat gcctctgact acgtgtaccc tgagggattg   2100

accagaatca gcaagttcat ctatccctgg cttaattcca cagacctgaa ggcctcatct   2160

ggcgacccgt actatggagt cgacaccgcg gagcacgtgc ccgagggtgc tactgatggc   2220

tctccgcagc ccgttctgcc tgccggtggt ggctctggtg gtaacccgcg cctctacgat   2280

gagttgatcc gtgtttcggt gacagtcaag aacactggtc gtgttgccgg tgatgctgtg   2340

cctcaattgt atgtttccct tggtggaccc aatgagccca aggttgtgtt gcgcaaattc   2400

gaccgcctca ccctcaagcc ctccgaggag acggtgtgga cgactaccct gacccgccgc   2460

gatctgtcta actgggacgt tgcggctcag gactgggtca tcacttctta cccgaagaag   2520

gtccatgttg gtagctcttc gcgtcagctg ccccttcacg cggcgctccc gaaggtgcaa   2580

tga                                                                 2583
```

<210> SEQ ID NO 78
<211> LENGTH: 860
<212> TYPE: PRT
<213> ORGANISM: Aspergillus aculeatus

<400> SEQUENCE: 78

```
Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205
```

-continued

```
Gly Phe Asn Ile Ser Asp Thr Ile Ser Ser Asn Val Asp Asp Lys Thr
    210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
    290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Asn Cys Asn Asn Thr
    530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640
```

```
Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860
```

<210> SEQ ID NO 79
<211> LENGTH: 3294
<212> TYPE: DNA
<213> ORGANISM: Aspergillus oryzae

<400> SEQUENCE: 79

```
atgcgttcct ccccctcct ccgctccgcc gttgtggccg ccctgccggt gttggccctt     60

gccgctgatg gcaggtccac ccgctactgg gactgctgca agccttcgtg cggctgggcc    120

aagaaggctc ccgtgaacca gcctgtcttt tcctgcaacg ccaacttcca gcgtatcacg    180

gacttcgacg ccaagtccgg ctgcgagccg ggcggtgtcg cctactcgtg cgccgaccag    240

accccatggg ctgtgaacga cgacttcgcg ctcggttttg ctgccacctc tattgccggc    300

agcaatgagg cgggctggtg ctgcgcctgc tacgagctca ccttcacatc cggtcctgtt    360

gctggcaaga agatggtcgt ccagtccacc agcactggcg gtgatcttgg cagcaaccac    420

ttcgatctca acatccccgg cggcggcgtc ggcatcttcg acggatgcac tccccagttc    480

ggtggtctgc ccggccagcg ctacggcggc atctcgtccc gcaacgagtg cgatcggttc    540

cccgacgccc tcaagcccgg ctgctactgg cgcttcgact ggttcaagaa cgccgacaat    600

ccgagcttca gcttccgtca ggtccagtgc ccagccgagc tcgtcgctcg caccggatgc    660

cgccgcaacg acgacggcaa cttccctgcc gtccagatcc ccatgcgttc ctcccccctc    720

ctccgctccg ccgttgtggc cgccctgccg gtgttggccc ttgccaagga tgatctcgcg    780

tactcccctc ctttctaccc ttccccatgg gcagatggtc agggtgaatg ggcggaagta    840

tacaaacgcg ctgtagacat agtttcccag atgacgttga cagagaaagt caacttaacg    900
```

```
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaagg tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gtcatgtgct cttacaacca aatcaacaac agctacggtt gcgagaatag cgaaactctg   1500
aacaagcttt tgaaggcgga gcttggtttc caaggcttcg tcatgagtga ttggaccgct   1560
catcacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgtttgc ccgctagtgg tggtgccgga ggaaaccccg gtctgtacga ggatcttttc   3000
cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttacccgtcg tgaccttgca   3180
aactgggacg tttcggctca ggactggacc gtcactcctt accccaagac gatctacgtt   3240
ggaaactcct cacggaaact gccgctccag gcctcgctgc ctaaggccca gtaa         3294
```

<210> SEQ ID NO 80
<211> LENGTH: 1097
<212> TYPE: PRT
<213> ORGANISM: Aspergillus oryzae

<400> SEQUENCE: 80

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380
```

```
Leu Gly Ala His Pro Asp Gly Gly Arg Asn Trp Glu Gly Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
    770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
```

```
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe  Arg Val Ser Val Lys  Val Lys Asn
        995                 1000                1005

Thr Gly  Asn Val Ala Gly Asp  Glu Val Pro Gln Leu  Tyr Val Ser
    1010                1015                1020

Leu Gly  Gly Pro Asn Glu Pro  Lys Val Val Leu Arg  Lys Phe Glu
    1025                1030                1035

Arg Ile  His Leu Ala Pro Ser  Gln Glu Ala Val Trp  Thr Thr Thr
    1040                1045                1050

Leu Thr  Arg Arg Asp Leu Ala  Asn Trp Asp Val Ser  Ala Gln Asp
    1055                1060                1065

Trp Thr  Val Thr Pro Tyr Pro  Lys Thr Ile Tyr Val  Gly Asn Ser
    1070                1075                1080

Ser Arg  Lys Leu Pro Leu Gln  Ala Ser Leu Pro Lys  Ala Gln
    1085                1090                1095


<210> SEQ ID NO 81
<211> LENGTH: 3294
<212> TYPE: DNA
<213> ORGANISM: Aspergillus oryzae

<400> SEQUENCE: 81

atgcgttcct ccccctcct ccgctccgcc gttgtggccg ccctgccggt gttggccctt      60

gccgctgatg gcaggtccac ccgctactgg gactgctgca agccttcgtg cggctgggcc    120

aagaaggctc ccgtgaacca gcctgtcttt tcctgcaacg ccaacttcca gcgtatcacg    180

gacttcgacg ccaagtccgg ctgcgagccg ggcggtgtcg cctactcgtg cgccgaccag    240

accccatggg ctgtgaacga cgacttcgcg ctcggttttg ctgccacctc tattgccggc    300

agcaatgagg cgggctggtg ctgcgcctgc tacgagctca ccttcacatc cggtcctgtt    360

gctggcaaga agatggtcgt ccagtccacc agcactggcg gtgatcttgg cagcaaccac    420

ttcgatctca acatccccgg cggcggcgtc ggcatcttcg acggatgcac tccccagttc    480
```

```
ggtggtctgc ccggccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc ccatgcgttc ctccccccctc   720
ctccgctccg ccgttgtggc cgccctgccg gtgttggccc ttgccaagga tgatctcgcg    780
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
```

```
aactacggct gggaagactc caagtatatt cccgaaggcg ccacggatgg gtctgcccag   2940

ccccgtttgc ccgctagtgg tggtgccgga ggaaaccccg gtctgtacga ggatcttttc   3000

cgcgtctctg tgaaggtcaa gaacacgggc aatgtcgccg gtgatgaagt tcctcagctg   3060

tacgtttccc taggcggccc gaatgagccc aaggtggtac tgcgcaagtt tgagcgtatt   3120

cacttggccc cttcgcagga ggccgtgtgg acaacgaccc ttacccgtcg tgaccttgca   3180

aactgggacg tttcggctca ggactggacc gtcactcctt accccaagac gatctacgtt   3240

ggaaactcct cacggaaact gccgctccag gcctcgctgc ctaaggccca gtaa         3294


<210> SEQ ID NO 82
<211> LENGTH: 1097
<212> TYPE: PRT
<213> ORGANISM: Aspergillus oryzae

<400> SEQUENCE: 82

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
```

```
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735
```

```
Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
    770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe  Arg Val Ser Val Lys  Val Lys Asn
        995                 1000                1005

Thr Gly  Asn Val Ala Gly Asp  Glu Val Pro Gln Leu  Tyr Val Ser
    1010                1015                1020

Leu Gly  Gly Pro Asn Glu Pro  Lys Val Val Leu Arg  Lys Phe Glu
    1025                1030                1035

Arg Ile  His Leu Ala Pro Ser  Gln Glu Ala Val Trp  Thr Thr Thr
    1040                1045                1050

Leu Thr  Arg Arg Asp Leu Ala  Asn Trp Asp Val Ser  Ala Gln Asp
    1055                1060                1065

Trp Thr  Val Thr Pro Tyr Pro  Lys Thr Ile Tyr Val  Gly Asn Ser
    1070                1075                1080

Ser Arg  Lys Leu Pro Leu Gln  Ala Ser Leu Pro Lys  Ala Gln
    1085                1090                1095
```

POLYPEPTIDES HAVING CELLULOLYTIC ENHANCING ACTIVITY AND POLYNUCLEOTIDES ENCODING SAME

Cross-Reference to Related Applications

This application is a divisional application of U.S. application Ser. No, 12/130,722 filed May 30, 2008, now U.S. Pat. No. 8,044,264, which claims the benefit of U.S. Provisional Application No. 60/941,234, filed May 31, 2007, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production.

These materials primarily consist of cellulose, hemicellulose, and lignin. Once the cellulose is converted to glucose, the glucose is easily fermented by yeast into ethanol.

It would be advantageous in the art to improve the ability to convert cellulosic feedstocks.

WO 2005/074647 discloses isolated polypeptides having cellulolytic enhancing activity and polynucleotides thereof from *Thielavia terrestris*.

WO 2005/074656 discloses an isolated polypeptide having cellulolytic enhancing activity and the polynucleotide thereof from *Thermoascus aurantiacus*.

U.S. Published Application Serial No. 2007/0077630 discloses an isolated polypeptide having cellulolytic enhancing activity and the polynucleotide thereof from *Trichoderma reesei*.

The present invention provides polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide comprising an amino acid sequence having at least 60% identity to the mature polypeptide of SEQ ID NO: 2;

(b) a polypeptide encoded by a polynucleotide that hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polypeptide encoded by a polynucleotide comprising a nucleotide sequence having at least 60% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having cellulolytic enhancing activity, selected from the group consisting of:

(a) a polynucleotide encoding a polypeptide comprising an amino acid sequence having at least 60% identity to the mature polypeptide of SEQ ID NO: 2;

(b) a polynucleotide that hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polynucleotide comprising a nucleotide sequence having at least 60% identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having cellulolytic enhancing activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods for degrading or converting a cellulose-containing material, comprising: treating the cellulose-containing material with an effective amount of a cellulolytic enzyme composition in the presence of an effective amount of such a polypeptide having cellulolytic enhancing activity, wherein the presence of the polypeptide having cellulolytic enhancing activity increases the degradation of cellulose-containing material compared to the absence of the polypeptide having cellulolytic enhancing activity.

The present invention also relates to methods of producing a fermentation product, comprising: (a) saccharifying a cellulose-containing material with an effective amount of a cellulolytic enzyme composition in the presence of an effective amount of such a polypeptide having cellulolytic enhancing activity, wherein the presence of the polypeptide having cellulolytic enhancing activity increases the degradation of cellulose-containing material compared to the absence of the polypeptide having cellulolytic enhancing activity; (b) fermenting the saccharified cellulose-containing material of step (a) with one or more fermentating microorganisms to produce the fermentation product; and (c) recovering the fermentation product from the fermentation.

The present invention also relates to plants comprising an isolated polynucleotide encoding such a polypeptide having cellulolytic enhancing activity.

The present invention also relates to methods of producing such a polypeptide having cellulolytic enhancing activity, comprising: (a) cultivating a transgenic plant or a plant cell comprising a polynucleotide encoding such a polypeptide having cellulolytic enhancing activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 15 of SEQ ID NO: 2, wherein the gene is foreign to the nucleotide sequence.

BRIEF DESCRIPTION OF THE FIGURES

FIG. 1 shows the cDNA sequence and the deduced amino acid sequence of a *Thielavia terrestris* NRRL 8126 polypeptide having cellulolytic enhancing activity (SEQ ID NOs: 1 and 2, respectively).

FIG. 10 shows the DNA sequence and amino acid sequence of an *Aspergillus oryzae* beta-glucosidase native signal sequence (SEQ ID NOs: 37 and 38).

FIG. 11 shows the DNA sequence and amino acid sequence of a *Humicola insolens* endoglucanase V signal sequence (SEQ ID NOs: 41 and 42).

DEFINITIONS

Figure 2:
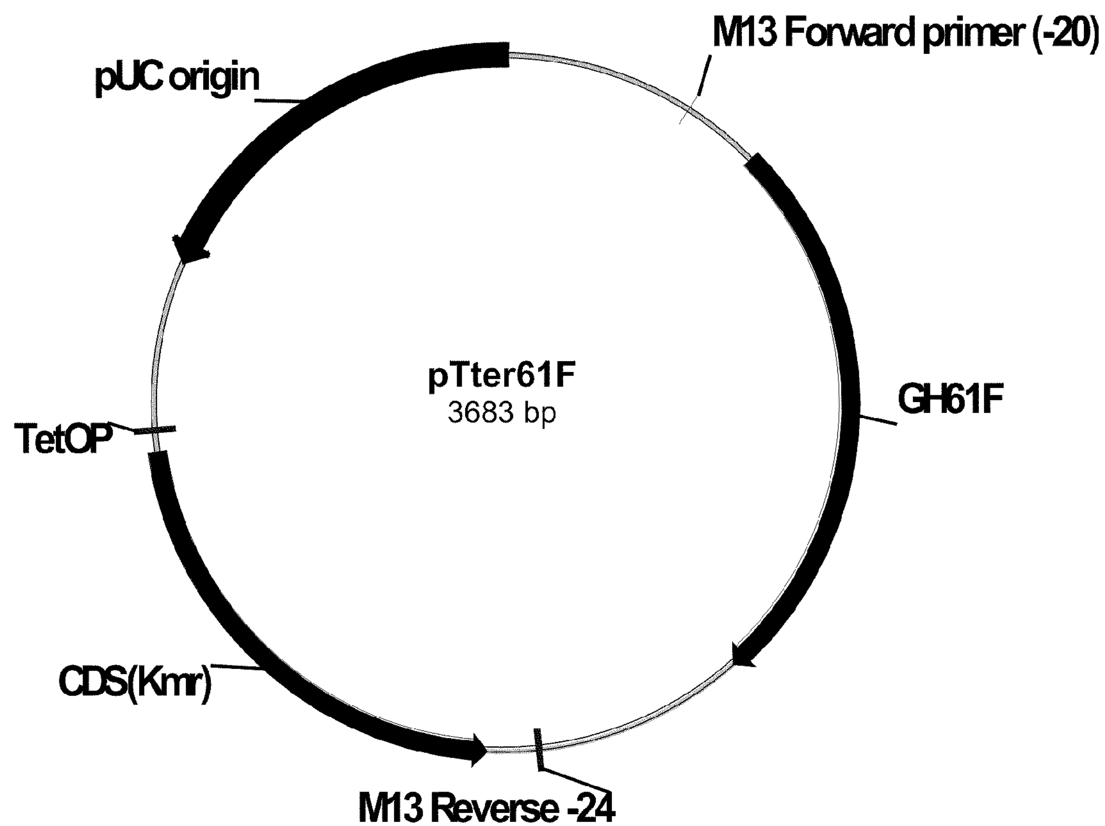
FIG. 2 shows a restriction map of pTter61F.

Cellulolytic enhancing activity: The term "cellulolytic enhancing activity" is defined herein as a biological activity which enhances the hydrolysis of a cellulose-containing material by proteins having cellulolytic activity. For purposes of the present invention, cellulolytic enhancing activity is determined by measuring the increase in reducing sugars or in the increase of the total of cellobiose and glucose from the hydrolysis of a cellulose-containing material by cellulolytic protein under the following conditions: 1-50 mg of total protein/g of cellulose in PCS, wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* according to Example 22 of WO 02/095014) of cellulase protein loading is used as the source of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of SEQ ID NO: 2.

The polypeptides having cellulolytic enhancing activity enhance the hydrolysis of a cellulose-containing material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

Cellulolytic activity: The term "cellulolytic activity" is defined herein as a biological activity which hydrolyzes a cellulose-containing material. Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate. For CELLUCLAST™ (Novozymes A/S, Bagsværd, Denmark) the assay is carried out at 40° C. in 0.1 M phosphate pH 9.0 buffer for 30 minutes with CMC as substrate (33.3 g/L carboxymethyl cellulose Hercules 7 LFD) and an enzyme concentration of approximately 3.3-4.2 CEVU/ml. The CEVU activity is calculated relative to a declared enzyme standard, such as CELLUZYME™ Standard 17-1194 (obtained from Novozymes A/S, Bagsværd, Denmark).

For purposes of the present invention, cellulolytic activity is determined by measuring the increase in hydrolysis of a cellulose-containing material by a cellulolytic mixture under the following conditions: 1-10 mg of cellulolytic protein/g of cellulose in PCS for 5-7 day at 50° C. compared to a control hydrolysis without addition of cellulolytic protein.

Endoglucanase: The term "endoglucanase" is defined herein as an endo-1,4-(1,3; 1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

Family 61 glycoside hydrolase: The term "Family 61 glycoside hydrolase" or "Family GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, catalytic proton donors, and 3-D structure are not known for polypeptides belonging to this family. A GH61 protein is also referred to as a CEL61 protein.

Cellulose-containing material: The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

The cellulose-containing material can be any material containing cellulose. Cellulose is generally found, for example, in the stems, leaves, hulls, husks, and cobs of plants or leaves, branches, and wood of trees. The cellulose-containing material can be, but is not limited to, herbaceous material, agricultural residues, forestry residues, municipal solid wastes, waste paper, and pulp and paper mill residues. The cellulose-containing material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix.

In a preferred aspect, the cellulose-containing material is corn stover. In another preferred aspect, the cellulose-containing material is corn fiber. In another preferred aspect, the cellulose-containing material is corn cobs. In another preferred aspect, the cellulose-containing material is rice straw. In another preferred aspect, the cellulose-containing material is paper and pulp processing waste. In another preferred aspect, the cellulose-containing material is woody or herbaceous plants. In another preferred aspect, the cellulose-containing material is bagasse.

The cellulose-containing material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N.J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Pre-treated corn stover: The term "PCS" or "Pre-treated Corn Stover" is defined herein as a cellulose-containing material derived from corn stover by treatment with heat and dilute acid. For purposes of the present invention, PCS is made by the method described herein.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having cellulolytic enhancing activity that is in its final form following translation and any post-translational modifications, such as N-terminal processing, C-terminal truncation, glycosylation, phosphorylation, etc. In a preferred aspect, the mature polypeptide is amino acids 16 to 317 of SEQ ID NO: 2 based on the SignalP program that predicts amino acids 1 to 15 of SEQ ID NO: 2 are a signal peptide.

Mature polypeptide coding sequence: The term "mature polypeptide coding sequence" is defined herein as a nucleotide sequence that encodes a mature polypeptide having cellulolytic enhancing activity. In a preferred aspect, the mature polypeptide coding sequence is nucleotides 46 to 951 of SEQ ID NO: 1 based on the SignalP program that predicts nucleotides 1 to 45 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, *in Bioinformatics Methods and Protocols*, S. Misener and S. A. Krawetz, ed., pp. 185-219) with the mature polypeptide of SEQ ID NO: 2.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has cellulolytic enhancing activity. In a preferred aspect, a fragment contains at least 255 amino acid residues, more preferably at least 270 amino acid residues, and most preferably at least 285 amino acid residues, of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having cellulolytic enhancing activity. In a preferred aspect, a subsequence contains at least 765 nucleotides, more preferably at least 810 nucleotides, and most preferably at least 855 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having cellulolytic enhancing activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Cellulolytic Enhancing Activity

In a first aspect, the present invention relates to isolated polypeptides comprising or consisting of an amino acid sequence having a degree of identity to the mature polypeptide of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In a preferred aspect, the homologous polypeptides comprise or consist of an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having cellulolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 16 to 317 of SEQ ID NO: 2, or an allelic variant thereof; or a fragment thereof having cellulolytic enhancing activity. In another preferred aspect, the polypeptide comprises amino acids 16 to 317 of SEQ ID NO: 2. In another preferred aspect, the polypeptide consists of the amino acid sequence of SEQ ID NO: 2 or an allelic variant thereof; or a fragment thereof having cellulolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 16 to 317 of SEQ ID NO: 2 or an allelic variant thereof; or a fragment thereof having cellulolytic enhancing activity. In another preferred aspect, the polypeptide consists of amino acids 16 to 317 of SEQ ID NO: 2.

In a second aspect, the present invention relates to isolated polypeptides having cellulolytic enhancing activity that are encoded by polynucleotides comprising or consisting of nucleotide sequences that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having cellulolytic enhancing activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having cellulolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 46 to 951 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pTter61F which is contained in *E. coli* NRRL B-50044, wherein the polynucleotide sequence thereof encodes a polypeptide having cellulolytic enhancing activity. In another preferred aspect, the nucleic acid probe is the mature polypeptide coding region contained in plasmid pTter61F which is contained in *E. coli* NRRL B-50044.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having cellulolytic enhancing activity encoded by polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., cellulolytic enhancing activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 19 to 317 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having cellulolytic enhancing activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having cellulolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having cellulolytic enhancing activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enhancing activity.

In another preferred aspect, the polypeptide is a *Streptococcus equisimilis, Streptococcus pyogenes, Streptococcus uberis*, or *Streptococcus equi* subsp. *Zooepidemicus* polypeptide having cellulolytic enhancing activity.

In another preferred aspect, the polypeptide is a *Streptomyces achromogenes, Streptomyces avermitilis, Streptomyces coelicolor, Streptomyces griseus*, or *Streptomyces lividans* polypeptide having cellulolytic enhancing activity.

A polypeptide having cellulolytic enhancing activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having cellulolytic enhancing activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enhancing activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Trichoderma harzianum, Trichoderma koningii, Trichoderma longibrachiatum, Trichoderma reesei*, or *Trichoderma viride* polypeptide having cellulolytic enhancing activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila*, or *Thielavia terrestris* polypeptide having cellulolytic enhancing activity.

In a more preferred aspect, the polypeptide is a *Thielavia terrestris* polypeptide having cellulolytic enhancing activity. In a most preferred embodiment, the polypeptide is a *Thielavia terrestris* NRRL 8126 polypeptide having cellulolytic enhancing activity, e.g., the polypeptide comprising the amino acid sequence of SEQ ID NO: 2, or fragments thereof, e.g., the mature protein.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having cellulolytic enhancing activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having cellulolytic enhancing activity of the present invention.

In a preferred aspect, the nucleotide sequence comprises or consists of SEQ ID NO: 1. In another more preferred aspect, the nucleotide sequence comprises or consists of the sequence contained in plasmid pTter61F which is contained in *E. coli* NRRL B-50044. In another preferred aspect, the nucleotide sequence comprises or consists of the mature polypeptide coding sequence of SEQ ID NO: 1. In another preferred aspect, the nucleotide sequence comprises or consists of nucleotides 46 to 951 of SEQ ID NO: 1. In another more preferred aspect, the nucleotide sequence comprises or consists of the mature polypeptide coding sequence contained in plasmid pTter61F which is contained in *E. coli* NRRL B-50044. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have cellulolytic enhancing activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for cellulolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having cellulolytic enhancing activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei lipase, Aspergillus oryzae* alkaline protease, *Aspergillus oryzae* triose phosphate isomerase, *Aspergillus nidulans acetamidase, Fusarium venenatum* amyloglucosidase (WO 00/56900), *Fusarium venenatum* Daria (WO 00/56900), *Fusarium* venenatum Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger glucoamylase, Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae enolase, Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger glucoamylase, Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 15 of SEQ ID NO: 2. In another preferred aspect, the signal peptide coding sequence comprises or consists of nucleotides 1 to 45 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s)

in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-

3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium* Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium* venenatum cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art.

For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having cellulolytic enhancing activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, Plant Journal 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having cellulolytic enhancing activity of the present invention under conditions conducive for production of the polypeptide; and (b) recovering the polypeptide.

Removal or Reduction of Cellulolytic Enhancing Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of cellulolytic enhancing activity by fermentation of a cell that produces both a polypeptide of the present invention as well as the protein product of interest by adding an effective amount of an agent capable of inhibiting cellulolytic enhancing activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of cellulolytic enhancing activity by cultivating the cell under conditions permitting the expression of the product, subjecting the resultant culture broth to a combined pH and temperature treatment so as to reduce the cellulolytic enhancing activity substantially, and recovering the product from the culture broth. Alternatively, the combined pH and temperature treatment may be performed on an enzyme preparation recovered from the culture broth. The combined pH and temperature treatment may optionally be used in combination with a treatment with an cellulolytic enhancing inhibitor.

In accordance with this aspect of the invention, it is possible to remove at least 60%, preferably at least 75%, more preferably at least 85%, still more preferably at least 95%, and most preferably at least 99% of the cellulolytic enhancing activity. Complete removal of cellulolytic enhancing activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially cellulolytic enhancing-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The cellulolytic enhancing-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Methods of Inhibiting Expression of a Polypeptide

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. Nos. 6,506,559; 6,511,824; 6,515,109; and 6,489,127.

Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The composition may comprise a polypeptide of the present invention as the major component, e.g., a mono-component composition. Alternatively, the composition may comprise multiple enzymatic activities, such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

In a preferred aspect, the composition comprises one or more cellulolytic enzymes and a polypeptide of the present invention, as described herein.

The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods of Processing a Cellulose-Containing Material

The present invention also relates to methods for degrading or converting a cellulose-containing material, comprising: treating the cellulose-containing material with an effective amount of a cellulolytic enzyme composition in the presence of an effective amount of a polypeptide having cellulolytic enhancing activity of the present invention, wherein the presence of the polypeptide having cellulolytic enhancing activity increases the degradation of cellulose-containing material compared to the absence of the polypeptide having cellulolytic enhancing activity.

The present invention also relates to methods for producing a fermentation product, comprising: (a) saccharifying a cellulose-containing material with an effective amount of a cellulolytic enzyme composition in the presence of an effective amount of a polypeptide having cellulolytic enhancing activity of the present invention, wherein the presence of the polypeptide having cellulolytic enhancing activity increases the degradation of cellulose-containing material compared to the absence of the polypeptide having cellulolytic enhancing activity; (b) fermenting the saccharified cellulose-containing material of step (a) with one or more fermentating microorganisms to produce the fermentation product; and (c) recovering the fermentation product from the fermentation.

The methods of the present invention can be used to hydrolyze (saccharify) a cellulose-containing material, e.g., lignocellulose, to fermentable sugars and convert the fermentable sugars to many useful substances, e.g., chemicals and fuels. The production of a desired fermentation product from cellulose-containing material typically involves pretreatment, enzymatic hydrolysis (saccharification), and fermentation.

The processing of cellulose-containing material according to the present invention can be accomplished using processes known in the art. Moreover, the methods of the present invention can be implemented using any biomass processing apparatus configured to operate in accordance with the invention.

Hydrolysis (saccharification) and fermentation, separate or simultaneous, include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation), HHCF (hybrid hydrolysis and fermentation), and direct microbial conversion (DMC). It is understood herein that any method known in the art comprising pretreatment, enzymatic hydrolysis (saccharification), fermentation, or a combination thereof, can be used in practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include, for example, fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components of the cellulose-containing material. The cellulose-containing material can also be subjected to pre-soaking, wetting, or conditioning prior to pretreatment using methods known in the art. Conventional pretreatments include, but are not limited to, steam pretreatment (with or without explosion), dilute acid pretreatment, hot water pretreatment, lime pretreatment, wet oxidation, wet explosion, ammonia fiber explosion, organosolv pretreatment, and biological pretreatment. Additional pretreatments include ultrasound, electroporation, microwave, supercritical $CO_2$, supercritical $H_2O$, and ammonia percolation.

The cellulose-containing material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulose-containing material with one or more cellulolytic enzymes, or other enzyme activities, to release fermentable sugars, such as glucose and/or maltose. In most cases the pretreatment step itself results in some conversion of biomass to fermentable sugars (even in absence of enzymes).

Steam Pretreatment. In steam pretreatment, the cellulose-containing material is heated to disrupt the plant cell wall components, including lignin, hemicellulose, and cellulose to make the cellulose and other fractions, e.g., hemicellulase, accessible to enzymes. The cellulose material is passed to or through a reaction vessel where steam is injected to increase the temperature to the required temperature and pressure and is retained therein for the desired reaction time. Steam pretreatment is preferably done at 140-230° C., more preferably at 160-200° C., and most preferably at 170-190° C., where the optimal temperature range depends on addition of a chemical catalyst. Residence time for the steam pretreatment is preferably 1-15 minutes, more preferably 3-12 minutes, and most preferably 4-10 minutes, where the optimal residence time depends on the temperature range and addition of a chemical catalyst. Steam pretreatment allows for relatively high solids loadings, so that the cellulose-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730).

A catalyst such as $H_2SO_4$ or $SO_2$ (typically 0.3 to 3% w/w) is often added prior to steam pretreatment, which decreases the time and temperature, increases recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulose-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulose-containing material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121:1133-1141; Teymouri et al., 2005, *Bioresource Technol.* 96: 2014-2018).

Organosolv pretreatment delignifies cellulose-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121:219-230). Sulphuric acid is usually added as a catalyst. In organosolv pretreatment, the majority of the hemicellulose is removed.

Other examples of suitable pretreatment methods are described by Schell et al., 2003, *Appl. Biochem. and Biotechnol*. Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride or mixtures thereof. Mild acid treatment is conducted in the pH range of preferably 1-5, more preferably 1-4, and most preferably 1-3. In one aspect, the acid concentration is in the range from preferably 0.01 to 20 wt acid, more preferably 0.05 to 10 wt % acid, even more preferably 0.1 to 5 wt % acid, and most preferably 0.2 to 2.0 wt % acid. The acid is contacted with the cellulose-containing material and held at a temperature, for example, in the range of 160-220° C., preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulose-containing material is present during pretreatment in amounts preferably between 10-80 wt %, more preferably between 20-70 wt %, and most preferably between 30-60 wt %, such as around 50 wt %. The pretreated cellulose-containing material can be unwashed or washed using any method known in the art, e.g., washed with water.

Mechanical Pretreatment The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulose-containing material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulose-containing material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulose-containing material is subjected to mechanical, chemical, or physical pretreatment, or any combination thereof, to promote the separation and/or release of cellulose, hemicellulose and/or lignin.

Biological Pretreatment: The term "biological pretreatment" refers to any biological pretreatment that promotes the separation and/or release of cellulose, hemicellulose, and/or lignin from the cellulose-containing material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the pretreated cellulose-containing material is hydrolyzed to break down cellulose and alternatively also hemicellulose to fermentable sugars, such as glucose, xylose, xylulose, arabinose, maltose, mannose, galactose, and/or soluble oligosaccharides. The hydrolysis is performed enzymatically using a cellulolytic enzyme composition comprising an effective amount of a polypeptide having cellulolytic enhancing activity of the present invention. The enzymes components of the composition can also be added sequentially.

In the methods of the present invention, the cellulolytic enzyme composition may comprise any protein involved in the processing of a cellulose-containing material to glucose, or hemicellulose to xylose, mannose, galactose, and arabinose, their polymers, or products derived from them as described below. In one aspect, the cellulolytic enzyme composition comprises an endoglucanase, a cellobiohydrolase, a beta-glucosidase, or a combination thereof. In another aspect, the cellulolytic enzyme composition further comprises one or more additional enzyme activities to improve the degradation of the cellulose-containing material. Preferred additional enzymes are hemicellulases, esterases (e.g., lipases, phospholipases, and/or cutinases), proteases, laccases, peroxidases, or mixtures thereof.

The cellulolytic enzyme composition may be a monocomponent preparation, e.g., an endoglucanase, a multicomponent preparation, e.g., endoglucanase(s), cellobiohydrolase(s), and beta-glucosidase(s), or a combination of multicomponent and monocomponent protein preparations. The cellulolytic proteins may have activity, i.e., hydrolyze the cellulose-containing material, either in the acid, neutral, or alkaline pH-range.

As mentioned above, the cellulolytic proteins used in the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). The host cell may be a heterologous host (enzyme is foreign to host) or the host may also be a wild-type host (enzyme is native to host). Monocomponent cellulolytic proteins may also be prepared by purifying such a protein from a fermentation broth.

The cellulolytic enzyme compositions supplemented with an effective amount of a polypeptide having cellulolytic enhancing activity may be in any form suitable for use in the processes described herein, such as, for example, a crude fermentation broth(s) with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

A polypeptide having cellulolytic enzyme activity may be obtained from microorganisms of any genus. The term "obtained from" means herein that the enzyme may have been isolated from an organism that naturally produces the enzyme as a native enzyme. The term "obtained from" also means herein that the enzyme may have been produced recombinantly in a host organism, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by chemical or recombinant mutagenesis, such as by site-directed mutagenesis or shuffling. Consequently, chemically modified or protein engineered mutants of cellulolytic proteins may also be used in the present invention. In a preferred aspect, the polypeptide obtained from a given source is secreted extracellularly.

A polypeptide having cellulolytic enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or

*Oceanobacillus* polypeptide having cellulolytic enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having cellulolytic enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enzyme activity.

In another preferred aspect, the polypeptide is a *Streptococcus equisimilis, Streptococcus pyogenes, Streptococcus uberis*, or *Streptococcus* equi subsp. *Zooepidemicus* polypeptide having cellulolytic enzyme activity.

In another preferred aspect, the polypeptide is a *Streptomyces achromogenes, Streptomyces avermitilis, Streptomyces coelicolor, Streptomyces griseus*, or *Streptomyces lividans* polypeptide having cellulolytic enzyme activity.

The polypeptide having cellulolytic enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having cellulolytic enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enzyme activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enzyme activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having cellulolytic enzyme activity.

In the methods of the present invention, any endoglucanase(s), cellobiohydrolase(s), and/or beta-glucosidase(s), as well as other cellulolytic proteins, e.g., hemicellulase(s), can be used.

Examples of bacterial endoglucanases that can be used in the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263; GenBank™ accession no. M15665); *Trichoderma reesei* endoglucanase II (Saloheimo et al., 1988, *Gene* 63:11-22; GenBank™ accession no. M19373); *Trichoderma reesei* endoglucanase III (Okada et al., 1988, *Appl. Environ. Microbiol.* 64: 555-563; GenBank™ accession no. AB003694); *Trichoderma reesei* endoglucanase IV (Saloheimo et al., 1997, *Eur. J. Biochem.* 249: 584-591; GenBank™ accession no. Y11113); and *Trichoderma reesei* endoglucanase V (Saloheimo et al., 1994, *Molecular Microbiology* 13: 219-228; GenBank™ accession no. Z33381); *Aspergillus aculeatus* endoglucanase (Ooi et al., 1990, *Nucleic Acids Research* 18: 5884); *Aspergillis kawachii* endoglucanase (Sakamoto et al., 1995, *Current Genetics* 27: 435-439); *Chrysosporium* sp. Cl (U.S. Pat. No. 6,573,086; GenPept accession no. AAQ38150); *Corynascus heterothallicus* (U.S. Pat. No. 6,855,531; GenPept accession no. AAY00844); *Erwinia carotovara* endoglucanase (Saarilahti et al., 1990, *Gene* 90: 9-14); *Fusarium oxysporum* endoglucanase (GenBank™ accession no. L29381); *Humicola grisea* var. *thermoidea* endoglucanase (GenBank™ accession no. AB003107); *Melanocarpus albomyces* endoglucanase (GenBank™ accession no. MAL515703); *Neurospora crassa* endoglucanase (GenBank™ accession no. XM_324477); *Piromyces equi* (Eberhardt et al., 2000, *Microbiology* 146: 1999-2008; GenPept accession no. CAB92325); *Rhizopus oryzae* (Moriya et al., 2003, *J. Bacteriology* 185: 1749-1756; GenBank™ accession nos. AB047927, AB056667, and AB056668); and *Thielavia terrestris* (WO 2004/053039; EMBL accession no. CQ827970).

Other endoglucanases are disclosed in more than 13 of the Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

In a preferred aspect, the endoglucanase is a *Trichoderma reesei* endoglucanase I (CEL7B). In another preferred aspect, the endoglucanase is a *Trichoderma reesei* endoglucanase II (CEL5A). In another preferred aspect, the endoglucanase is a *Trichoderma reesei* endoglucanase III (CEL12A). In another preferred aspect, the endoglucanase is a *Trichoderma reesei* endoglucanase V (CEL45A). In another preferred aspect, the endoglucanase is a *Myceliophthora thermophila* CEL7 endoglucanase. In another preferred aspect, the endoglucanase is a *Chrysosporium lucknowense* CEL12 endoglucanase. In another preferred aspect, the endoglucanase is a *Chrysosporium lucknowense* CEL45 endoglucanase.

In a more preferred aspect, the *Trichoderma reesei* endoglucanase I (CEL7B) is the mature polypeptide of SEQ ID NO: 46 or an ortholog or variant thereof. In another more preferred aspect, the *Trichoderma reesei* endoglucanase II (CEL5A) is the mature polypeptide of SEQ ID NO: 48 or an ortholog or variant thereof. In another more preferred aspect, the *Trichoderma reesei* endoglucanase III (CEL12A) is the mature polypeptide of SEQ ID NO: 50 or an ortholog or variant thereof. In another more preferred aspect, the *Trichoderma reesei* endoglucanase V (CEL45A) is the mature polypeptide of SEQ ID NO: 52 or an ortholog or variant thereof. In another more preferred aspect, the *Myceliophthora thermophila* CEL7 endoglucanase is the mature polypeptide of SEQ ID NO: 54 or an ortholog or variant thereof. In another more preferred aspect, the *Chrysosporium lucknowense* CEL12 endoglucanase is the mature polypeptide of SEQ ID NO: 56 or an ortholog or variant thereof. In another more preferred aspect, the *Chrysosporium lucknowense* CEL45 endoglucanase is the mature polypeptide of SEQ ID NO: 58 or an ortholog or variant thereof.

In another more preferred aspect, the *Trichoderma reesei* endoglucanase I (CEL7B) is encoded by the mature polypeptide coding sequence of SEQ ID NO: 45 or an ortholog or variant thereof. In another more preferred aspect, the *Trichoderma reesei* endoglucanase II (CEL5A) is encoded by the mature polypeptide coding sequence of SEQ ID NO: 47 or an ortholog or variant thereof. In another more preferred aspect, the *Trichoderma reesei* endoglucanase III (CEL12A) is encoded by the mature polypeptide coding sequence of SEQ ID NO: 49 or an ortholog or variant thereof. In another more preferred aspect, the *Trichoderma reesei* endoglucanase V (CEL45A) is encoded by the mature polypeptide coding sequence of SEQ ID NO: 51 or an ortholog or variant thereof. In another more preferred aspect, the *Myceliophthora thermophila* CEL7 endoglucanase is encoded by the mature polypeptide coding sequence of SEQ ID NO: 53 or an ortholog or variant thereof. In another more preferred aspect, the *Chrysosporium lucknowense* CEL12 endoglucanase is encoded by the mature polypeptide coding sequence of SEQ ID NO: 55 or an ortholog or variant thereof. In another more preferred aspect, the *Chrysosporium lucknowense* CEL45 endoglucanase is encoded by the mature polypeptide coding sequence of SEQ ID NO: 57 or an ortholog or variant thereof.

The *Trichoderma reesei* endoglucanase I (CEL7B) can be obtained according to Penttila et al., 1986, *Gene* 45: 253-263. The *Trichoderma reesei* endoglucanase II (CEL5A) can be obtained according to Saloheimo et al., 1988, *Gene* 63:11-22. The *Trichoderma reesei* endoglucanase III (CEL12A) can be obtained according to Okada et al., 1988, *Appl. Environ. Microbiol.* 64: 555-563. The *Trichoderma reesei* endoglucanase V (CEL45A) can be obtained according to Saloheimo et al., 1994, *Molecular Microbiology* 13: 219-228. The *Myceliophthora thermophila* CEL7 endoglucanase can be obtained according to WO 95/024471. The *Chrysosporium lucknowense* CEL12 endoglucanase can be obtained according to WO 2001/25468. The *Chrysosporium lucknowense* CEL45 endoglucanase can be obtained according to WO 2000/20555.

In another preferred aspect, the cellobiohydrolase is a *Trichoderma reesei* cellobiohydrolase I (CEL7A). In another preferred aspect, the cellobiohydrolase is a *Trichoderma reesei* cellobiohydrolase II (CEL6A). In another preferred aspect, the cellobiohydrolase is a *Chrysosporium lucknowense* CEL7 cellobiohydrolase with a cellulose binding domain. In another preferred aspect, the cellobiohydrolase is a *Myceliophthora thermophila* CEL7 cellobiohydrolase without a cellulose binding domain. In another preferred aspect, the cellobiohydrolase is a *Thielavia terrestris* cellobiohydrolase.

In another more preferred aspect, the *Trichoderma reesei* cellobiohydrolase I (CEL7A) is the mature polypeptide of SEQ ID NO: 60 or an ortholog or variant thereof. In another preferred aspect, the *Trichoderma reesei* cellobiohydrolase II (CEL6A) is the mature polypeptide of SEQ ID NO: 62 or an ortholog or variant thereof. In another more preferred aspect, the *Chrysosporium lucknowense* CEL7 cellobiohydrolase with a cellulose binding domain is the mature polypeptide of SEQ ID NO: 64 or an ortholog or variant thereof. In another more preferred aspect, the *Myceliophthora thermophila* CEL7 cellobiohydrolase without a cellulose binding domain is the mature polypeptide of SEQ ID NO: 66 or an ortholog or variant thereof. In another more preferred aspect, the *Thielavia terrestris* cellobiohydrolase is the mature polypeptide of SEQ ID NO: 68 or an ortholog or variant thereof.

In another more preferred aspect, the *Trichoderma reesei* cellobiohydrolase I (CEL7A) cellobiohydrolase is encoded by the mature polypeptide coding sequence of SEQ ID NO: 59 or an ortholog or variant thereof. In another more preferred aspect, the *Trichoderma reesei* cellobiohydrolase II (CEL6A) cellobiohydrolase is encoded by the mature polypeptide coding sequence of SEQ ID NO: 61 or an ortholog or variant thereof. In another more preferred aspect, the *Chrysosporium lucknowense* CEL7 cellobiohydrolase with a cellulose binding domain is encoded by the mature polypeptide coding sequence of SEQ ID NO: 63 or an ortholog or variant thereof. In another more preferred aspect, the *Myceliophthora thermophila CEL*7 cellobiohydrolase without a cellulose binding domain is encoded by the mature polypeptide coding sequence of SEQ ID NO: 65 or an ortholog or variant thereof. In another more preferred aspect, the *Thielavia terrestris* cellobiohydrolase is encoded by the mature polypeptide coding sequence of SEQ ID NO: 67 or an ortholog or variant thereof.

The *Trichoderma reesei* cellobiohydrolase I (CEL7A) can be obtained according to Shoemaker et al., 1983, *Biotechnology* (N.Y.) 1: 691-696. The *Trichoderma reesei* cellobiohydrolase II (CEL6A) can be obtained according to Terri et al., 1987, *Gene* 51: 43-52. The *Chrysosporium lucknowense* CEL7 cellobiohydrolase with a cellulose binding domain can be obtained according to WO 2001/79507. The *Myceliophthora thermophila* CEL7 cellobiohydrolase without a cellulose binding domain can be obtained according to WO 2003/000941. The *Thielavia terrestris* cellobiohydrolase can be obtained according to WO 2006/074435.

In another preferred aspect, the beta-glucosidase is obtained from *Aspergillus oryzae*. In another preferred aspect, the beta-glucosidase is obtained from *Aspergillus fumigatus*. In another preferred aspect, the beta-glucosidase is obtained from *Penicillium brasilianum*, e.g., *Penicillium brasilianum* strain IBT 20888. In another preferred aspect, the beta-glucosidase is obtained from *Aspergillus niger*. In another preferred aspect, the beta-glucosidase is obtained from *Aspergillus aculeatus*.

In a more preferred aspect, the *Aspergillus oryzae* beta-glucosidase is the mature polypeptide of SEQ ID NO: 70 or an ortholog or variant thereof. In another more preferred aspect, the *Aspergillus fumigatus* beta-glucosidase is the mature polypeptide of SEQ ID NO: 72 or an ortholog or variant thereof. In another more preferred aspect, the *Penicillium brasilianum* beta-glucosidase is the mature polypeptide of SEQ ID NO: 74 or an ortholog or variant thereof. In another more preferred aspect, the *Aspergillus niger* beta-glucosidase is the mature polypeptide of SEQ ID NO: 76 or an ortholog or variant thereof. In another more preferred aspect, the *Aspergillus aculeatus* beta-glucosidase is the mature polypeptide of SEQ ID NO: 78 or an ortholog or variant thereof.

In another more preferred aspect, the *Aspergillus oryzae* beta-glucosidase is encoded by the mature polypeptide coding sequence of SEQ ID NO: 69 or an ortholog or variant thereof. In another more preferred aspect, the *Aspergillus fumigatus* beta-glucosidase is encoded by the mature polypeptide coding sequence of SEQ ID NO: 71 or an ortholog or variant thereof. In another more preferred aspect, the *Penicillium brasilianum* beta-glucosidase is encoded by the mature polypeptide coding sequence of SEQ ID NO: 73 or an ortholog or variant thereof. In another more preferred aspect, the *Aspergillus niger* beta-glucosidase is encoded by the mature polypeptide coding sequence of SEQ ID NO: 75 or an ortholog or variant thereof. In another more preferred aspect, the *Aspergillus aculeatus* beta-glucosidase is encoded by the mature polypeptide coding sequence of SEQ ID NO: 77 or an ortholog or variant thereof.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

In another preferred aspect, the beta-glucosidase is the *Aspergillus oryzae* beta-glucosidase variant BG fusion protein of SEQ ID NO: 80. In another preferred aspect, the *Aspergillus oryzae* beta-glucosidase variant BG fusion protein is encoded by the polynucleotide of SEQ ID NO: 79. In another preferred aspect, the beta-glucosidase is the *Aspergillus oryzae* beta-glucosidase fusion protein of SEQ ID NO: 82. In another preferred aspect, the *Aspergillus oryzae* beta-glucosidase fusion protein is encoded by the polynucleotide of SEQ ID NO: 81.

In a preferred aspect, the cellulolytic enzyme composition comprises a polypeptide having cellulolytic enhancing activity of the present invention; a beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B).

In another preferred aspect, the cellulolytic enzyme composition comprises a polypeptide having cellulolytic enhancing activity of the present invention; a beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B), and further comprises (1) one or more enzymes selected from the group consisting of a *Trichoderma reesei* endoglucanase II (CEL5A), a *Trichoderma reesei* endoglucanase V (CEL45A), and a *Trichoderma reesei* endoglucanase III (CEL12A), and/or further comprises (2) a *Thielavia terrestris* cellobiohydrolase.

In another preferred aspect, the cellulolytic enzyme composition comprises a polypeptide having cellulolytic enhancing activity of the present invention; a beta-glucosidase fusion protein of SEQ ID NO: 82; a *Trichoderma reesei* cellobiohydrolase I (CEL7A) of the mature polypeptide of SEQ ID NO: 60, a *Trichoderma reesei* cellobiohydrolase II (CEL6A) of the mature polypeptide of SEQ ID NO: 62, and a *Trichoderma reesei* endoglucanase I (CEL7B) of the mature polypeptide of SEQ ID NO: 46.

In another preferred aspect, the cellulolytic enzyme composition comprises a polypeptide having cellulolytic enhancing activity of the present invention; a beta-glucosidase fusion protein of SEQ ID NO: 82; a *Trichoderma reesei* cellobiohydrolase I (CEL7A) of the mature polypeptide of SEQ ID NO: 60, a *Trichoderma reesei* cellobiohydrolase II (CEL6A) of the mature polypeptide of SEQ ID NO: 62, and a *Trichoderma reesei* endoglucanase I (CEL7B) of the mature polypeptide of SEQ ID NO: 46, and further comprises one or more enzymes selected from the group consisting of a *Trichoderma reesei* endoglucanase II (CEL5A) of the mature polypeptide of SEQ ID NO: 47, a *Trichoderma reesei* endoglucanase V (CEL45A) of the mature polypeptide of SEQ ID NO: 51, and a *Trichoderma reesei* endoglucanase III (CEL12A) of the mature polypeptide of SEQ ID NO: 49.

In another preferred aspect, the cellulolytic enzyme composition comprises a polypeptide having cellulolytic enhancing activity of the present invention; a beta-glucosidase fusion protein of SEQ ID NO: 82; a *Trichoderma reesei* cellobiohydrolase I (CEL7A) of the mature polypeptide of SEQ ID NO: 60, a *Trichoderma reesei* cellobiohydrolase II (CEL6A) of the mature polypeptide of SEQ ID NO: 62, and a *Trichoderma reesei* endoglucanase I (CEL7B) of the mature polypeptide of SEQ ID NO: 46, and further comprises a *Thielavia terrestris* cellobiohydrolase of the mature polypeptide of SEQ ID NO: 68.

In another preferred aspect, the cellulolytic enzyme composition comprises a polypeptide having cellulolytic enhancing activity of the present invention; a beta-glucosidase fusion protein of SEQ ID NO: 82; a *Trichoderma reesei* cellobiohydrolase I (CEL7A) of the mature polypeptide of SEQ ID NO: 60, a *Trichoderma reesei* cellobiohydrolase II (CEL6A) of the mature polypeptide of SEQ ID NO: 62, and a *Trichoderma reesei* endoglucanase I (CEL7B) of the mature polypeptide of SEQ ID NO: 46, and further comprises (1) one or more enzymes selected from the group consisting of a *Trichoderma reesei* endoglucanase II (CEL5A) of the mature polypeptide of SEQ ID NO: 47, a *Trichoderma reesei* endoglucanase V (CEL45A) of the mature polypeptide of SEQ ID NO: 51, and a *Trichoderma reesei* endoglucanase III (CEL12A) of the mature polypeptide of SEQ ID NO: 49, and/or further comprises (2) a *Thielavia terrestris* cellobiohydrolase of the mature polypeptide of SEQ ID NO: 68.

In another preferred aspect, the cellulolytic enzyme composition comprises one or more (several) components selected from the group consisting of a *Myceliophthora thermophila CEL*7 polypeptide having endoglucanase activity, a *Chrysosporium lucknowense* CEL12 polypeptide having endoglucanase activity, a *Chrysosporium lucknowense* CEL45 polypeptide having endoglucanase activity, a *Chrysosporium lucknowense* CEL7 polypeptide having cellobiohydrolase activity with a cellulose binding domain, and a *Myceliophthora thermophila* CEL7 polypeptide having cellobiohydrolase activity without a cellulose binding domain. In another preferred aspect, the cellulolytic enzyme composition comprises a *Myceliophthora thermophila* CEL7 polypeptide having endoglucanase activity, a *Chrysosporium lucknowense* CEL12 polypeptide having endoglucanase activity, a *Chrysosporium lucknowense* CEL45 polypeptide having endoglucanase activity, a CEL7 polypeptide having cellobiohydrolase activity with a cellulose binding domain, and a *Myceliophthora thermophila* CEL7 polypeptide having cellobiohydrolase activity without a cellulose binding domain. In another preferred aspect, the composition above further comprises one or more (several) polypeptides having beta-glucosidase activity.

The cellulolytic enzyme composition can also be a commercial preparation. Examples of commercial cellulolytic enzyme preparations suitable for use in the present invention include, for example, CELLUCLAST™ (available from Novozymes A/S) and NOVOZYM™ 188 (available from Novozymes A/S). Other commercially available preparations that may be used include CELLUZYME™, CEREFLO™ and ULTRAFLO™ (Novozymes A/S), LAMINEX™ and SPEZYME™ CP (Genencor Int.), ROHAMENT™ 7069 W (Röhm GmbH), and FIBREZYME® LDI, FIBREZYME® LBR, or VISCOSTAR® 150L (Dyadic International, Inc., Jupiter, Fla., USA).

Other cellulolytic proteins that may be useful in the present invention are described in EP 495,257, EP 531,315, EP 531, 372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 5,648,263, 5,686,593, 5,691,178, 5,763,254, and 5,776,757.

The cellulolytic proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic protein production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic protein to be expressed or isolated. The resulting cellulolytic proteins produced by the methods described above may be recovered from the fermentation medium and purified by conventional procedures as described herein.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulose-containing material (substrate) is fed gradually to, for example, an enzyme containing hydrolysis solution.

The saccharification is generally performed in stirred-tank reactors or fermentors under controlled pH, temperature, and mixing conditions. Suitable process time, temperature, and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The optimum amounts of the enzymes and polypeptides having cellulolytic enhancing activity depend on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic protein(s) to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of a polypeptide having cellulolytic enhancing activity to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of polypeptide(s) having cellulolytic enhancing activity to cellulose-containing material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulose-containing material.

In another preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation. The fermentable sugars obtained from the pretreated and hydrolyzed cellulose-containing material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the biofuel industry, consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulose-containing material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation), HHCF (hybrid hydrolysis and fermentation), and direct microbial conversion (DMC).

Any suitable hydrolyzed cellulose-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium, for example, used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of *Saccharomyces* spp., preferably *Saccharomyces cerevisiae.*

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis.*

Other fermenting organisms include strains of *Zymomonas*, such as *Zymomonas mobilis; Hansenula*, such as *Hansenula anomala; Klyveromyces*, such as *K. fragilis; Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum.*

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca.*

The fermenting microorganism(s) is typically added to the degraded cellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the fermenting microorganism(s) is applied to the degraded cellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. The fermenting microorganism(s) is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an aldehyde (e.g., formaldehyde); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an aldehyde. In another more preferred aspect, the aldehyde is formaldehyde.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), distillation, or extraction. For example, ethanol is separated from the fermented cellulose-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to nucleic acid constructs comprising a gene encoding a protein, wherein the gene is operably linked to a nucleotide sequence encoding a signal peptide comprising or consisting of amino acids 1 to 15 of SEQ ID NO: 2, wherein the gene is foreign to the nucleotide sequence.

In a preferred aspect, the nucleotide sequence comprises or consists of nucleotides 1 to 45 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Media

PDA plates were composed per liter of 39 grams of potato dextrose agar.

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, 1 ml of COVE trace metals solution, and sufficient $K_2HPO_4$ to achieve a final pH of approximately 5.4.

NNCYPmod medium was composed per liter of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, 1 ml of COVE trace metals solution, and sufficient $K_2HPO_4$ to achieve a final pH of approximately 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

LB plates were composed per liter of 10 g of tryptone, 5 g of yeast extract, 5 g of sodium chloride, and 15 g of Bacto Agar.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 μl of AMG trace metals solution, and then the pH was adjusted to 5.0 and filter sterilized with a 0.22 μm filtering unit.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.H_2O$, 8.5 g of $MnSO_4.7H_2O$, and 3 g of citric acid.

SOC medium was composed of 2% tryptone, 0.5% yeast extract, 10 mM NaCl, 2.5 mM KCl, 10 mM $MgCl_2$, and 10 mM $MgSO_4$, and then filter-sterilized glucose was added to 20 mM after autoclaving.

Freezing medium was composed of 60% SOC and 40% glycerol.

2×YT medium was composed per liter of 16 g of tryptone, 10 g of yeast extract, 5 g of NaCl, and 15 g of Bacto agar.

Example 1

Identification of a GH61F Polypeptide from *Thielavia terrestris* NRRL 8126

An agarose plug from a fresh plate of *Thielavia terrestris* NRRL 8126 grown on NNCYPmod medium supplemented with 1% SIGMACELL® Type 20 cellulose (Sigma Chemical Co., St. Louis, Mo., USA) was inoculated into 50 ml of NNCYPmod medium supplemented with 1% glucose and incubated at 45° C. and 200 rpm for 25 hours. Then fifteen 500 ml flasks and two 250 ml flasks containing 100 ml and 50 ml, respectively, of NNCYPmod medium supplemented with 2% SIGMACELL® Type 20 cellulose were each inoculated with 2 ml of the above culture. The flasks were incubated at 45° C., 200 rpm for 4 days. The cultures were pooled and centrifuged at 3000×g for 10 minutes and the supernatant was filtered through a NALGENE® glass fiber prefilter (Nalge Nunc Int'l, Rochester, N.Y., USA). The filtrate was cooled to 4° C. for storage.

Two-dimensional polyacrylamide gel electrophoresis. One ml of filtrate was precipitated by adding 100 μl of saturated (4° C.) trichloroacetic acid (TCA) and incubating 10 minutes on ice followed by addition of 9 ml of ice-cold acetone and further incubation on ice for 20 minutes. The precipitated solution was centrifuged at 10,000×g for 10 minutes at 4° C., the supernatant decanted, and the pellet rinsed twice with ice-cold acetone and allowed to air-dry.

The dried pellet was dissolved in 0.2 ml of isoelectric focusing (IEF) sample buffer. The IEF sample buffer was composed of 9.0 M urea, 3.0% w/v 3-[(3-cholamidopropyl) dimethyl-ammonium]-1-propanesulfonate (CHAPS, Pierce Chemical Co. Rockford, Ill., USA), 1% (v/v) pH 4-7 ampholytes, 1% beta-mercaptoethanol, and 0.005% bromophenol blue in distilled water. Urea stock solution was deionized using AG® 501-X8 (D), 20-5-mesh, mixed bed resin (Bio-Rad, Hercules, Calif., USA). The deionized solution was stored at −20° C. The resulting mixture was allowed to solubilize for several hours with gentle mixing on a LABQUAKE® Shaker (Lab Industries, Berkeley, Calif., USA). The sample buffer-protein mixture was applied to an 11 cm IPG strip (Bio-Rad, Hercules, Calif., USA) in an IPG rehydration tray (Amersham Biosciences, Piscataway, N.J., USA). A 750 μl aliquot of dry-strip cover fluid (Amersham Biosciences, Piscataway, N.J., USA) was layered over the IPG strips to prevent evaporation and allowed to rehydrate for 12 hours while applying 30 volts using an IPGPHOR® Isoelectric Focusing Unit (Amersham Biosciences, Piscataway, N.J., USA) at 20° C. The IPGPHOR® Unit was programmed for constant voltage with a maximum current of 50 μA per strip. After 12 hours of rehydration, the isoelectric focusing conditions were as follows: 1 hour at 200 volts, 1 hour at 500 volts, and 1 hour at 1000 volts. Then a gradient was applied from 1000 volts to 8000 volts for 30 minutes and isoelectric focusing was programmed to run at 8000 volts and was complete when >30,000 volt hours was achieved.

IPG gel strips were reduced and alkylated before the second dimension analysis by first reducing for 15 minutes with 100 mg of dithiothreitol per 10 ml of SDS-equilibration buffer followed by 15 minutes of alkylation with 250 mg of iodoacetamide per 10 ml of equilibration buffer in the dark. The SDS-equilibration buffer was composed of 50 mM Tris HCl pH 8.8, 6.0 M urea, 2% w/v sodium dodecylsulfate (SDS), 30% glycerol, and 0.002% w/v bromophenol blue. The IPG strips were rinsed quickly in SDS-PAGE running buffer (Invitrogen/Novex, Carlsbad, Calif., USA) and placed on an 11 cm, 1 well 8-16% Tris-Glycine SDS-PAGE gel (Bio-Rad, Hercules, Calif., USA) and electrophoresed using a CRITERION® electrophoresis unit (Bio-Rad, Hercules, Calif., USA) at 50 volts until the sample entered the gel and then the voltage was increased to 200 volts and allowed to run until the bromophenol blue dye reached the bottom of the gel.

Polypeptide detection. The two dimensional gel was stained with a fluorescent SYPRO® Orange Protein Stain (Molecular Probes, Eugene, Oreg., USA). Fluorescent staining methods were optimized and adapted from Malone et al., 2001, Electrophoresis, 22, 919-932. The SDS-PAGE gel was fixed in 40% ethanol, 2% acetic acid, and 0.0005% SDS on a platform rocker for 1 hour to overnight. Fixing solution was removed and replaced by three repeated wash steps consisting of 2% acetic acid and 0.0005% SDS for 30 minutes each. The gel was stained for 1.5 hours to overnight in the dark with 2% acetic acid, 0.0005% SDS, and 0.02% SYPRO® Orange Protein Stain. Staining and de-staining was further optimized to improve reproducibility and automation on a HOEFER® PROCESSOR PLUS™ Staining Unit (Amersham Biosciences, Piscataway, N.J., USA). Images of the fluorescent stained SDS-PAGE gel was obtained by scanning on a MOLECULAR DYNAMICS® STORM™ 860 Imaging System (Amersham Biosciences, Piscataway, N.J., USA) using blue fluorescence and 200 μm pixel sizes and a photomultiplier tube gain of 800 V. Images were viewed and adjusted using IMAGEQUANT® software version 5.0 (Amersham Biosciences, Piscataway, N.J., USA). The gel was further visualized on a DARK READER® Blue transilluminator with an orange filter (Clare Chemical Co, Denver, Colo., USA). Observed protein gel spots were excised using a 2 mm ACU-PUNCH® Biopsy Punch (Acuderm Inc., Ft. Lauderdale, Fla., USA) and stored in 96-well plates that were prewashed with 0.1% trifluoroacetic acid (TFA) in 60% acetonitrile followed by two additional washes with HPLC grade water. The stained two-dimensional gel spots were stored in 25-50 μl of water in the pre-washed plates at −20° C. until digested.

In-gel digestion of polypeptides for peptide sequencing. A MULTIPROBE® II Liquid Handling Robot (PerkinElmer Life and Analytical Sciences, Boston, Mass., USA) was used to perform the in-gel digestions. Two dimensional gel spots containing polypeptides of interest were reduced with 50 μl of 10 mM dithiothreitol (DTT) in 100 mM ammonium bicarbonate pH 8.0 for 30 minutes at room temperature. Following reduction, the gel pieces were alkylated with 50 μl of 55 mM iodoacetamide in 100 mM ammonium bicarbonate pH 8.0 for 20 minutes. The dried gel pieces were allowed to swell in a trypsin digestion solution consisting of 6 ng of sequencing grade trypsin (Promega, Madison, Wis., USA) per pi of 50 mM ammonium bicarbonate pH 8 for 30 minutes at room temperature, followed by an 8 hour digestion at 40° C. Each of the reaction steps described was followed by numerous washes and pre-washes with the appropriate solutions following the manufacturer's standard protocol. Fifty μl of acetonitrile was used to dehydrate the gel between reactions and gel pieces were air dried between steps. Peptides were extracted twice with 1% formic acid/2% acetonitrile in HPLC grade water for 30 minutes. Peptide extraction solutions were transferred to a THERMO-FAST® 96 well skirted PCR low profile plate (ABGene, Rochester, N.Y., USA) that had been cooled to 10-15° C. and covered with a 96-well plate lid (Perkin Elmer Life and Analytical Sciences, Boston, Mass., USA) to prevent evaporation. Plates were further stored at 4° C. until mass spectrometry analysis could be performed.

Peptide sequencing by tandem mass spectrometry. For peptide sequencing by tandem mass spectrometry, a Q-TOF MICRO™ hybrid orthogonal quadrupole time-of-flight mass spectrometer (WATERS® MICROMASS® MS Technologies, Milford, Mass., USA) was used for LC-MS/MS analysis. The Q-TOF MICRO™ mass spectrometer was fitted with an ULTIMATE™ capillary and nano-flow HPLC system (Dionex, Sunnyvale, Calif., USA) coupled to a FAMOS™ micro autosampler (Dionex, Sunnyvale, Calif., USA) and a SWITCHOS™ II column switching device (Dionex, Sunnyvale, Calif., USA) for concentrating and desalting samples.

Six μl of the recovered peptide solution from the in-gel digestion was loaded onto a guard column (300 μm ID×5 cm, C18 PEPMAP®, Dionex, Sunnyvale, Calif., USA) fitted in the injection loop and washed with 0.1% formic acid in water at 40 μl per minute for 2 minutes using a SWITCHOS™ II pump (Dionex, Sunnyvale, Calif., USA). Peptides were separated on a 75 μm ID×15 cm, C18, 3 μm, 100 Å PEPMAP® nanoflow fused capillary column (Dionex, Sunnyvale, Calif., USA) at a flow rate of 175 nl per minute from a split flow of 175 μl per minute using a NAN-75 calibrator (Dionex, Sunnyvale, Calif., USA). The linear elution gradient was 5% to 60% acetonitrile in 0.1% formic acid applied over a 45 minute period. The column eluent was monitored at 215 nm and introduced into the Q-TOF MICRO™ mass spectrometer through an electrospray ion source fitted with the nanospray interface. The mass spectrometer was fully microprocessor controlled using MASSLYNX™ software version 3.5 (WATERS® MICROMASS® MS Technologies, Milford, Mass., USA). Data was acquired in survey scan mode and from a mass range of 50 to 2000 m/z with switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to vary according to the mass and charge state of the eluting peptide and in the range of 10 to 60 volts. The acquired spectra were combined, smoothed, and centered in an automated fashion and a peak list generated. The generated peak list was searched against selected databases using PROTEINLYNX™ Global Server 1.1 software (WATERS® MICROMASS® MS Technologies, Milford, Mass., USA). Results from the PROTEINLYNX™ searches were evaluated and un-identified proteins were analyzed further by evaluating the MS/MS spectrums of each ion of interest and de novo sequence determined by identifying the y and b ion series and matching mass differences to the appropriate amino acid.

A 2D gel spot corresponding to an approximate molecular weight of 40 kDa and an approximate isoelectric point of 4.5 was in-gel digested with trypsin and subjected to de novo sequencing as described. A doubly charged tryptic peptide ion of 431.782 m/z was determined to be Gly-Pro-[Ile/Leu]-Ala-Tyr-[Ile-Leu]-Lys (amino acids 98 to 105 of SEQ ID NO: 2). A second doubly charged tryptic peptide ion of 570.976 m/z was determined to be His-Thr-[Ile/Leu]-Thr-Ser-Gly-Pro-Asp-Asp-Val-Met-Asp-Ala-Ser-His-Lys (amino acids 82 to 97 of SEQ ID NO: 2). A third doubly charged tryptic peptide ion of 825.9517 m/z was determined to be Val-Asp-Asp-Ala-[Ile/Leu]-Thr-Asp-Thr-Gly-[Ile/Leu]-Gly-Gly-Gly-Trp-Phe-Lys (amino acids 107 to 122 of SEQ ID NO: 2)

Example 2

Expressed Sequence Tags (EST) cDNA Library Construction

A two ml aliquot from a 24-hour liquid culture (50 ml of NNCYPmod supplemented with 1% glucose in a 250 ml flask incubated at 45° C., 200 rpm) of *Thielavia terrestris* NRRL 8126 was used to seed a 500 ml flask containing 100 ml of NNCYPmod medium supplemented with 2% SIGMACELL® Type 20 cellulose. The culture was incubated at 45° C., 200 rpm for 3 days. The mycelia were harvested by filtration through a Buchner funnel with a glass fiber prefilter (Nalgene, Rochester N.Y., USA), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of Fenazol (Ambion, Inc., Austin, Tex., USA) in a 50 ml FALCON® tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volume of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

The quality and quantity of the purified RNA was assessed with a 2100 Bioanalyzer (Agilent Technologies, Inc., Palo Alto, Calif., USA). Polyadenylated mRNA was isolated from 360 μg of total RNA with the aid of a POLY(A)PURIST™ MAG Kit (Ambion, Inc., Austin, Tex., USA) according to the manufacturer's instructions.

To create the cDNA library, a CLONEMINER™ Kit (Invitrogen, Carlsbad, Calif., USA) was employed to construct a directional library that does not require the use of restriction enzyme cloning, thereby reducing the number of chimeric clones and size bias.

To insure the successful synthesis of the cDNA, two reactions were performed in parallel with two different concentrations of mRNA (2.2 and 4.4 μg of poly(A)$^+$ mRNA). The mRNA samples were mixed with a Biotin-attB2-Oligo(dt) primer (CLONEMINER™ Kit, Invitrogen, Carlsbad, Calif., USA), 1× first strand buffer (Invitrogen, Carlsbad, Calif., USA), 2 μl of 0.1 M dithiothreitol (DTT), 10 mM of each dNTP, and water to a final volume of 18 and 16 μl, respectively.

The reaction mixtures were mixed carefully and then 2 and 4 μl of SUPERSCRIPT™ reverse transcriptase (Invitrogen, Carlsbad, Calif., USA) were added and incubated at 45° C. for 60 minutes to synthesize the first complementary strand. For second strand synthesis to each first strand reaction was added 30 μl of 5× second strand buffer (Invitrogen, Carlsbad, Calif., USA), 3 μl of 10 mM of each dNTP, 10 units of *E. coli* DNA ligase (Invitrogen, Carlsbad, Calif., USA), 40 units of *E. coli* DNA polymerase I (Invitrogen, Carlsbad, Calif., USA), and 2 units of *E. coli* RNase H (Invitrogen, Carlsbad, Calif., USA) in a total volume of 150 μl. The mixtures were then incubated at 16° C. for two hours. After the two-hour incubation 2 μl of T4 DNA polymerase (Invitrogen, Carlsbad, Calif., USA) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 μg of glycogen, 120 μl of 5 M ammonium acetate, and 660 μl of ethanol. After centrifugation at 12,000×g for 30 at 4° C. the cDNA pellets were washed with cold 70% ethanol, dried under vacuum for 2-3 minutes, and resuspended in 18 μl of DEPC-water. To each resuspended cDNA sample was added 10 μl of 5× adapted buffer, 10 μg of each of the attB1 adapters (provided with the CLONEMINER™ Kit), 7 μl of 0.1 M DTT, and 5 units of T4 DNA ligase.

Ligation reactions were incubated overnight at 16° C. Excess adapters were removed by size-exclusion chromatography in 1 ml of SEPHACRYL™ S-500 HR resin (Amersham Biosciences, Piscataway, N.J., USA). Column fractions were collected according to the kit's instructions and fractions 3 to 14 were analyzed with an AGILENT® 2100 Bioanalyzer to determine the fraction at which the attB1 adapters started to elute. This analysis showed that the adapters started eluting around fraction 10 or 11. For the first library fractions 6 to 11 were pooled and for the second library fractions 4-11 were pooled.

Cloning of the cDNA was performed by homologous DNA recombination according to GATEWAY® Technology (Invitrogen, Carlsbad, Calif., USA) using BP CLONASE™ (Invitrogen, Carlsbad, Calif., USA) as the recombinase. Each BP CLONASE™ recombination reaction contained approximately 70 ng of attB-flanked-cDNA, 250 ng of pDONR™ 222, 2 μl of 5×BP CLONASE™ buffer, 2 μl of TE, and 3 μl of BP CLONASE™. Recombination reactions were incubated at 25° C. overnight.

Heat-inactivated BP recombination reactions were then divided into 6 aliquots and electroporated into ELECTROMAX™ DH10B electrocompetent cells (Invitrogen, Carlsbad, Calif., USA) using a GENE PULSER® II Electroporation System (Bio-Rad, Hercules, Calif., USA) with the following parameters: voltage: 2.0 kV, resistance: 200Ω, capacity 25 μF. Electroporated cells were resuspended in 1 ml of SOC medium and incubated at 37° C. for 60 minutes with constant shaking (200 rpm). After the incubation period, the transformed cells were pooled and mixed 1:1 with freezing medium. A 200 μl aliquot was removed for library titration and then the rest of each library was aliquoted into 1.8 ml cryovials (Wheaton Science Products, Millville, N.J., USA) and stored frozen at −80° C.

Four serial dilutions of each library were prepared: 1/100, 1/1000, $1/10^4$, $1/10^5$. From each dilution 100 μl were plated onto 150 mm LB plates supplemented with 50 μg of kanamycin per ml and incubated at 37° C. overnight. The number of colonies on each dilution plate were counted and used to calculate the total number of transformants in each library.

The first library was shown to have approximately 5.4 million independent clones and the second library was show to have approximately 9 million independent clones.

Example 3

Template Preparation and Nucleotide Sequencing of cDNA Clones

Aliquots from both libraries were mixed and plated onto 25×25 cm LB plates supplemented with 50 μg of kanamycin per ml. Individual colonies were arrayed onto 96-well plates containing 100 μl of LB medium supplemented with 50 μg of kanamycin per ml with the aid of a QPix Robot (Genetix Inc., Boston, Mass., USA). Forty-five 96-well plates were obtained for a total of 4320 individual clones. The plates were incubated overnight at 37° C. with shaking at 200 rpm. After incubation, 100 μl of sterile 50% glycerol was added to each well. The transformants were replicated with the aid of a 96-pin tool (Boekel, Feasterville, Pa., USA) into secondary, deep-dish 96-well microculture plates (Advanced Genetic Technologies Corporation, Gaithersburg, Md., USA) containing 1 ml of MAGNIFICENT BROTH™ (MacConnell Research, San Diego, Calif., USA) supplemented with 50 μg of kanamycin per ml in each well. The primary microtiter plates were stored frozen at −80° C. The secondary deep-dish plates were incubated at 37° C. overnight with vigorous agitation (300 rpm) on a rotary shaker. To prevent spilling and cross-contamination, and to allow sufficient aeration, each secondary culture plate was covered with a polypropylene pad (Advanced Genetic Technologies Corporation, Gaithersburg, Md., USA) and a plastic microtiter dish cover. Plasmid DNA was prepared with a Robot-Smart 384 (MWG Biotech Inc., High Point, N.C., USA) and MONTAGE™ Plasmid Miniprep96 Kit (Millipore, Billerica, Mass., USA).

Sequencing reactions were performed using a BIGDYE® Terminator v3.0 Ready Reaction Cycle Sequencing Kit (Applied Biosystems, Inc., Foster City, Calif., USA) with terminator chemistry (Giesecke et al., 1992, *Journal of Virology Methods* 38: 47-60) and a M13 Forward (−20) sequencing primer shown below.

```
5'-GTAAAACGACGGCCAG-3'     (SEQ ID NO: 3)
```

The sequencing reactions were performed in a 384-well format with a Robot-Smart 384 (MWG Biotech Inc., High Point, N.C., USA) as well as the terminator removal with a MULTISCREEN® Seq384 Sequencing Clean-up Kit (Millipore, Billerica, Mass., USA). Reactions contained 6 μl of plasmid DNA and 4 μl of sequencing master-mix containing 1 μl of 5× sequencing buffer (Millipore, Billerica, Mass., USA), 1 μl of BIGDYE® terminator (Applied Biosystems, Inc., Foster City, Calif., USA), 1.6 pmoles of M13 forward primer, and 1 μl of water. Single-pass DNA sequencing was performed with an ABI PRISM® 3700 DNA Sequencer (Applied Biosystems, Foster City, Calif., USA).

Example 4

Analysis of DNA Sequence Data of cDNA Clones

Base calling, quality value assignment, and vector trimming were performed with the assistance of PHRED/PHRAP software (University of Washington, Seattle, Wash., USA). Clustering analysis of the ESTs was performed with a Transcript Assembler v. 2.6.2. software (Paracel, Inc., Pasadena, Calif., USA). Analysis of the EST clustering indicated the presence of 395 independent clusters.

Sequence homology analysis of the assembled EST sequences against various databases, e.g., PIR, was performed with the Blastx program (Altschul et. al., 1990, *J. Mol. Biol.* 215:403-410) on a 32-node Linux cluster (Paracel, Inc., Pasadena, Calif., USA) using the BLOSUM 62 matrix (Henikoff, 1992, *Proc. Natl. Acad. Sci. USA* 89: 10915-10919) From these, 246 had hits to known genes in either the public or private protein databases and 149 had no significant hits against these databases. Among these 246 genes, 13 had hits against known glycosyl hydrolase genes.

Example 5

Identification of cDNA Clones Encoding a Family 61 Polypeptide Having Cellulolytic Enhancing Activity (GH61F)

A cDNA clone encoding a Family 61 polypeptide having cellulolytic enhancing activity (GH61F) was initially identified by its identity to a Family 61 protein from *Neurospora crassa* (UniProt Q7S439). This initial analysis indicated that the two proteins were 57.67% identical at the protein level over a 211 amino acid (663 basepairs) stretch.

After this initial identification clone Tter18A8 was retrieved from the original frozen stock plate and streaked onto a LB plate supplemented with 50 μg of kanamycin per ml. The plate was incubated overnight at 37° C. and the next day a single colony from the plate was used to inoculate 3 ml of LB supplemented with 50 μg of kanamycin per ml. The liquid culture was incubated overnight at 37° C. and plasmid DNA was prepared with a BIOROBOT® 9600 (QIAGEN Inc., Valencia, Calif., USA). Clone Tter08C4 plasmid DNA was sequenced again with BIGDYE® terminator chemistry as described above, using the M13 forward and a Poly-T primer shown below to sequence the 3' end of the clone.

```
5'-TTTTTTTTTTTTTTTTTTTTTTTVN-3'    (SEQ ID NO: 4)
```

wherein V=G, A, C and N=G, A, C, T

Blastp homology analysis of the new sequence information indicated that the protein encoded by clone Tter18A8 was similar to a *Neurospora crassa* hypothetical protein NCU02240.1 (UniRef Q7S439). These proteins were 74% identical over a 316 amino acid stretch.

Analysis of the deduced protein sequence of clone 18A8 with the Interproscan program (Zdobnov and Apweiler, 2001, *Bioinformatics* 17: 847-848) showed that the gene encoded by clone 18A8 contained the sequence signature of Family 61 proteins. This sequence signature known as the Pfam pattern PF03443 (Bateman, A. et al., 2002, *Nucleic Acids Research* 30: 276-280) was found 119 amino acids from the starting amino acid methionine confirming that clone Tter18A8 encodes a *Thielavia terrestris* Family 61 protein. This analysis also indicated that this protein contains a fungal cellulose binding domain (34 amino acids long) located 283 amino acids from the starting amino acid methionine.

The cDNA sequence (SEQ ID NO: 1) and deduced amino acid sequence (SEQ ID NO: 2) are shown in FIG. 1. The cDNA clone encodes a polypeptide of 317 amino acids. The % G+C content of the cDNA clone of the gene is 64.9% and of the mature protein coding region (nucleotides 46 to 955 of SEQ ID NO: 1) is also 64.9%. Using the SignalP software program (Nielsen et al., 1997, *Protein Engineering* 10:1-6), a signal peptide of 15 residues was predicted. The predicted mature protein contains 302 amino acids with a molecular mass of 31.14 kDa.

A comparative alignment of Family 61 sequences was determined using the Clustal W method (Higgins, 1989, supra) using the AlignX module of the vector NTI Advance 10.3 software (Invitrogen, Carlsbad, Calif., USA) with a blosum62mt2 scoring matrix and the following multiple alignment parameters: K-tuple size 1; best diagonals 5; window size 5; gap penalty 5; gap opening penalty 10; gap extension penalty 0.1. The alignment showed that the deduced amino acid sequence of the mature *Thielavia terrestris* gh61f gene shares 43% identity to the mature region of the *Thielavia terrestris* Cel61G polypeptide having cellulolytic enhancing activity (WO 2005/074647).

Once the identity of clone Tter18A8 was confirmed a 0.5 μl aliquot of plasmid DNA from this clone designated pTter61F (FIG. 2) was transferred into a vial of ONE SHOT® *E. coli* TOP10 cells (Invitrogen, Carlsbad, Calif., USA), gently mixed, and incubated on ice for 10 minutes. The cells were then heat-shocked at 42° C. for 30 seconds and incubated again on ice for 2 minutes. The cells were resuspended in 250 μl of SOC medium and incubated at 37° C. for 60 minutes with constant shaking (200 rpm). After the incubation period, two 30 μl aliquots were plated onto LB plates supplemented with 50 μg of kanamycin per ml and incubated overnight at 37° C. The next day a single colony was picked and streaked onto a 1.8 ml cryovial containing about 1.5 ml of LB agarose supplemented with 50 μg of kanamycin per ml. The vial was sealed with PETRISEAL™ (Diversified Biotech, Boston, Mass., USA) and deposited with the Agricultural Research Service Patent Culture Collection, Northern Regional Research Center, 1815 University Street, Peoria, Ill., USA, as NRRL B-50044, with a deposit date of May 25, 2007.

Example 6

Cloning of the Family gh61f Gene into an *Aspergillus oryzae* Expression Vector Two synthetic oligonucleotide primers, shown below, were designed to PCR amplify the full-length open reading frame from *Thielavia terrestris* EST Tter18A8 encoding a Family GH61F polypeptide having cellulolytic enhancing activity. An IN-FUSION® PCR Cloning Kit (BD Biosciences, Palo Alto, Calif., USA) was used to clone the fragment directly into plasmid pAILo2 (WO 2004/099228).

Forward primer:
(SEQ ID NO: 5)
5'-ACTGGATTTACCATGAAGGGCCTCAGCCTCCTCG-3'

Reverse primer:
(SEQ ID NO: 6)
5'-TCACCTCTAGTTAATTAATTACTGGCATTGCGAGTAATAG-3'

Bold letters represent coding sequence. The remaining sequence contains sequence identity compared with the insertion sites of pAILo2.

Fifty picomoles of each of the primers above were used in a PCR reaction containing 50 ng of pTter18A8 DNA, 1× Pfx Amplification Buffer (Invitrogen, Carlsbad, Calif., USA), 6 μl of 10 mM blend of dATP, dTTP, dGTP, and dCTP, 2.5 units of PLATINUM® Pfx DNA Polymerase (Invitrogen, Carlsbad, Calif., USA), 1 μl of 50 mM $MgSO_4$, and 5 μl of 10× pCRx Enhancer Solution (Invitrogen, Carlsbad, Calif., USA) in a final volume of 50 μl. An EPPENDORF® MASTERCYCLER® 5333 (Eppendorf Scientific, Inc., Westbury, N.Y., USA) was used to amplify the fragment programmed for one cycle at 98° C. for 2 minutes; and 35 cycles each at 94° C. for 30 seconds, 62.1° C. for 30 seconds, and 68° C. for 1.0 minute. After the 35 cycles, the reaction was incubated at 68° C. for 10 minutes and then cooled at 10° C. until further processed. A 984 bp PCR reaction product was isolated on a 0.8% SEAKEM® GTG® agarose gel (Cambrex Bioproducts, East Rutherford, N.J., USA) using 40 mM Tris base-20 mM sodium acetate-1 mM disodium EDTA (TAE) buffer and 0.1 μg of ethidium bromide per ml. The DNA band was visualized with the aid of a DARK READER® (Clare Chemical Research, Dolores, Colo., USA) to avoid UV-induced mutations. The DNA band was excised with a disposable razor blade and purified with an ULTRAFREE®-DA spin cup (Millipore, Billerica, Mass., USA) according to the manufacturer's instructions.

Figure 3:
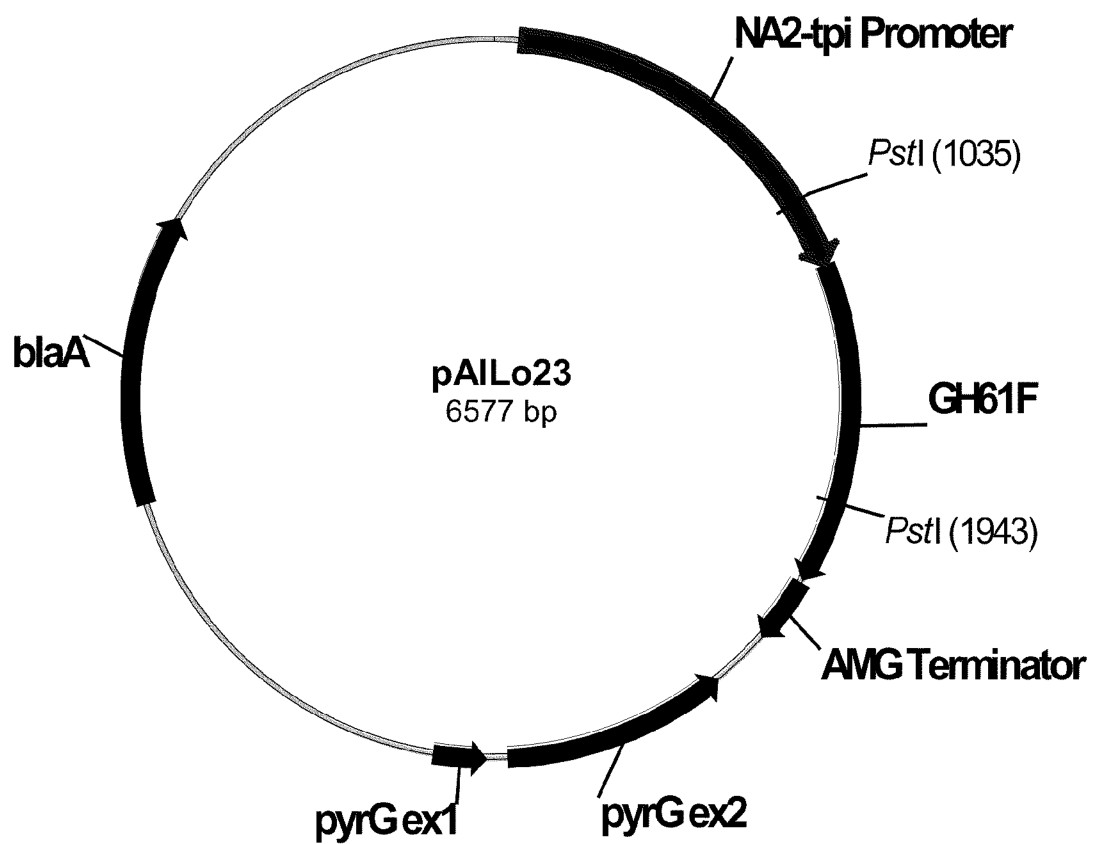
FIG. 3 shows a restriction map of pAILo23.

Plasmid pAILo2 was linearized by digestion with Nco I and Pac I. The fragment was purified by gel electrophoresis and ultrafiltration as described above. Cloning of the purified PCR fragment into the linearized and purified pAILo2 was performed with an IN-FUSION® PCR Cloning Kit. The reaction (20 μl) contained 2 μl of 1×IN-FUSION® Buffer, 2 μl of 1×BSA, 1 μl of IN-FUSION® enzyme (diluted 1:10), 100 ng of pAILo2 digested with Nco I and Pac I, and 100 ng of the *Thielavia terrestris* gh61f purified PCR product. The reaction was incubated at room temperature for 30 minutes. A 2 μl sample of the reaction was used to transform *E. coli* XL10 SOLOPACK® Gold cells (Stratagene, La Jolla, Calif., USA) according to the manufacturer's instructions. After a recovery period, two 100 μl aliquots from the transformation reaction were plated onto 150 mm 2×YT plates supplemented with 100 μg of ampicillin per ml. The plates were incubated overnight at 37° C. Four putative recombinant clones were collected from the selection plates and plasmid DNA was prepared from each one using a BIOROBOT® 9600 (QIAGEN Inc., Valencia, Calif., USA). Clones were analyzed by Pst I restriction digest. Two clones that had the expected restriction digest pattern were then sequenced to confirm that there were no mutations in the cloned insert. Sequencing was performed with an ABI PRISM® 3130xl DNA Sequencer (Applied Biosystems, Foster City, Calif., USA). Clone #3 was selected and designated pAILo23 (FIG. 3).

Example 7

Expression of the *Thielavia terrestris* Family gh61f Gene in *Aspergillus oryzae* JaL250

*Aspergillus oryzae* JaL250 (WO 99/61651) protoplasts were prepared according to the method of Christensen et al., 1988, *Bio/Technology* 6: 1419-1422. Five micrograms of pAILo23 (as well as pAILo2 as a plasmid control) were used to transform the *Aspergillus oryzae* JaL250 protoplasts.

The transformation of *Aspergillus oryzae* JaL250 with pAILo22 yielded about 50 transformants. Eight transformants were isolated to individual PDA plates and incubated for five days at 34° C.

Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Seven and a half micro-liters of each supernatant were mixed with an equal volume of 2× loading buffer (10% β-mercaptoethanol) and loaded onto a 1.5 mm 8%-16% Tris-Glycine SDS-PAGE gel and stained with BIO-SAFE™ Coomassie Blue G250 (Bio-Rad, Hercules, Calif., USA). SDS-PAGE profiles of the culture broths showed that seven out of eight transformants had a new protein band of approximately 45 kDa. Transformant number 4 was selected for further studies and designated *Aspergillus oryzae* JaL250AILo23.

Example 8

Fermentation of *Aspergillus oryzae* JaL250AILo23

One hundred ml of a shake flask medium was added to a 500 ml shake flask. The shake flask medium was composed per liter of 50 g of sucrose, 10 g of $KH_2PO_4$, 0.5 g of $CaCl_2$, 2 g of $MgSO_4.7H_2O$, 2 g of $K_2SO_4$, 2 g of urea, 10 g of yeast extract, 2 g of citric acid, and 0.5 ml of trace metals solution. The trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. The shake flask was inoculated with two plugs from a solid plate culture of *Aspergillus oryzae* JaL250AILo23 and incubated at 34° C. on an orbital shaker at 200 rpm for 24 hours.

Fifty ml of the shake flask broth were used to inoculate a 3 liter fermentation vessel containing 1.8 liters of a fermentation batch medium composed per liter of 10 g of yeast extract, 24 g of sucrose, 5 g of $(NH_4)_2SO_4$, 2 g of $KH_2PO_4$, 0.5 g of $CaCl_2.2H_2O$, 2 g of $MgSO_4.7H_2O$, 1 g of citric acid, 2 g of $K_2SO_4$, 0.5 ml of anti-foam, and 0.5 ml of trace metals solution. Trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. Fermentation feed medium was composed of maltose and antifoam. The fermentation feed medium was dosed at a rate of 0 to 4.4 g/l/hr for a period of 185 hours. The fermentation vessel was maintained at a temperature of 34° C. and pH was controlled to a set-point of 6.1+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered and stored at 35 to 40° C.

Example 9

Construction of pMJ04 Expression Vector

Expression vector pMJ04 was constructed by PCR amplifying the *Trichoderma reesei* exocellobiohydrolase 1 gene (cbh1, CEL7A) terminator from *Trichoderma reesei* RutC30 genomic DNA using primers 993429 (antisense) and 993428 (sense) shown below. The antisense primer was engineered to have a Pac I site at the 5'-end and a Spe I site at the 3'-end of the sense primer.

```
Primer 993429 (antisense):
                                    (SEQ ID NO: 7)
5'-AACGTTAATTAAGGAATCGTTTTGTGTTT-3'

Primer 993428 (sense):
                                    (SEQ ID NO: 8)
5'-AGTACTAGTAGCTCCGTGGCGAAAGCCTG-3'
```

*Trichoderma reesei* RutC30 genomic DNA was isolated using a DNEASY® Plant Maxi Kit (QIAGEN Inc., Valencia, Calif., USA).

The amplification reactions (50 μl) were composed of 1× ThermoPol Reaction Buffer (New England Biolabs, Beverly, Mass., USA), 0.3 mM dNTPs, 100 ng of *Trichoderma reesei* RutC30 genomic DNA, 0.3 μM primer 993429, 0.3 μM primer 993428, and 2 units of Vent DNA polymerase (New England Biolabs, Beverly, Mass., USA). The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 229 bp product band was excised from the gel and purified using a QIAQUICK® Gel Extraction Kit (QIAGEN Inc., Valencia, Calif., USA) according to the manufacturer's instructions.

Figure 4:
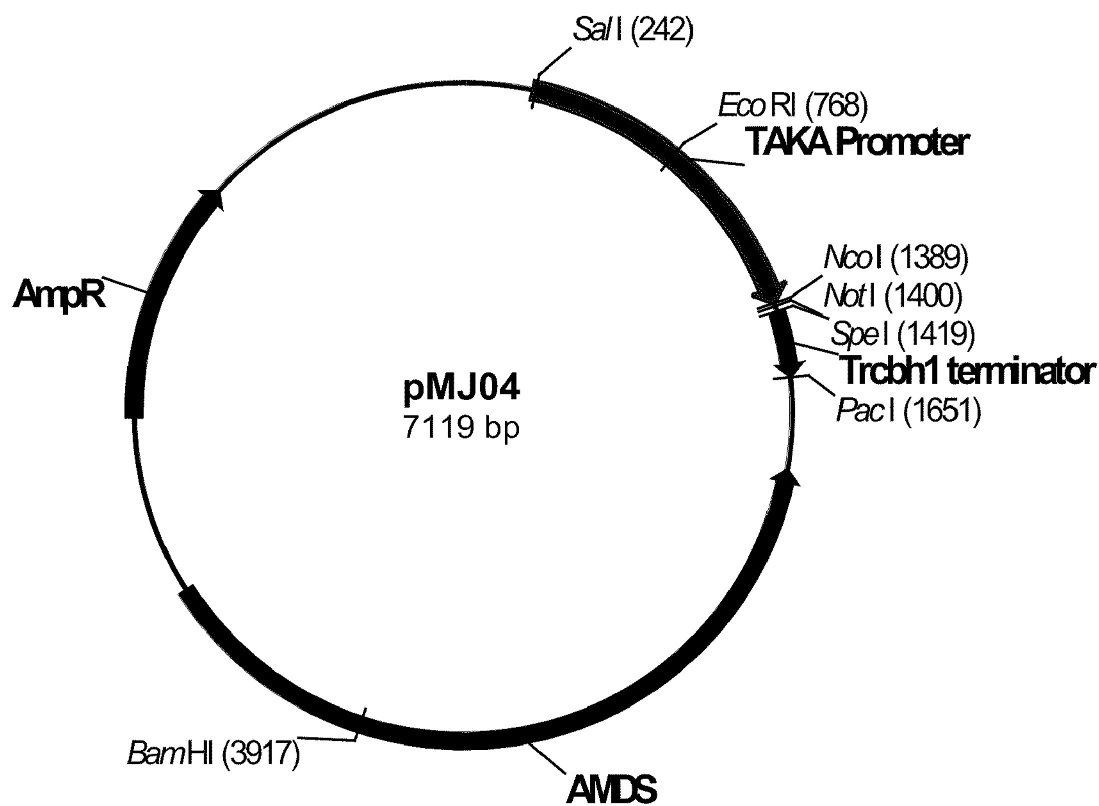
FIG. 4 shows a restriction map of pMJ04.

The resulting PCR fragment was digested with Pac I and Spe I and ligated into pAILo1 (WO 05/067531) digested with the same restriction enzymes using a Rapid Ligation Kit (Roche, Indianapolis, Ind., USA), to generate pMJ04 (FIG. 4).

Example 10

Construction of pCaHj568

Plasmid pCaHj568 was constructed from pCaHj170 (U.S. Pat. No. 5,763,254) and pMT2188. Plasmid pCaHj170 comprises the *Humicola insolens* endoglucanase V (CEL45A) full-length coding region (SEQ ID NO: 9, which encodes the amino acid sequence of SEQ ID NO: 10). Construction of pMT2188 was initiated by PCR amplifying the pUC19 origin of replication from pCaHj483 (WO 98/00529) using primers 142779 and 142780 shown below. Primer 142780 introduces a Bbu I site in the PCR fragment.

142779:

(SEQ ID NO: 11)
5'-TTGAATTGAAAATAGATTGATTTAAAACTTC-3'

142780:

(SEQ ID NO: 12)
5'-TTGCATGCGTAATCATGGTCATAGC-3'

An EXPAND® PCR System (Roche Molecular Biochemicals, Basel, Switzerland) was used following the manufacturer's instructions for this amplification. PCR products were separated on an agarose gel and an 1160 bp fragment was isolated and purified using a Jetquick Gel Extraction Spin Kit (Genomed, Wielandstr, Germany).

The URA3 gene was amplified from the general *Saccharomyces cerevisiae* cloning vector pYES2 (Invitrogen, Carlsbad, Calif., USA) using primers 140288 and 142778 shown below using an EXPAND® PCR System. Primer 140288 introduced an Eco RI site in the PCR fragment.

140288:

(SEQ ID NO: 13)
5'-TTGAATTCATGGGTAATAACTGATAT-3'

142778:

(SEQ ID NO: 14)
5'-AAATCAATCTATTTTCAATTCAATTCATCATT-3'

PCR products were separated on an agarose gel and an 1126 bp fragment was isolated and purified using a Jetquick Gel Extraction Spin Kit.

The two PCR fragments were fused by mixing and amplified using primers 142780 and 140288 shown above by the overlap splicing method (Horton et al., 1989, *Gene* 77: 61-68). PCR products were separated on an agarose gel and a 2263 bp fragment was isolated and purified using a Jetquick Gel Extraction Spin Kit.

Figure 5:
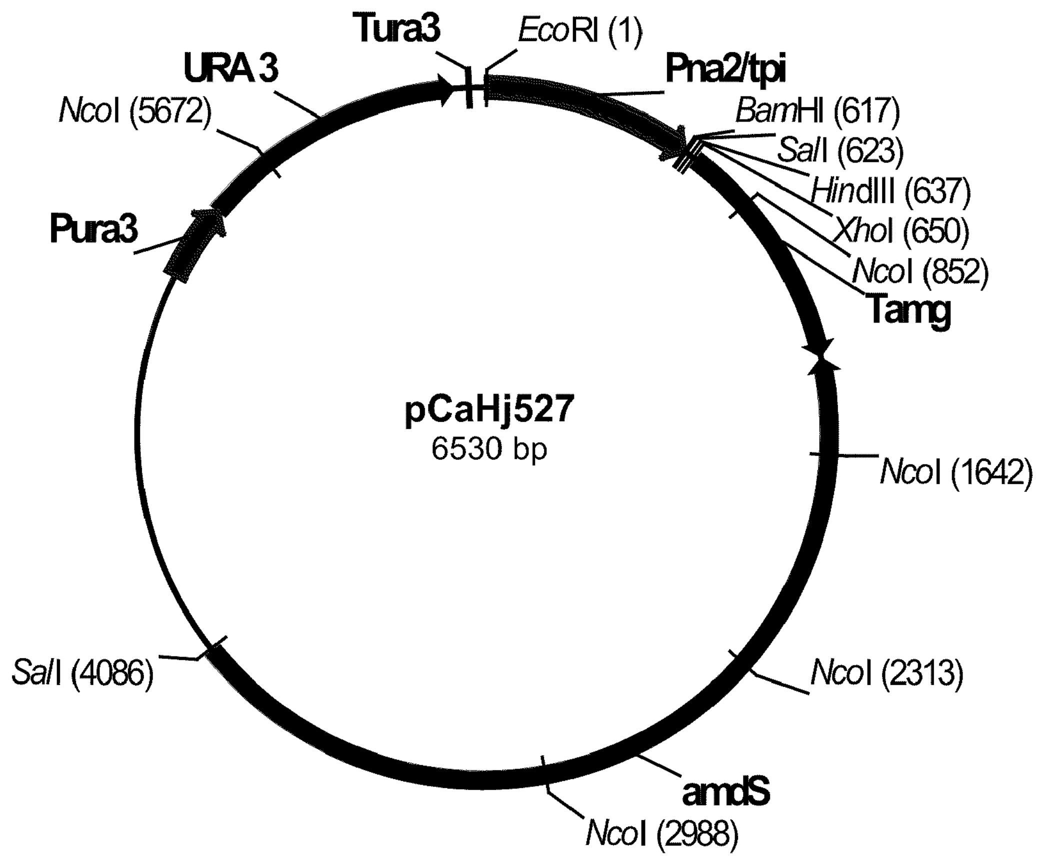
FIG. 5 shows a restriction map of pCaHj527.

The resulting fragment was digested with Eco RI and Bbu I and ligated using standard protocols to the largest fragment of pCaHj483 digested with the same restriction enzymes. The ligation mixture was transformed into pyrF-negative *E. coli* strain DB6507 (ATCC 35673) made competent by the method of Mandel and Higa, 1970, *J. Mol. Biol.* 45: 154. Transformants were selected on solid M9 medium (Sambrook et al., 1989, *Molecular Cloning, A Laboratory Manual*, 2nd edition, Cold Spring Harbor Laboratory Press) supplemented per liter with 1 g of casaminoacids, 500 μg of thiamine, and 10 mg of kanamycin. A plasmid from one transformant was isolated and designated pCaHj527 (FIG. 5).

The NA2-tpi promoter present on pCaHj527 was subjected to site-directed mutagenesis by PCR using an EXPAND® PCR System according to the manufacturer's instructions. Nucleotides 134-144 were converted from GTACTAAAACC (SEQ ID NO: 15) to CCGTTAAATTT (SEQ ID NO: 16) using mutagenic primer 141223 shown below.

Primer 141223:

(SEQ ID NO: 17)
5'-GGATGCTGTTGACTCCGGAAATTTAACGGTTTGGTCTTGCATCCC-3'

Nucleotides 423-436 were converted from ATGCAATTTAAACT (SEQ ID NO: 18) to CGGCAATTTAACGG (SEQ ID NO: 19) using mutagenic primer 141222 shown below.

Primer 141222:

(SEQ ID NO: 20)
5'-GGTATTGTCCTGCAGACGGCAATTTAACGGCTTCTGCGAATCGC-3'

Figure 6:
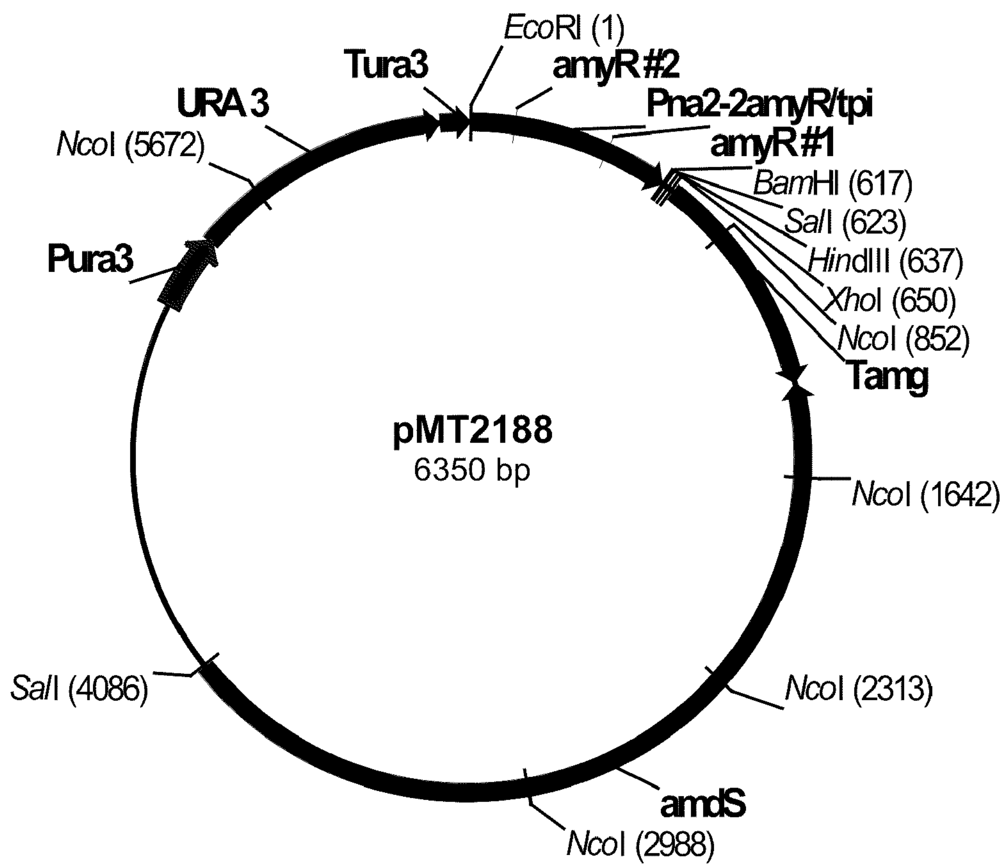
FIG. 6 shows a restriction map of pMT2188.

The resulting plasmid was designated pMT2188 (FIG. 6).

Figure 7:
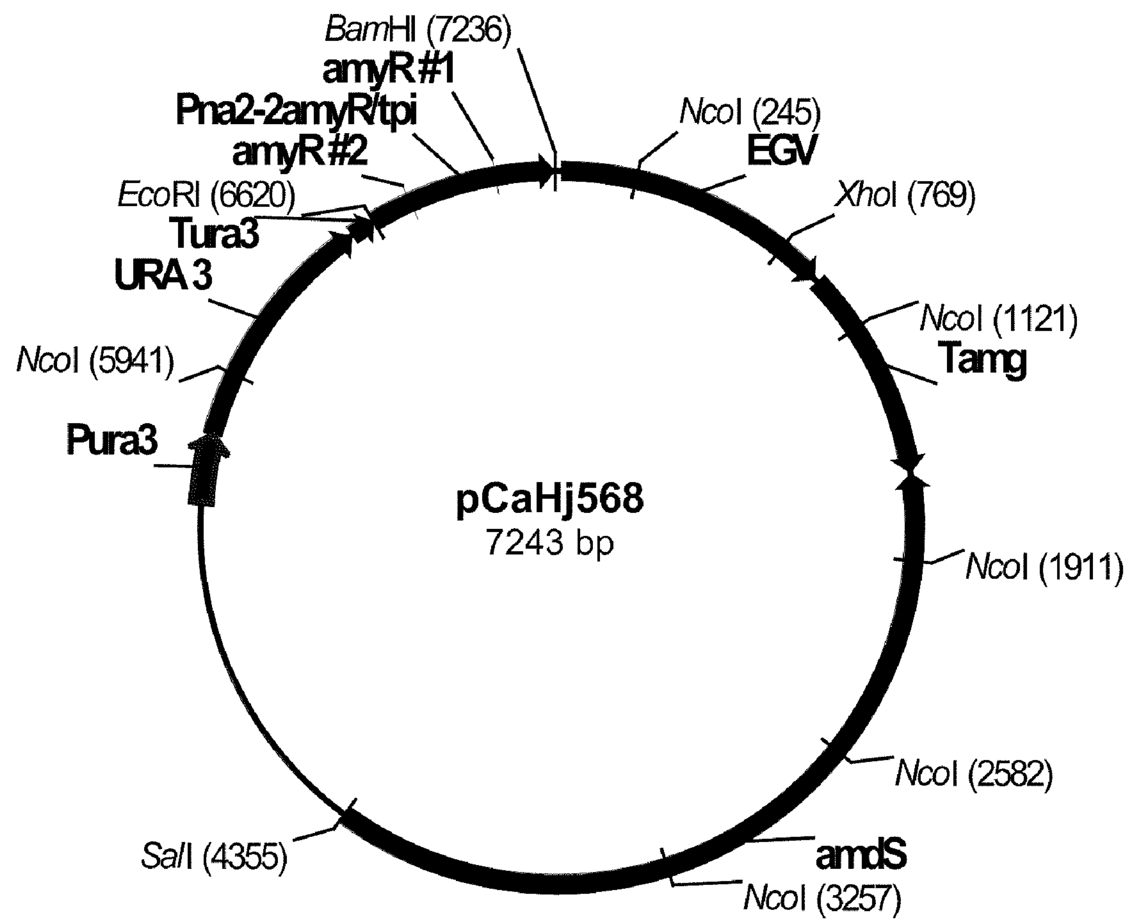
FIG. 7 shows a restriction map of pCaHj568.

The *Humicola insolens* endoglucanase V coding region was transferred from pCaHj170 as a Bam HI-Sal I fragment into pMT2188 digested with Bam HI and Xho I to generate pCaHj568 (FIG. 7). Plasmid pCaHj568 comprises a mutated NA2-tpi promoter operably linked to the *Humicola insolens* endoglucanase V full-length coding sequence.

Example 11

Construction of pMJ05

Plasmid pMJ05 was constructed by PCR amplifying the 915 bp *Humicola insolens* endoglucanase V full-length coding region from pCaHj568 using primers HiEGV-F and HiEGV-R shown below.

HiEGV-F (sense):

(SEQ ID NO: 21)
5'-AAGCTTAAGCATGCGTTCCTCCCCCCTCC-3'

HiEGV-R (antisense):

(SEQ ID NO: 22)
5'-CTGCAGAATTCTACAGGCACTGATGGTACCAG-3'

The amplification reactions (50 μl) were composed of 1× ThermoPol Reaction Buffer, 0.3 mM dNTPs, 10 ng/μl of pCaHj568, 0.3 μM HiEGV-F primer, 0.3 μM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 937 bp product band was excised from the gel and purified using a QIAQUICK® Gel Extraction Kit according to the manufacturer's instructions.

The 937 bp purified fragment was used as template DNA for subsequent amplifications using the following primers:

HiEGV-R (antisense):

(SEQ ID NO: 23)
5'-CTGCAGAATTCTACAGGCACTGATGGTACCAG-3'

HiEGV-F-overlap (sense):

(SEQ ID NO: 24)
5'-*ACCGCGGACTGCGCATC*<u>ATGCGTTCCTCCCCCCTCC</u>-3'

Primer sequences in italics are homologous to 17 bp of the *Trichoderma reesei* cellobiohydrolase I gene (cbh1) promoter and underlined primer sequences are homologous to 29 bp of the *Humicola insolens* endoglucanase V coding region. A 36 bp overlap between the promoter and the coding sequence allowed precise fusion of a 994 bp fragment comprising the *Trichoderma reesei* cbh1 promoter to the 918 bp fragment comprising the *Humicola insolens* endoglucanase V coding region.

The amplification reactions (50 μl) were composed of 1× ThermoPol Reaction Buffer, 0.3 mM dNTPs, 1 μl of the purified 937 bp PCR fragment, 0.3 μM HiEGV-F-overlap primer, 0.3 μM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 945 bp product band was excised from the gel and purified using a QIAQUICK® Gel Extraction Kit according to the manufacturer's instructions.

A separate PCR was performed to amplify the *Trichoderma reesei* cbh1 promoter sequence extending from 994 bp upstream of the ATG start codon of the gene from *Trichoderma reesei* RutC30 genomic DNA using the primers shown below (the sense primer was engineered to have a Sal I restriction site at the 5'-end). *Trichoderma reesei* RutC30 genomic DNA was isolated using a DNEASY® Plant Maxi Kit.

```
TrCBHIpro-F (sense):
                                        (SEQ ID NO: 25)
5'-AAACGTCGACCGAATGTAGGATTGTTATC-3'

TrCBHIpro-R (antisense):
                                        (SEQ ID NO: 26)
5'-GATGCGCAGTCCGCGGT-3'
```

The amplification reactions (50 μl) were composed of 1× ThermoPol Reaction Buffer, 0.3 mM dNTPs, 100 ng/μl *Trichoderma reesei* RutC30 genomic DNA, 0.3 μM TrCBHIpro-F primer, 0.3 μM TrCBHIpro-R primer, and 2 units of Vent DNA polymerase. The reactions were incubated in an EPPENDORF® MASTERCYCLER® 5333 programmed for 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAQUICK® Gel Extraction Kit according to the manufacturer's instructions.

The purified 998 bp PCR fragment was used as template DNA for subsequent amplifications using the primers shown below.

```
TrCBHIpro-F:
                                        (SEQ ID NO: 27)
5'-AAACGTCGACCGAATGTAGGATTGTTATC-3'

TrCBHIpro-R-overlap:
                                        (SEQ ID NO: 28)
5'-GGAGGGGGGAGGAACGCATGATGCGCAGTCCGCGGT-3'
```

Sequences in italics are homologous to 17 bp of the *Trichoderma reesei* cbh1 promoter and underlined sequences are homologous to 29 bp of the *Humicola insolens* endoglucanase V coding region. A 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V full-length coding region.

The amplification reactions (50 μl) were composed of 1× ThermoPol Reaction Buffer, 0.3 mM dNTPs, 1 μl of the purified 998 bp PCR fragment, 0.3 μM TrCBH1pro-F primer, 0.3 μM TrCBH1pro-R-overlap primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1017 bp product band was excised from the gel and purified using a QIAQUICK® Gel Extraction Kit according to the manufacturer's instructions.

The 1017 bp *Trichoderma reesei* cbh1 promoter PCR fragment and the 945 bp *Humicola insolens* endoglucanase V PCR fragment were used as template DNA for subsequent amplification using the following primers to precisely fuse the 994 bp cbh1 promoter to the 918 bp endoglucanase V full-length coding region using overlapping PCR.

```
TrCBHIpro-F:
                                        (SEQ ID NO: 29)
5'-AAACGTCGACCGAATGTAGGATTGTTATC-3'

HiEGV-R:
                                        (SEQ ID NO: 30)
5'-CTGCAGAATTCTACAGGCACTGATGGTACCAG-3'
```

The amplification reactions (50 μl) were composed of 1× ThermoPol Reaction Buffer, 0.3 mM dNTPs, 0.3 μM TrCBH1pro-F primer, 0.3 μM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1926 bp product band was excised from the gel and purified using a QIAQUICK® Gel Extraction Kit according to the manufacturer's instructions.

Figure 8:
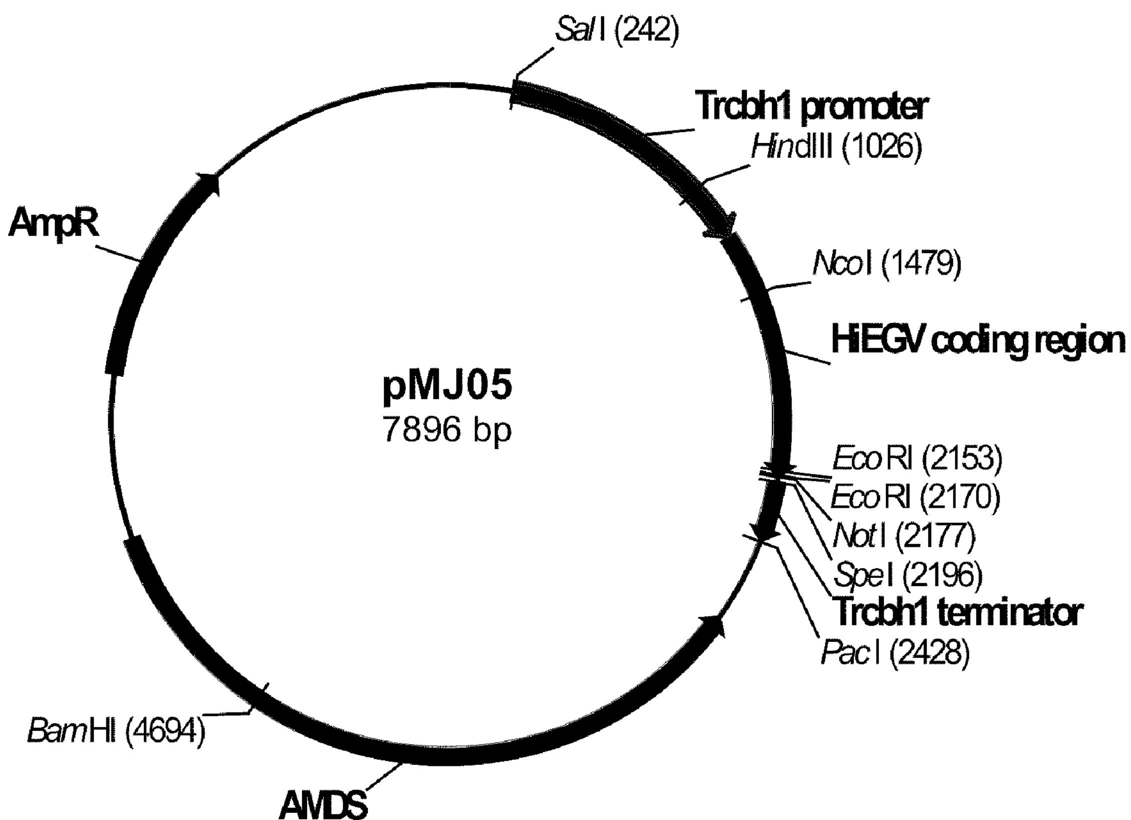
FIG. 8 shows a restriction map of pMJ05.

The resulting 1926 bp fragment was cloned into a pCR®-Blunt-II-TOPO® vector (Invitrogen, Carlsbad, Calif., USA) using a ZEROBLUNT® TOPO® PCR Cloning Kit (Invitrogen, Carlsbad, Calif., USA) following the manufacturer's protocol. The resulting plasmid was digested with Not I and Sal I and the 1926 bp fragment was gel purified using a QIAQUICK® Gel Extraction Kit and ligated using T4 DNA ligase (Roche, Indianapolis, Ind., USA) into pMJ04, which was also digested with the same two restriction enzymes, to generate pMJ05 (FIG. 8). Plasmid pMJ05 comprises the *Trichoderma reesei* cellobiohydrolase I promoter and terminator operably linked to the *Humicola insolens* endoglucanase V full-length coding sequence.

Example 12

Construction of pSMai130 Expression Vector

A 2586 bp DNA fragment spanning from the ATG start codon to the TAA stop codon of the *Aspergillus oryzae* beta-glucosidase full-length coding sequence (SEQ ID NO: 31 for cDNA sequence and SEQ ID NO: 32 for the deduced amino acid sequence; *E. coli* DSM 14240) was amplified by PCR from pJaL660 (WO 2002/095014) as template with primers 993467 (sense) and 993456 (antisense) shown below. A Spe I site was engineered at the 5' end of the antisense primer to facilitate ligation. Primer sequences in italics are homologous to 24 bp of the *Trichoderma reesei* cbh1 promoter and underlined sequences are homologous to 22 bp of the *Aspergillus oryzae* beta-glucosidase coding region.

```
Primer 993467:
                                        (SEQ ID NO: 33)
5'-ATAGTCAACCGCGGACTGCGCATCATGAAGCTTGGTTGGATCGAGG-
3'

Primer 993456:
                                        (SEQ ID NO: 34)
5'-ACTAGTTTACTGGGCCTTAGGCAGCG-3'
```

The amplification reactions (50 μl) were composed of Pfx Amplification Buffer (Invitrogen, Carlsbad, Calif., USA), 0.25 mM dNTPs, 10 ng of pJaL660, 6.4 μM primer 993467, 3.2 μM primer 993456, 1 mM $MgCl_2$, and 2.5 units of Pfx DNA polymerase (Invitrogen, Carlsbad, Calif., USA). The reactions were incubated in an EPPENDORF® MASTERCYCLER® 5333 programmed for 30 cycles each for 60 seconds at 94° C., 60 seconds at 55° C., and 180 seconds at 72° C. (15 minute final extension). The reaction products were isolated on a 1.0% agarose gel using TAE buffer where a 2586 bp product band was excised from the gel and purified using a QIAQUICK® Gel Extraction Kit according to the manufacturer's instructions.

A separate PCR was performed to amplify the *Trichoderma reesei* cbh1 promoter sequence extending from 1000 bp upstream of the ATG start codon of the gene, using primer 993453 (sense) and primer 993463 (antisense) shown below to generate a 1000 bp PCR fragment.

```
Primer 993453:
                                        (SEQ ID NO: 35)
5'-GTCGACTCGAAGCCCGAATGTAGGAT-3'

Primer 993463:
                                        (SEQ ID NO: 36)
5'-CCTCGATCCAACCAAGCTTCATGATGCGCAGTCCGCGGTTGACTA-3'
```

Primer sequences in italics are homologous to 24 bp of the *Trichoderma reesei* cbh1 promoter and underlined primer sequences are homologous to 22 bp of the *Aspergillus oryzae* beta-glucosidase full-length coding region. The 46 bp overlap between the promoter and the coding sequence allowed precise fusion of the 1000 bp fragment comprising the *Trichoderma reesei* cbh1 promoter to the 2586 bp fragment comprising the *Aspergillus oryzae* beta-glucosidase coding region.

The amplification reactions (50 μl) were composed of Pfx Amplification Buffer, 0.25 mM dNTPs, 100 ng of *Trichoderma reesei* RutC30 genomic DNA, 6.4 μM primer 993453, 3.2 μM primer 993463, 1 mM $MgCl_2$, and 2.5 units of Pfx DNA polymerase. The reactions were incubated in an EPPENDORF® MASTERCYCLER® 5333 programmed for 30 cycles each for 60 seconds at 94° C., 60 seconds at 55° C., and 180 seconds at 72° C. (15 minute final extension). The reaction products were isolated on a 1.0% agarose gel using TAE buffer where a 1000 bp product band was excised from the gel and purified using a QIAQUICK® Gel Extraction Kit according to the manufacturer's instructions.

The purified fragments were used as template DNA for subsequent amplification by overlapping PCR using primer 993453 (sense) and primer 993456 (antisense) shown above to precisely fuse the 1000 bp fragment comprising the *Trichoderma reesei* cbh1 promoter to the 2586 bp fragment comprising the *Aspergillus oryzae* beta-glucosidase full-length coding region.

The amplification reactions (50 μl) were composed of Pfx Amplification Buffer, 0.25 mM dNTPs, 6.4 μM primer 99353, 3.2 μM primer 993456, 1 mM $MgCl_2$, and 2.5 units of Pfx DNA polymerase. The reactions were incubated in an EPPENDORF® MASTERCYCLER® 5333 programmed for 30 cycles each for 60 seconds at 94° C., 60 seconds at 60° C., and 240 seconds at 72° C. (15 minute final extension).

Figure 9:
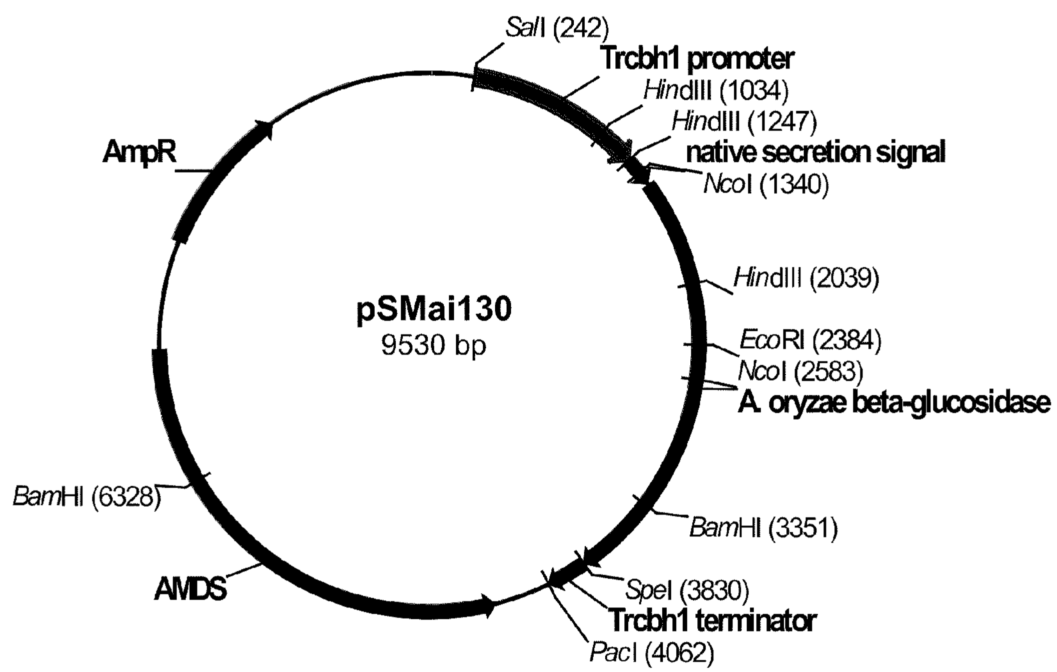
FIG. 9 shows a restriction map of pSMai130.

The resulting 3586 bp fragment was digested with Sal I and Spe I and ligated into pMJ04, digested with the same two restriction enzymes, to generate pSMai130 (FIG. 9). Plasmid pSMai130 comprises the *Trichoderma reesei* cellobiohydrolase I gene promoter and terminator operably linked to the *Aspergillus oryzae* native beta-glucosidase signal sequence and coding sequence (i.e., full-length *Aspergillus oryzae* beta-glucosidase coding sequence).

Example 13

Construction of pSMai135

The *Aspergillus oryzae* beta-glucosidase mature coding region (minus the native signal sequence, see FIG. 10; SEQ ID NOs: 37 and 38 for signal peptide and coding sequence thereof) from Lys-20 to the TAA stop codon was PCR amplified from pJaL660 as template with primer 993728 (sense) and primer 993727 (antisense) shown below.

```
Primer 993728:
                                        (SEQ ID NO: 39)
5'-TGCCGGTGTTGGCCCTTGCCAAGGATGATCTCGCGTACTCCC-3'

Primer 993727:
                                        (SEQ ID NO: 40)
5'-GACTAGTCTTACTGGGCCTTAGGCAGCG-3'
```

Sequences in italics are homologous to 20 bp of the *Humicola insolens* endoglucanase V signal sequence and sequences underlined are homologous to 22 bp of the *Aspergillus oryzae* beta-glucosidase coding region. A Spe I site was engineered into the 5' end of the antisense primer.

The amplification reactions (50 μl) were composed of Pfx Amplification Buffer, 0.25 mM dNTPs, 10 ng/μl of pJal660, 6.4 μM primer 993728, 3.2 μM primer 993727, 1 mM $MgCl_2$, and 2.5 units of Pfx DNA polymerase. The reactions were incubated in an EPPENDORF®MASTERCYCLER® 5333 programmed for 30 cycles each for 60 seconds at 94° C., 60 seconds at 55° C., and 180 seconds at 72° C. (15 minute final extension). The reaction products were isolated on a 1.0% agarose gel using TAE buffer where a 2523 bp product band was excised from the gel and purified using a QIAQUICK® Gel Extraction Kit according to the manufacturer's instructions.

A separate PCR amplification was performed to amplify 1000 bp of the *Trichoderma reesei* cbh1 promoter and 63 bp of the *Humicola insolens* endoglucanase V signal sequence (ATG start codon to Ala-21, FIG. 11, SEQ ID NOs: 41 and 42), using primer 993724 (sense) and primer 993729 (antisense) shown below.

```
Primer 993724:
                                        (SEQ ID NO: 43)
5'-ACGCGTCGACCGAATGTAGGATTGTTATCC-3'

Primer 993729:
                                        (SEQ ID NO: 44)
5'-GGGAGTACGCGAGATCATCCTTGGCAAGGGCCAACACCGGCA-3'
```

Primer sequences in italics are homologous to 20 bp of the *Humicola insolens* endoglucanase V signal sequence and underlined primer sequences are homologous to the 22 bp of the *Aspergillus oryzae* beta-glucosidase coding region.

Plasmid pMJ05, which comprises the *Humicola insolens* endoglucanase V coding region under the control of the cbh1 promoter, was used as template to generate a 1063 bp fragment comprising the *Trichoderma reesei* cbh1 promoter and *Humicola insolens* endoglucanase V signal sequence fragment. A 42 bp of overlap was shared between the *Trichoderma reesei* cbh1 promoter and *Humicola insolens* endoglucanase V signal sequence and the *Aspergillus oryzae* beta-glucosidase mature coding sequence to provide a perfect linkage between the promoter and the ATG start codon of the 2523 bp *Aspergillus oryzae* beta-glucosidase coding region.

The amplification reactions (50 μl) were composed of Pfx Amplification Buffer, 0.25 mM dNTPs, 10 ng/μl of pMJ05, 6.4 μM primer 993728, 3.2 μM primer 993727, 1 mM $MgCl_2$, and 2.5 units of Pfx DNA polymerase. The reactions were incubated in an EPPENDORF® MASTERCYCLER® 5333 programmed for 30 cycles each for 60 seconds at 94° C., 60 seconds at 60° C., and 240 seconds at 72° C. (15 minute final extension). The reaction products were isolated on a 1.0% agarose gel using TAE buffer where a 1063 bp product band was excised from the gel and purified using a QIAQUICK® Gel Extraction Kit according to the manufacturer's instructions.

The purified overlapping fragments were used as templates for amplification using primer 993724 (sense) and primer 993727 (antisense) described above to precisely fuse the 1063 bp fragment comprising the *Trichoderma reesei* cbh1 promoter and *Humicola insolens* endoglucanase V signal sequence to the 2523 bp fragment comprising the *Aspergillus oryzae* beta-glucosidase mature coding region frame by overlapping PCR.

The amplification reactions (50 μl) were composed of Pfx Amplification Buffer, 0.25 mM dNTPs, 6.4 μM primer 993724, 3.2 μM primer 993727, 1 mM $MgCl_2$, and 2.5 units of Pfx DNA polymerase. The reactions were incubated in an EPPENDORF® MASTERCYCLER® 5333 programmed for 30 cycles each for 60 seconds at 94° C., 60 seconds at 60° C., and 240 seconds at 72° C. (15 minute final extension). The reaction products were isolated on a 1.0% agarose gel using TAE buffer where a 3591 bp product band was excised from the gel and purified using a QIAQUICK® Gel Extraction Kit according to the manufacturer's instructions.

Figure 12:
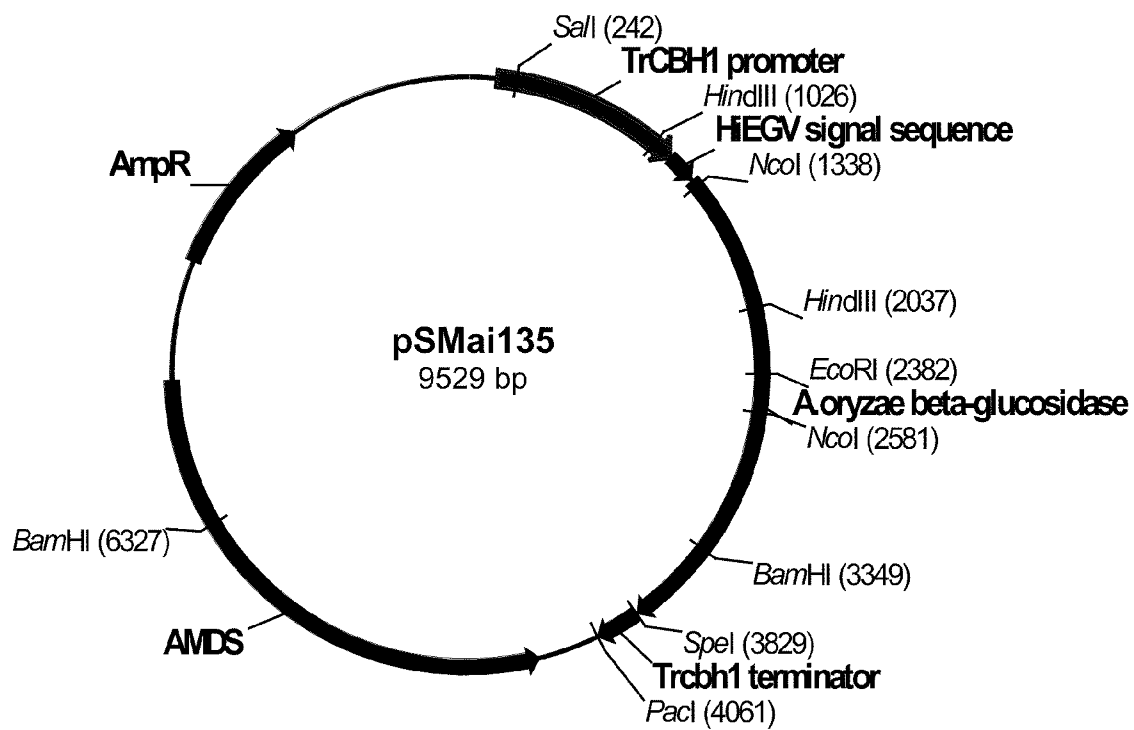
FIG. 12 shows a restriction map of pSMai135.

The resulting 3591 bp fragment was digested with Sal I and Spe I and ligated into pMJ04 digested with the same restriction enzymes to generate pSMai135 (FIG. 12). Plasmid pSMai135 comprises the *Trichoderma reesei* cellobiohydrolase I gene promoter and terminator operably linked to the *Humicola insolens* endoglucanase V signal sequence and the *Aspergillus oryzae* beta-glucosidase mature coding sequence.

Example 14

Expression of *Aspergillus oryzae* Beta-Glucosidase with the *Humicola insolens* Endoglucanase V Secretion Signal Plasmid pSMai135 encoding the mature *Aspergillus oryzae* beta-glucosidase linked to the *Humicola insolens* endoglucanase V secretion signal (FIG. 11), was introduced into *Trichoderma reesei* RutC30 by PEG-mediated transformation (Penttila et al., 1987, *Gene* 61 155-164). The plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of YP medium supplemented with 2% (w/v) glucose and 10 mM uridine for 17 hours. Mycelia was collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® (Novozymes A/S, Bagsværd, Denmark) per ml and 0.36 units of chitinase (Sigma Chemical Co., St. Louis, Mo., USA) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in STC to a final concentration of $1\times10^8$ protoplasts per ml. Excess protoplasts were stored in a Cryo 1° C. Freezing Container (Nalgene, Rochester, N.Y., USA) at −80° C.

Approximately 7 μg of pSMai135 digested with Pme I were added to 100 μl of protoplast solution and mixed gently, followed by 260 μl of PEG buffer, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were sub-cultured onto COVE2 plates and grown at 28° C.

Sixty-seven transformants designated SMA135 obtained with pSMai135 were subcultured onto fresh plates containing acetamide and allowed to sporulate for 7 days at 28° C.

The 67 SMA135 *Trichoderma reesei* transformants were cultivated in 125 ml baffled shake flasks containing 25 ml of cellulase-inducing medium at pH 6.0 inoculated with spores of the transformants and incubated at 28° C. and 200 rpm for 7 days. *Trichoderma reesei* RutC30 was run as a control. Culture broth samples were removed at day 7. One ml of each culture broth was centrifuged at 15,700×g for 5 minutes in a micro-centrifuge and the supernatants transferred to new tubes. Samples were stored at 4° C. until enzyme assay. The supernatants were assayed for beta-glucosidase activity using p-nitrophenyl-beta-D-glucopyranoside as substrate, as described below.

Beta-glucosidase activity was determined at ambient temperature using 25 μl aliquots of culture supernatants, diluted 1:10 in 50 mM succinate pH 5.0, in 200 μl of 0.5 mg/ml p-nitrophenyl-beta-D-glucopyranoside as substrate in 50 mM succinate pH 5.0. After 15 minutes incubation the reaction was stopped by adding 100 μl of 1 M Tris-HCl pH 8.0 and the absorbance was read spectrophotometrically at 405 nm. One unit of beta-glucosidase activity corresponded to production of 1 μmol of p-nitrophenyl per minute per liter at pH 5.0, ambient temperature. *Aspergillus niger* beta-glucosidase (NOVOZYM™ 188, Novozymes A/S, Bagsværd, Denmark) was used as an enzyme standard.

A number of the SMA135 transformants showed beta-glucosidase activities several-fold higher than that of *Trichoderma reesei* RutC30. Transformant SMA135-04 produced the highest beta-glucosidase activity.

SDS-PAGE was carried out using CRITERION® Tris-HCl (5% resolving) gels (Bio-Rad, Hercules, Calif., USA) with the CRITERION® System (Bio-Rad, Hercules, Calif., USA). Five μl of day 7 supernatants (see above) were suspended in 2× concentration of Laemmli Sample Buffer (Bio-Rad, Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad, Hercules, Calif., USA). The resulting gel was stained with BIO-SAFE® Coomassie Stain.

Totally, 26 of the 38 *Trichoderma reesei* SMA135 transformants produced a protein of approximately 110 kDa that was not visible in *Trichoderma reesei* RutC30 as control. Transformant *Trichoderma reesei* SMA135-04 produced the highest level of beta-glucosidase.

Example 15

Fermentation of *Trichoderma reesei* SMA135-04

One hundred ml of the following shake flask medium was added to a 500 ml shake flask. The shake flask medium was composed per liter of 20 g of dextrose, 10 g of corn steep solids, 1.45 g of $(NH_4)_2SO_4$, 2.08 g of $KH_2PO_4$, 0.36 g of $CaCl_2$, 0.42 g of $MgSO_4.7H_2O$, and 0.42 ml of trace metals solution. Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. The shake flask was inoculated with two plugs from a solid plate culture of *Trichoderma reesei* SMA135-04 and incubated at 28° C. on an orbital shaker at 200 rpm for 48 hours.

Fifty ml of the shake flask broth was used to inoculate a 3 liter fermentation vessel containing 1.8 liters of a fermentation batch medium composed per liter of 30 g of cellulose, 4 g of dextrose, 10 g of corn steep solids, 3.8 g of $(NH_4)_2SO_4$, 2.8 g of $KH_2PO_4$, 2.64 g of $CaCl_2$, 1.63 g of $MgSO_4.7H_2O$, 1.8 ml of anti-foam, and 0.66 ml of trace metals solution. Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. Fermentation feed medium was composed of dextrose and cellulose, which was dosed at a rate of 0 to 4 g/l/hr for a period of 165 hours. The fermentation vessel was maintained at a temperature of 28° C. and pH was controlled to a set-point of 4.75+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered and stored at 35 to 40° C.

Example 16

Characterization of *Thielavia terrestris* GH61F Polypeptide Having Cellulolytic Enhancing Activity Corn stover was pretreated at the U.S. Department of Energy's National Renewable Energy Laboratory (NREL), Golden, Colo., using dilute sulfuric acid. The following conditions were used for the pretreatment: 0.048 g sulfuric acid/g dry biomass at 190° C. and 25% w/w dry solids for around 1 minute. According to NREL, the water-insoluble solids in the pretreated corn stover (PCS) contained 53.2% cellulose, 3.2% hemicellulose and 31.5% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Prior to enzymatic hydrolysis, the PCS was washed with a large volume of deionized water to get rid of soluble compounds produced during acid pretreatment.

The *Thielavia terrestris* GH61F polypeptide was expressed in *Aspergillus oryzae* as described in Example 7, and the broth was centrifuged at 9500×g and the supernatant was then filtered through 0.22 μm filter (Millipore, Billerica, Mass., USA). The filtered broth was desalted using an ECONO-PAC® 10DG column (Bio-Rad, Hercules, Calif., USA).

A *Trichoderma reesei* cellulase preparation containing an *Aspergillus oryzae* beta-glucosidase (WO 02/095014), hereinafter called Tr/AoBG, was obtained as described in Example 15.

Hydrolysis of PCS (45 mg/ml in 50 mM sodium acetate pH 5.0 buffer) was conducted using 96-well deep-well plates (Axygen Scientific, Inc., Union City, Calif., USA) sealed by an ALPS 300™ automated lab plate sealer (ABgene Inc., Rochester, N.Y., USA), with a total reaction volume of 1.0 ml.

The *Thielavia terrestris* GH61F polypeptide was tested for its ability to enhance the hydrolytic ability of the *Trichoderma reesei* cellulase preparation containing the *Aspergillus oryzae* beta-glucosidase. Hydrolysis of PCS was performed using 2.25, 4.5 and 6.75 mg of the *Trichoderma reesei* cellulase preparation containing the *Aspergillus oryzae* beta-glucosidase per gram of cellulose, supplemented with 0.25, 0.5 and 0.75 mg of *Thielavia terrestris* GH61F polypeptide per gram of cellulose, respectively, in comparison with 2.5, 5.0 and 7.5 mg of the *Trichoderma reesei* cellulase preparation containing the *Aspergillus oryzae* beta-glucosidase alone per gram of cellulose, respectively. PCS hydrolysis was performed at 50 and 60° C. in a TS Autoflow $CO_2$ Water Jacketed Incubator (NuAire Inc., Plymouth, Minn., USA). Reactions were run in triplicates and aliquots taken during the course of hydrolysis. PCS hydrolysis reactions were stopped by mixing a 20 μl aliquot of each hydrolyzate with 180 μl of 0.1 M NaOH (stop reagent). Appropriate serial dilutions were generated for each sample and the reducing sugar content determined using a para-hydroxybenzoic acid hydrazide (PHBAH, Sigma Chemical Co., St. Louis, Mo., USA) assay adapted to a 96 well microplate format as described below. Briefly, a 100 μl aliquot of an appropriately diluted sample was placed in a 96 well conical bottomed microplate. Reactions were initiated by adding 50 μl of 1.5% (w/v) PHBAH in 0.5 M NaOH to each well. Plates were heated uncovered at 95° C. for 10 minutes. Plates were allowed to cool to room temperature (RT) and 50 μl of distilled water added to each well. A 100 μl aliquot from each well was transferred to a flat bottomed 96 well plate and the absorbance at 410 nm measured using a SPECTRAMAX® Microplate Reader (Molecular Devices, Sunnyvale, Calif., USA). Glucose standards (0.1-0.0125 mg/ml diluted with 0.1 M sodium hydroxide) were used to prepare a standard curve to translate the obtained $A_{410\ nm}$, values into glucose equivalents. The resultant equivalents were used to calculate the percentage of PCS cellulose conversion for each reaction.

The degree of cellulose conversion to reducing sugar (conversion, %) was calculated using the following equation:

$$\text{Conversion}_{(\%)} = RS_{(mg/ml)} \times 100 \times 162/(\text{cellulose}_{(mg/ml)} \times 180) = RS_{(mg/ml)} \times 100/(\text{cellulose}_{(mg/ml)} \times 1.111)$$

In this equation, RS is the concentration of reducing sugar in solution measured in glucose equivalents (mg/ml), and the factor 1.111 reflects the weight gain in converting cellulose to glucose.

Cellulose conversions by the *Trichoderma reesei* cellulase preparation containing the *Aspergillus oryzae* beta-glucosidase alone (2.5, 5 and 7.5 mg/g cellulose) or 10% replaced by the *Thielavia terrestris* GH61F polypeptide (2.25+0.25, 4.5+0.5, 6.75+0.75 mg/g cellulose) are summarized in Table 1.

TABLE 1

Cellulose conversion by the *Trichoderma reesei* cellulase preparation containing an *Aspergillus oryzae* beta-glucosidase alone or supplemented with *Thielavia terrestris* GH61F polypeptide at 50° C. and 60° C., pH 5.0 for 120 hours.

| Test # | Name | Loading, mg/g cellulose | Temp, ° C. | Conversion at 120 h, % |
|---|---|---|---|---|
| 1 | Tr/AoBG | 2.5 | 50 | 59.1 |
| 2 | Tr/AoBG + *T. terrestris* GH61F | 2.25 + 0.25 | 50 | 66.3 |

TABLE 1-continued

Cellulose conversion by the *Trichoderma reesei* cellulase preparation containing an *Aspergillus oryzae* beta-glucosidase alone or supplemented with *Thielavia terrestris* GH61F polypeptide at 50° C. and 60° C., pH 5.0 for 120 hours.

| Test # | Name | Loading, mg/g cellulose | Temp, ° C. | Conversion at 120 h, % |
|---|---|---|---|---|
| 3 | Tr/AoBG | 5.0 | 50 | 81.8 |
| 4 | Tr/AoBG + *T. terrestris* GH61F | 4.5 + 0.5 | 50 | 88.1 |
| 5 | Tr/AoBG | 7.5 | 50 | 90.7 |
| 6 | Tr/AoBG + *T. terrestris* GH61F | 6.75 + 0.75 | 50 | 97.3 |
| 7 | *T. terrestris* GH61F | 0.75 | 50 | 1.6 |
| 8 | Tr/AoBG | 2.5 | 60 | 30.0 |
| 9 | Tr/AoBG + *T. terrestris* GH61F | 2.25 + 0.25 | 60 | 34.9 |
| 10 | Tr/AoBG | 5.0 | 60 | 44.6 |
| 11 | Tr/AoBG + *T. terrestris* GH61F | 4.5 + 0.5 | 60 | 51.0 |
| 12 | Tr/AoBG | 7.5 | 60 | 55.4 |
| 13 | Tr/AoBG + *T. terrestris* GH61F | 6.75 + 0.75 | 60 | 63.7 |
| 14 | *T. terrestris* GH61F | 0.75 | 60 | 0.9 |

The results shown in Table 1 demonstrated that the *Thielavia terrestris* GH61F polypeptide enhanced the activity of the *Trichoderma reesei* cellulase preparation containing the *Aspergillus oryzae* beta-glucosidase on PCS. The *Thielavia terrestris* GH61F polypeptide by itself (0.75 mg per g of cellulose) yielded a cellulose conversion after 120 hours of 1.6% at 50° C., and 0.9% at 60° C. Supplementing 0.75 mg of the *Thielavia terrestris* GH61F polypeptide to 6.75 mg of the *Trichoderma reesei* cellulase preparation containing the *Aspergillus oryzae* beta-glucosidase yielded a cellulose conversion higher than that by 7.5 mg of Tr/AoBG, at both 50 and 60° C., indicating the activity of the *Trichoderma reesei* cellulase preparation containing the *Aspergillus oryzae* beta-glucosidase on PCS was boosted by the *Thielavia terrestris* GH61F polypeptide, and that there were synergistic effects between the *Trichoderma reesei* cellulase preparation containing the *Aspergillus oryzae* beta-glucosidase and the *Thielavia terrestris* GH61F polypeptide.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* pTter61F | NRRL B-50044 | May 25, 2007 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polynucleotide that encodes a polypeptide having cellulolytic enhancing activity, wherein the polypeptide comprises an amino acid sequence having at least 95% sequence identity to the mature polypeptide of SEQ ID NO: 2.

2. The isolated polynucleotide of claim 1, that encodes a polypeptide comprising or consisting of the amino acid sequence of SEQ ID NO: 2.

3. The isolated polynucleotide of claim 1, wherein the mature polypeptide is amino acids 16 to 317 of SEQ ID NO: 2.

4. A nucleic acid construct comprising the polynucleotide of claim 1 operably linked to one or more control sequences that direct the production of the polypeptide in an expression host.

5. A recombinant expression vector comprising the nucleic acid construct of claim 4.

6. A recombinant host cell comprising the nucleic acid construct of claim 4.

7. A method of producing a polypeptide having cellulolytic enhancing activity, comprising: (a) cultivating the host cell of claim 6 under conditions conducive for production of the polypeptide; and (b) recovering the polypeptide.

8. A method of producing a mutant of a parent cell, comprising disrupting or deleting a polynucleotide sequence that encodes a polypeptide having cellulolytic enhancing activity and at least 95% sequence identity to the mature polypeptide of SEQ ID NO: 2, which results in the mutant producing less of the polypeptide than the parent cell.

9. A method of producing a polypeptide having cellulolytic enhancing activity, comprising: (a) cultivating a transgenic plant or a plant cell comprising the polynucleotide of claim 1 under conditions conducive for production of the polypeptide; and (b) recovering the polypeptide.

10. A transgenic plant, plant part or plant cell transformed with the polynucleotide of claim 1.

11. A nucleic acid construct comprising a gene encoding a protein operably linked to a nucleotide sequence encoding a signal peptide comprising or consisting of amino acids 1 to 15 of SEQ ID NO: 2, wherein the gene is foreign to the nucleotide sequence.

12. A recombinant host cell comprising the nucleic acid construct of claim 11.

13. A method of producing a protein, comprising: (a) cultivating the recombinant host cell of claim 12 under conditions conducive for production of the protein; and (b) recovering the protein.

14. The isolated polynucleotide of claim 1, that encodes a polypeptide having at least 97% sequence identity to the mature polypeptide of SEQ ID NO: 2.

15. The isolated polynucleotide of claim 1, that encodes a polypeptide having at least 98% sequence identity to the mature polypeptide of SEQ ID NO: 2.

16. The isolated polynucleotide of claim 1, that encodes a polypeptide having at least 99% sequence identity to the mature polypeptide of SEQ ID NO: 2.

17. The isolated polynucleotide of claim 3, comprising or consisting of the nucleotide sequence of SEQ ID NO: 1.

18. An isolated polynucleotide that encodes a polypeptide having cellulolytic enhancing activity, selected from the group consisting of:

(a) a polynucleotide that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) a polynucleotide comprising a nucleotide sequence having at least 95% sequence identity to the mature polypeptide coding sequence of SEQ ID NO: 1.

19. The isolated polynucleotide of claim 18, that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

20. The isolated polynucleotide of claim 18, that hybridizes under at least very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

21. The isolated polynucleotide of claim 18, comprising a nucleotide sequence having at least 95% sequence identity to the mature polypeptide coding sequence of SEQ ID NO: 1.

22. The isolated polynucleotide of claim 18, comprising a nucleotide sequence having at least 97% sequence identity to the mature polypeptide coding sequence of SEQ ID NO: 1.

23. The isolated polynucleotide of claim 18, comprising a nucleotide sequence having at least 98% sequence identity to the mature polypeptide coding sequence of SEQ ID NO: 1.

24. The isolated polynucleotide of claim 18, comprising a nucleotide sequence having at least 99% sequence identity to the mature polypeptide coding sequence of SEQ ID NO: 1.

25. The isolated polynucleotide of claim 18, wherein the mature polypeptide coding sequence is nucleotides 46 to 951 of SEQ ID NO: 1.

26. The method of claim 8, wherein the polypeptide comprises the amino acid sequence of SEQ ID NO: 2.

27. The method of claim 8, wherein the polynucleotide sequence comprises the nucleotide sequence of SEQ ID NO: 1.

* * * * *